(12) United States Patent
Duddu et al.

(10) Patent No.: US 7,326,691 B2
(45) Date of Patent: Feb. 5, 2008

(54) COMPOSITIONS COMPRISING AMPHOTERICIN B, METHODS, AND SYSTEMS

(75) Inventors: Sarma Duddu, Redwood City, CA (US); Srinivas Palakodaty, Foster City, CA (US); David Lechuga-Ballesteros, San Jose, CA (US); Danforth Miller, San Carlos, CA (US); Alan R. Kugler, Montara, CA (US); Christopher Frantz, Sunnyvale, CA (US); Trixie Tan, Daly City, CA (US); Richard Malcolmson, San Mateo, CA (US); Keith Washco, Fremont, CA (US); Theresa Sweeney, El Granada, CA (US); Thomas E. Tarara, Burlingame, CA (US); Sarvajna Dwivedi, Redwood City, CA (US); Michael A. Eldon, Redwood City, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 11/158,332

(22) Filed: Jun. 21, 2005

(65) Prior Publication Data
US 2006/0025355 A1 Feb. 2, 2006

Related U.S. Application Data

(60) Provisional application No. 60/581,586, filed on Jun. 21, 2004.

(51) Int. Cl.
*A61K 9/14* (2006.01)
*A61K 31/70* (2006.01)
(52) U.S. Cl. .................. 514/31; 536/6.5; 424/489
(58) Field of Classification Search .............. 514/31; 536/6.5
See application file for complete search history.

(56) References Cited

U.S. PATENT DOCUMENTS

| | | |
|---|---|---|
| 3,991,761 A | 11/1976 | Cocozza |
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,995,385 A | 2/1991 | Valentini et al. |
| 5,049,388 A | 9/1991 | Knight et al. |
| 5,458,135 A | 10/1995 | Patton et al. |
| 5,619,985 A | 4/1997 | Ohki et al. |
| 5,776,904 A * | 7/1998 | Seki et al. .................... 514/31 |
| 5,785,049 A | 7/1998 | Smith et al. |
| 5,855,913 A | 1/1999 | Hanes et al. |
| 5,858,410 A | 1/1999 | Muller et al. |
| 5,874,064 A | 2/1999 | Edwards et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |
| 6,077,543 A | 6/2000 | Gordon et al. |
| 6,228,346 B1 | 5/2001 | Zhang et al. |
| 6,257,233 B1 | 7/2001 | Burr et al. |
| 6,357,490 B1 | 3/2002 | Johnston et al. |
| 6,358,530 B1 | 3/2002 | Eljamal et al. |
| 6,372,258 B1 | 4/2002 | Platz et al. |
| 6,503,480 B1 | 1/2003 | Edwards et al. |
| 6,546,929 B2 | 4/2003 | Burr et al. |

FOREIGN PATENT DOCUMENTS

| | | |
|---|---|---|
| WO | 95/01221 | 1/1995 |
| WO | 95/24183 | 9/1995 |
| WO | 95/31479 | 11/1995 |
| WO | 96/00610 | 1/1996 |
| WO | 96/32096 | 10/1996 |
| WO | 96/32149 | 10/1996 |
| WO | 98/36825 | 8/1998 |
| WO | 99/16419 | 4/1999 |
| WO | 99/16420 | 4/1999 |
| WO | 99/16421 | 4/1999 |
| WO | 99/16422 | 4/1999 |
| WO | 00/07572 | 2/2000 |
| WO | 00/72904 | 12/2000 |
| WO | 01/00312 | 1/2001 |
| WO | 01/85136 | 11/2001 |
| WO | 01/85137 | 11/2001 |
| WO | 02/054868 | 7/2002 |
| WO | 02/083220 | 10/2002 |

\* cited by examiner

*Primary Examiner*—Elli Peselev
(74) *Attorney, Agent, or Firm*—Steven J. Helmer; Michael J. Mazza

(57) ABSTRACT

A composition includes particles including at least about 95 wt % of amphotericin B, wherein the particles have a mass median diameter ranging from about 1.1 μm to about 1.9 μm. Another composition also includes particles including at least about 95 wt % of amphotericin B, wherein at least about 80 wt % of the particles have a geometric diameter ranging from about 1.1 μm to about 1.9 μm. Yet another composition includes particles including amphotericin B, wherein the particles have a mass median diameter less than about 1.9 μm, and wherein the amphotericin B has a crystallinity level of at least about 20%. Unit dosage forms, delivery systems, and methods may involve similar compositions.

6 Claims, 20 Drawing Sheets

COMPOSITIONS COMPRISING AMPHOTERICIN B, METHODS, AND SYSTEMS

The present application claims priority under 35 U.S.C. § 119(e) of U.S. Provisional Application No. 60/581,586, filed Jun. 21, 2004, which is incorporated herein by reference in its entirety.

BACKGROUND

1. Field of the Invention

One or more embodiments of the present invention include compositions comprising amphotericin B, methods of making and using amphotericin B compositions, and systems for using amphotericin B compositions.

2. Background Art

Pulmonary fungal infections, such as invasive filamentous pulmonary fungal infection (IFPFI), are major causes of morbidity and mortality in immunocompromised patients. The immune system of an individual may be compromised by some diseases, such as acquired immunodeficiency syndrome (AIDS), and/or may be deliberately compromised by immunosuppressive therapy. Immunosuppressive therapy is often administered to patients undergoing cancer treatments and/or patients undergoing a transplant procedure. Immunocompromised patients have an increased susceptibility to pulmonary and/or nasal fungal infections. Severely immunocompromised patients, such as those with prolonged neutropenia or patients requiring 21 or more consecutive days of prednisone at doses of at least 1 mg/kg/day in addition to their other immunosuppressants, are particularly susceptible to pulmonary and/or nasal fungal infection. Among immunocompromised patients, overall fungal infection rates range from 0.5 to 28%. Of the autopsied bone marrow transplant patients with idiopathic pneumonia syndrome (IPS) at the Fred Hutchinson Cancer Center, 7.3% had IFPFI. In another study by Vogeser et al, a 4% rate of IFPFI was found in 1187 consecutive autopsies in European patients dying of any cause during the period from 1993 to 1996. An overwhelming majority of these European patients had received (1) high dose steroid doses; (2) treatment for a malignancy; (3) a solid organ transplant; or (4) some form of bone marrow transplant.

The most common pulmonary and/or nasal fungal infection in immunocompromised patients is pulmonary and/or nasal aspergillosis. Aspergillosis is a disease caused by *Aspergillus* fungal species (*Aspergillus* spp.), which invade the body primarily through the lungs. The incidence of aspergillosis depends on duration and depth of neutropenia, patient factors (e.g., age, corticosteroid use, and prior pulmonary and/or nasal disease), levels of environmental contamination, criteria for diagnosis, and persistence in determining the cause of the disease.

Other filamentous and dimorphic fungi can lead to pulmonary fungal infections as well. These additional fungi are usually endemic and regional and may include, for example, blastomycosis, disseminated candidiasis, coccidioidomycosis, cryptococcosis, histoplasmosis, mucormycosis, and sporotrichosis. Though typically not affecting the pulmonary system, infections caused by *Candida* spp., which are usually systemic and most often result from infections via an indwelling device or IV catheter, wound, or a contaminated solid organ transplant, account for 50 to 67% of total fungal infections in immunocompromised patients.

Amphotericin B is the only approved fungicidal compound currently used to treat aspergillosis and is generally delivered intravenously. Amphotericin B is an amphoteric polyene macrolide obtained from a strain of *Streptomyces nodosus*. In its commercial form, amphotericin B is present in both amorphous and crystalline forms. Amphotericin B formulated with sodium desoxycholate was the first parental amphotericin B preparation to be marketed. Systemic intravenous therapies are constrained by dose-dependent toxicities, such as renal toxicity and hepatotoxicity, which hamper the effectiveness of the treatment and lessen the desirability of prophylactic use of amphotericin B. Even with the approved therapy, aspergillosis incidence is rising and estimated to cause mortality in more than 50% of those infected who receive treatment.

There remains a need in the art for safe and effective amphotericin B compositions, methods of making and using such compositions, and systems for using such compositions. For example, there remains a need for compositions and methods to safely and effectively treat patients who have developed a pulmonary and/or nasal fungal infection and/or provide prophylaxis against the onset of a pulmonary and/or nasal fungal infection.

SUMMARY OF THE INVENTION

Accordingly, one or more embodiments of the present invention include compositions comprising amphotericin B, methods of making and using amphotericin B compositions, and systems for using amphotericin B compositions. Other features and advantages of embodiments of the present invention will be set forth in the description of invention that follows, and in part will be apparent from the description or may be learned by practice of the invention. Embodiments of the invention will be realized and attained by the compositions and methods particularly pointed out in the written description and claims hereof.

In one aspect, one or more embodiments of the present invention are directed to a composition comprising particles comprising at least about 95 wt % of amphotericin B. The particles have a mass median diameter ranging from about 1.1 μm to about 1.9 μm.

In another aspect, one or more embodiments of the present invention are directed to a composition comprising particles comprising at least about 95 wt % of amphotericin B. At least about 80 wt % of the particles have a geometric diameter ranging from about 1.1 μm to about 1.9 μm.

In still another aspect, one or more embodiments of the present invention are directed to a composition comprising particles comprising amphotericin B. The particles have a mass median diameter less than about 1.9 μm, and the amphotericin B has a crystallinity level of at least about 20%.

In yet another aspect, one or more embodiments of the present invention are directed to a pharmaceutical composition comprising an effective amount of amphotericin B and pharmaceutically acceptable excipient. The pharmaceutical composition is made from particles comprising amphotericin B having a mass median diameter ranging from about 1.1 μm to about 1.9 μm.

In another aspect, one or more embodiments of the present invention are directed to a pharmaceutical composition comprising an effective amount of amphotericin B and pharmaceutically acceptable excipient. The pharmaceutical composition is made from particles comprising amphotericin B, and at least about 80 wt % of the particles comprising amphotericin B have a geometric diameter ranging from about 1.1 μm to about 1.9 μm.

In still another aspect, one or more embodiments of the present invention are directed to a pharmaceutical composition comprising an effective amount of amphotericin B and pharmaceutically acceptable excipient. The amphotericin B has a crystallinity level ranging from about 20% to about 99%.

In another aspect, one or more embodiments of the present invention are directed to a dry powder comprising amphotericin B having a crystallinity level of at least about 20%. The dry powder comprises particles having a mass median aerodynamic diameter of less than about 10 µm.

In a further aspect, one or more embodiments of the present invention are directed to a unit dosage form comprising a container containing a pharmaceutical composition. The pharmaceutical composition comprises an effective amount of amphotericin B and pharmaceutically acceptable excipient. The pharmaceutical composition is made from particles comprising amphotericin B having a mass median diameter less than about 1.9 µm.

In another aspect, one or more embodiments of the present invention are directed to a unit dosage form comprising a container containing a pharmaceutical composition. The pharmaceutical composition comprises an effective amount of amphotericin B and pharmaceutically acceptable excipient. The pharmaceutical composition is made from particles comprising amphotericin B, and at least about 80 wt % of the particles comprising amphotericin B have a geometric diameter less than about 1.9 µm.

In yet another aspect, one or more embodiments of the present invention are directed to a unit dosage form comprising a container containing a pharmaceutical composition. The pharmaceutical composition comprises amphotericin B and pharmaceutically acceptable excipient. The amphotericin B has a crystallinity level ranging from about 20% to about 99%.

In still another aspect, one or more embodiments of the present invention are directed to a delivery system comprising an inhaler and a pharmaceutical composition. The pharmaceutical composition comprises particulates comprising amphotericin B and pharmaceutically acceptable excipient. The particulates are made from particles comprising amphotericin B having a mass median diameter less than about 1.9 µm.

In a further aspect, one or more embodiments of the present invention are directed to a delivery system comprising an inhaler and a pharmaceutical composition. The pharmaceutical composition comprises particulates comprising amphotericin B and pharmaceutically acceptable excipient. The particulates are made from particles comprising amphotericin B, wherein at least about 80 wt % of the particles comprising amphotericin B have a geometric diameter less than about 1.9 µm.

In yet another aspect, one or more embodiments of the present invention are directed to a delivery system comprising an inhaler and a pharmaceutical composition. The pharmaceutical composition comprises particulates comprising amphotericin B having a crystallinity level ranging from about 20% to about 99%, and pharmaceutically acceptable excipient.

In still another aspect, one or more embodiments of the present invention are directed to a method of characterizing amphotericin B for making a pharmaceutical composition. The method includes determining a crystallinity level of an amphotericin B composition. The method also includes ensuring that the crystallinity level is greater than a first predetermined level before releasing the amphotericin B composition for combination with a pharmaceutically acceptable excipient to form a pharmaceutical composition.

In another aspect, one or more embodiments of the present invention are directed to a method of characterizing amphotericin B for making a pharmaceutical composition. The method includes determining an amorphicity of an amphotericin B composition. The method also includes ensuring that the amorphicity is less than a predetermined level before releasing the amphotericin B composition for combination with a pharmaceutically acceptable excipient to form the pharmaceutical composition.

In another aspect, one or more embodiments of the present invention are directed to a method of making and characterizing a dry powder pharmaceutical composition. The method includes combining an amphotericin B composition with a pharmaceutically acceptable excipient to form the dry powder pharmaceutical composition. The method also includes determining a mass median aerodynamic diameter of the dry powder pharmaceutical composition. The method further includes ensuring that the mass median aerodynamic diameter is less than a predetermined level before releasing the dry powder pharmaceutical composition for administration to a patient.

In yet another aspect, one or more embodiments of the present invention are directed to a method of making and characterizing a dry powder pharmaceutical composition. The method includes combining an amphotericin B composition with a pharmaceutically acceptable excipient to form the dry powder pharmaceutical composition. The method also includes determining a degree of homogeneity of the dry powder pharmaceutical composition. The method further includes ensuring that the degree of homogeneity is above a predetermined level before releasing the dry powder pharmaceutical composition for administration to a patient.

In another aspect, one or more embodiments of the present invention are directed to a method of making spray-dried particles. The method includes suspending particles comprising amphotericin B in a liquid to form a feedstock. The particles have a mass median diameter of less than about 3 µm. The method also includes spray drying the feedstock to produce the spray-dried particles.

In still another aspect, one or more embodiments of the present invention are directed to a method of making spray-dried particles. The method includes suspending the particles comprising amphotericin B in a liquid to form a feedstock, wherein the amphotericin B has a crystallinity level of at least about 20%. The method further includes spray drying the feedstock to produce the spray-dried particles.

In another aspect, one or more embodiments of the present invention are directed to a method of treating and/or providing prophylaxis against fungal infection. The method includes administering by inhalation an effective amount of a composition comprising amphotericin B to a patient in need thereof, wherein the composition is made from particles comprising amphotericin B having a mass median diameter ranging from about 1.1 µm to about 1.9 µm.

In still another aspect, one or more embodiments of the present invention are directed to a method of treating and/or providing prophylaxis against fungal infection. The method includes administering by inhalation an effective amount of a composition comprising amphotericin B to a patient in need thereof, wherein the composition is made from particles comprising amphotericin B, and wherein at least about 80 wt % of the particles comprising amphotericin B have a geometric diameter ranging from about 1.1 µm to about 1.9 µm.

In another aspect, one or more embodiments of the present invention are directed to a method of treating and/or providing prophylaxis against fungal infection. The method includes administering by inhalation an effective amount of a composition comprising amphotericin B to a patient in need thereof, wherein the amphotericin B has a crystallinity level of at least about 20%.

In a further aspect, one or more embodiments of the present invention are directed to a method of treating and/or providing prophylaxis against fungal infection. The method includes administering by inhalation an effective amount of a composition comprising amphotericin B to a patient in need thereof. The amphotericin B has a crystallinity level of at least about 20%, and the amphotericin B has a lung solid tissue residence half-life of at least about 1 week, as measured by lung tissue biopsy.

In another aspect, one or more embodiments of the present invention are directed to a method of treating and/or providing prophylaxis against fungal infection. The method includes administering by inhalation an effective amount of a composition comprising amphotericin B to a patient in need thereof. The amphotericin B has a crystallinity level of at least about 20%, and the amphotericin B has a lung epithelial lining fluid residence half-life of at least about 10 hours, as measured by bronchoalveolar lavage.

In yet another aspect, one or more embodiments of the present invention are directed to a method of treating and/or providing prophylaxis against fungal infection. The method includes administering by inhalation a composition comprising an amount of amphotericin B ranging from about 0.01 mg/kg to 7.0 mg/kg, to a patient in need thereof. The amphotericin B has a crystallinity level of at least about 20%, and plasma amphotericin B concentration remains less than about 1000 ng/mL.

In another aspect, one or more embodiments of the present invention are directed to a method of treating and/or providing prophylaxis against fungal infection. The method includes administering by inhalation a composition comprising an amount of amphotericin B ranging from about 0.01 mg/kg to 7.0 mg/kg, to a patient in need thereof. The amphotericin B has a crystallinity level of at least about 20%, and plasma amphotericin B concentrations remain low enough to avoid renal and/or hepatic toxicity.

In still another aspect, one or more embodiments of the present invention are directed to a method of treating and/or providing prophylaxis against fungal infection. The method includes administering by inhalation a composition comprising amphotericin B to a patient in need thereof. The amphotericin B has a crystallinity level of at least about 20%. The lung amphotericin B concentration reaches at least about 5 times minimum inhibitory concentration for a least a portion of treatment time, as measured by bronchoalveolar lavage. Plasma amphotericin B concentration remains less than about 1000 ng/mL.

In another aspect, one or more embodiments of the present invention are directed to a method of treating and/or providing prophylaxis against fungal infection. The method includes administering by inhalation a composition comprising amphotericin B to a patient in need thereof. The amphotericin B has a crystallinity level of at least about 20%. A treatment time ranges from about 15 weeks to about 20 weeks. Lung amphotericin B concentration reaches at least about 5 times minimum inhibitory concentration for a least a portion of the treatment time, as measured by bronchoalveolar lavage.

In a further aspect, one or more embodiments of the present invention are directed to a method of treating and/or providing prophylaxis against fungal infection. The method includes administering by inhalation a composition comprising an amount of amphotericin B ranging from about 2 mg to about 50 mg, to a patient in need thereof. The amphotericin B has a crystallinity level of at least about 20%. The administration is carried out in less than about 5 minutes.

In another aspect, one or more embodiments of the present invention are directed to a method of treating and/or providing prophylaxis against fungal infection. The method includes administering by inhalation an effective amount of dry powder comprising amphotericin B to a patient in need thereof. The amphotericin B has a crystallinity level of at least about 20%, and the dry powder comprises particles having a mass median aerodynamic diameter less than about 10 μm.

DRAWINGS

Embodiments of the present invention are further described in the description of invention that follows, in reference to the noted plurality of non-limiting drawings, wherein.

DESCRIPTION

Figure 1:
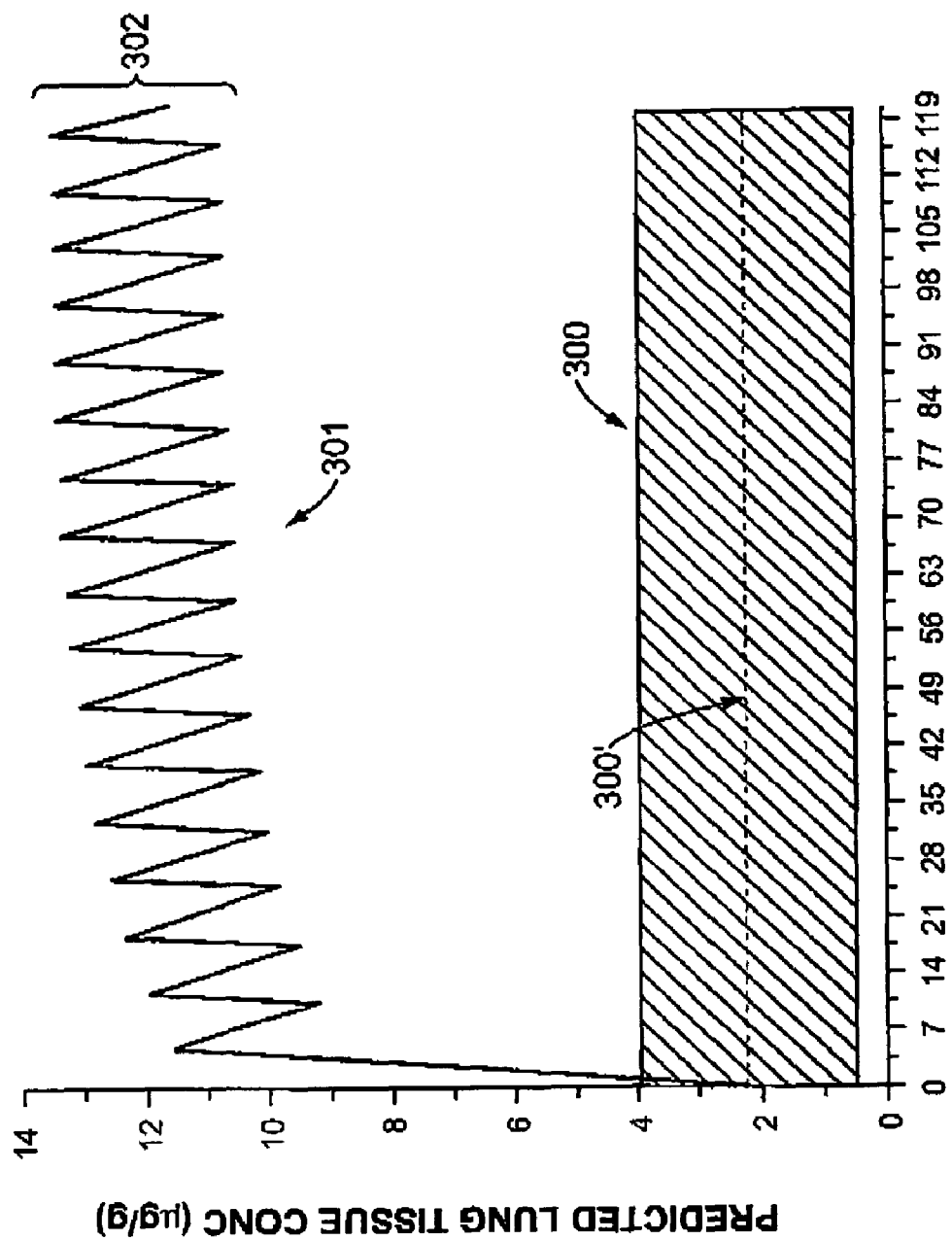
FIG. 1 shows predicted amphotericin B concentration in the lungs after administering a pharmaceutical composition according to the present invention.
Figure 2:
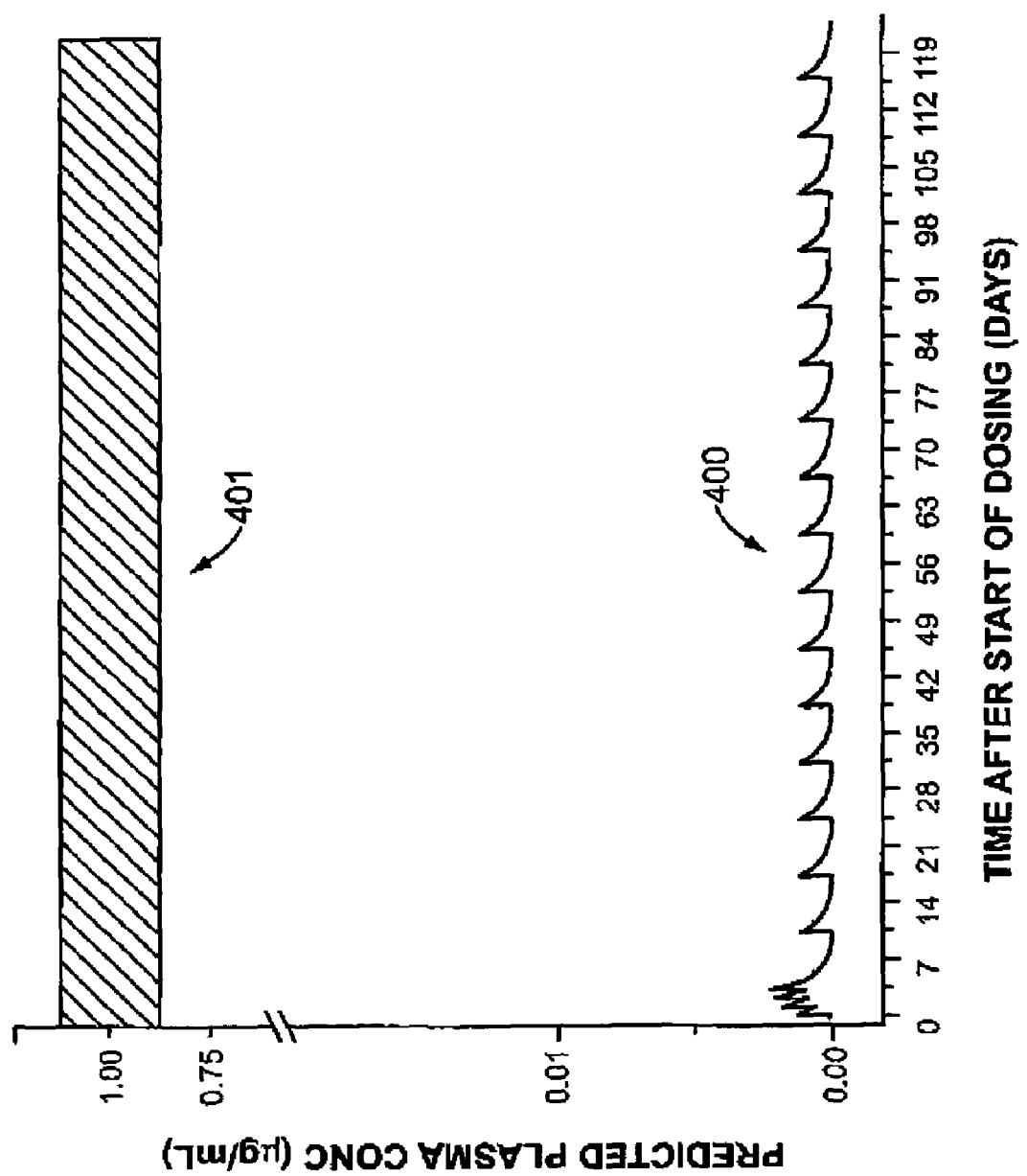
FIG. 2 shows predicted amphotericin B plasma concentration after administering a pharmaceutical composition according to the present invention.

It is to be understood that unless otherwise indicated the present invention is not limited to specific formulation components, drug delivery systems, manufacturing techniques, administration steps, or the like, as such may vary. In this regard, unless otherwise stated, a reference to a compound or component includes the compound or component by itself, as well as the compound in combination with other compounds or components, such as mixtures of compounds.

Before further discussion, a definition of the following terms will aid in the understanding of embodiments of the present invention.

As used herein, the singular forms "a," "an," and "the" include the plural reference unless the context clearly dictates otherwise. Thus, for example, reference to "a phospholipid" includes a single phospholipid as well as two or more phospholipids in combination or admixture unless the context clearly dictates otherwise.

As used herein, "particulates" refer to particles comprising amphotericin B and at least one pharmaceutically acceptable excipient. The particulates can assume various shapes and forms, such as hollow and/or porous microstructures. The hollow and/or porous microstructures may exhibit, define, or comprise voids, pores, defects, hollows, spaces, interstitial spaces, apertures, perforations, or holes, and may be spherical, collapsed, deformed, or fractured particles.

When referring to an active agent, the term encompasses not only the specified molecular entity, but also its pharmaceutically acceptable, pharmacologically active analogs, including, but not limited to, salts, esters, amides, hydrazides, N-alkyl derivatives, N-acyl derivatives, prodrugs, conjugates, active metabolites, and other such derivatives, analogs, and related compounds. Therefore, as used herein, the term "amphotericin B" refers to amphotericin B per se or derivatives, analogs, or related compounds noted above, as long as such amphotericin B derivatives, analogs, or related compounds exhibit antifungal activity.

As used herein, the terms "treating" and "treatment" refer to reduction in severity and/or frequency of symptoms, elimination of symptoms and/or underlying cause, reduction in likelihood of the occurrence of symptoms and/or underlying cause, and improvement or remediation of damage. Thus, "treating" a patient with an active agent as provided herein includes prevention of a particular condition, disease or disorder in a susceptible individual as well as treatment of a clinically symptomatic individual.

As used herein, "effective amount" refers to an amount covering both therapeutically effective amounts and prophylactically effective amounts.

As used herein, "therapeutically effective amount" refers to an amount that is effective to achieve the desired therapeutic result. A therapeutically effective amount of a given active agent will typically vary with respect to factors such as the type and severity of the disorder or disease being treated and the age, gender, and weight of the patient.

As used herein, "prophylactically effective amount" refers to an amount that is effective to achieve the desired prophylactic result. Because a prophylactic dose is administered in patients prior to onset of disease, the prophylactically effective amount typically is less than the therapeutically effective amount.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. Typically, powder samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" refers to the diameter of a single particle, as determined by microscopy, unless the context indicates otherwise.

As used herein, "mass median aerodynamic diameter" or "MMAD" refers to the median aerodynamic size of a plurality of particles or particulates, typically in a polydisperse population. The "aerodynamic diameter" is the diameter of a unit density sphere having the same settling velocity, generally in air, as a powder and is therefore a useful way to characterize an aerosolized powder or other dispersed particle or particulate formulation in terms of its settling behavior. The aerodynamic diameter encompasses particle or particulate shape, density, and physical size of the particle or particulate. As used herein, MMAD refers to the median of the aerodynamic particle or particulate size distribution of an aerosolized powder determined by cascade impaction, unless the context indicates otherwise.

As used herein, "crystallinity level" refers to the percentage of amphotericin B in crystalline form relative to the total amount of amphotericin B. Unless the context indicates to the contrary, crystallinity levels in this document are measured by wide angle X-ray powder diffraction. X-ray diffraction powder patterns were measured with a Shimadzu X-ray diffractometer model XRD-6000, with a dwell time of 2 seconds (fixed time scan), step size of 0.02°2θ, a scanning range of 3-42°2θ, 0.5° divergence slit, 1° scattering slit, and 0.3 mm receiving slit, as described in more detail in Example 1.

As used herein, "amorphicity" refers to the percentage of amphotericin B in amorphous form relative to the total amount of amphotericin B. Unless the context indicates to the contrary, amorphicity levels in this document are measured by wide angle X-ray powder diffraction.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., the mass of powder per unit dose placed into a suitable inhaler device prior to firing). The ED is an experimentally determined amount, and may be determined using an in vitro device set up which mimics patient dosing. To determine an ED value, as used herein, a nominal dose of dry powder (as defined above) is placed into a Turbospin® DPI device (PH&T, Italy), described in U.S. Pat. Nos. 4,069,819 and 4,995,385, which are incorporated herein by reference in their entireties. The Turbospin® DPI is actuated, dispersing the powder. The resulting aerosol cloud is then drawn from the device by vacuum (30 L/min) for 2.5 seconds after actuation, where it is captured on a tared glass fiber filter (Gelman, 47 mm diameter) attached to the device mouthpiece. The amount of powder that reaches the filter constitutes the delivered dose. For example, for a capsule containing 5 mg of dry powder that is placed into an inhalation device, if dispersion of the powder results in the recovery of 4 mg of powder on a tared filter as described above, then the ED for the dry powder composition is 80% [=4 mg (delivered dose)/5 mg (nominal dose)].

As used herein, "passive dry powder inhaler" refers to an inhalation device that relies upon a patient's inspiratory effort to disperse and aerosolize a pharmaceutical composition contained within the device in a reservoir or in a unit dose form and does not include inhaler devices which comprise a means for providing energy, such as pressurized gas and vibrating or rotating elements, to disperse and aerosolize the drug composition.

As used herein, "active dry powder inhaler" refers to an inhalation device that does not rely solely on a patient's inspiratory effort to disperse and aerosolize a pharmaceutical composition contained within the device in a reservoir or in a unit dose form and does include inhaler devices that comprise a means for providing energy to disperse and aerosolize the drug composition, such as pressurized gas and vibrating or rotating elements.

An overview of several embodiments of the present invention is set forth in the Summary of the Invention of this document. For the sake of brevity, this overview is incorporated herein by reference in its entirety.

One or more embodiments of the present invention relate to the surprising and unexpected discovery that certain amphotericin B compositions have reduced toxicity. While not wishing to be bound to theory, several factors appear to affect amphotericin B toxicity. These factors include, but are not limited to, crystallinity level of the amphotericin B, size of the amphotericin B particles, homogeneity of particulates comprising the amphotericin B particles, and size of particulates comprising the amphotericin B particles. Depending on the circumstances, one or more of these factors appear to affect toxicity.

In one or more embodiments of the invention, a composition comprises amphotericin B. Amphotericin B is a heptaene macrolide containing seven conjugated double bonds in the trans position and a 3-amino-3,6-dideoxymannose (mycosamine) moiety connected to the main ring by a glycosidic bond. Amphotericin B bulk drug substance may be obtained from Alpharma in Copenhagen, Denmark or Chemwerth, Woodbridge, Conn.

In one or more embodiments of the invention, a composition comprises an amphotericin B derivative having antifungal activity. The amphotericin B derivative can be an ester, amide, hydrazide, N-alkyl, and/or N-amino acyl. Examples of ester derivatives of amphotericin B include, but are not limited to, methyl esters, choline esters, and dimethylaminopropyl esters. Examples of amide derivatives of amphotericin B include, but are not limited to, primary, secondary and tertiary amides of amphotericin B. Examples of hydrazide derivatives of amphotericin B include, but are not limited to, N-methylpiperazine hydrazides. Examples of N-alkyl derivatives of amphotericin B include, but are not limited to, N',N',N'-trimethyl and N',N'-dimethylaminopropyl succinimidyl derivatives of amphotericin B methyl ester. Examples of N-aminoacyl derivatives of amphotericin B include, but are not limited to, N-ornithyl-, N-diaminopropionyl-, N-lysil-, N-hexamethyllysil-, and N-piperdine-propionyl- or N',N'-methyl-1-piperazine-propionyl-amphotericin B methyl ester.

Compositions including amphotericin B may include various amounts of amphotericin B. For example, the amount of amphotericin B may range from at least about 0.01 wt %, such as at least about 1 wt %, at least about 10 wt %, at least about 50 wt %, at least about 90 wt %, at least about 95 wt %, or at least about 98 wt %.

As noted above, the crystallinity level of amphotericin B appears to be a factor in reducing toxicity. For instance, when administered to the lungs, more crystalline forms of amphotericin B appear to dissolve slower and have a longer half-life than more amorphous forms of amphotericin B. While not wishing to be bound by theory, the slow dissolution and longer half-life appear to reduce toxicity. In contrast, while not wishing to be bound by theory, the amorphous form appears to develop soluble aggregates which might be toxic to the lung tissue. While not wishing to be bound by theory, it is believed that these principals are not limited to the lungs.

The desired crystallinity level of the amphotericin B will depend on factors such as dosage and treatment regimen. The crystallinity level of the amphotericin B may be at least about 10%, at least about 20%, at least about 30%, at least about 40%, at least about 50%, at least about 60%, at least about 70%, such as at least about 80%, at least about 90%, at least about 95%, or at least about 99%. Accordingly, the crystallinity level may range from about 10% to 100%, such as about 20% to about 99%, about 50% to about 99%, about 70% to about 99%, about 70% to about 98%, about 80% to about 98%, or about 90% to about 97%.

The crystallinity level may be determined by any of several known techniques. For instance, the crystallinity level may be determined by X-ray diffraction, Raman and/or infrared spectroscopy, dynamic vapor sorption, heat of solution calorimetry, or isothermal microcalorimetry. As noted above, unless the context indicates to the contrary, crystallinity levels in this document are measured by X-ray diffraction using the method set forth in Example 1.

In some cases, small diameter amphotericin B particles are used. In one version, the particles of amphotericin B have a mass median diameter less than about 3 μm, such as less than about 2.5 μm, less than about 2 μm, less than about 1.9 μm, or less than about 1.5 μm. For example, the particles of amphotericin B may have a mass median diameter ranging from about 0.5 µm to about 3 µm, such as about 0.5 µm to about 1.8 µm, about 0.8 µm to about 2.5 µm, about 1.1 µm to about 1.9 µm, about 1.2 µm to about 1.8 µm, or about 1 µm to about 2 µm. In some versions, at least about 20% of the amphotericin B particles have a size less than about 3 µm, such as at least about 50% are less than about 3 µm, at least about 90% are less than about 3 µm, or at least about 95% are less than about 3 µm, in diameter. For example, 60 wt %, 70 wt %, 80 wt %, or 90 wt % of the particles may have a mass median diameter of about 1.1 µm to 1.9 µm.

In some versions, the amphotericin B has a high crystallinity level, and the amphotericin B particle size is small. The crystallinity level may be any of those discussed above, and the particle size may be any of those discussed above. For instance, in one version, the crystallinity level is at least about 50%, and the mass median diameter is less than about 3 µm. In another version, the crystallinity level is at least about 70%, and the mass median diameter is less than about 2.8 µm. In still another version, the crystallinity level is at least about 80%, and the mass median diameter is less than about 2.6 µm. In yet another version, the crystallinity level is at least about 90%, and the mass median diameter is less than about 2.4 µm.

The crystallinity level may be at the levels discussed above, and the amphotericin B particle size may be larger than the sizes discussed above. For instance, the crystallinity level may be at least about 50%, and the mass median diameter may be greater than about 3 µm. Conversely, the amphotericin B particle size may be within the sizes discussed above, and the crystallinity level may be outside the levels discussed above. For instance, the mass median diameter may be less than about 3 µm, and the crystallinity level may be less than about 50%.

The pharmaceutical composition according to one or more embodiments of the invention may comprise amphotericin B and, optionally, one or more other active ingredients and/or pharmaceutically acceptable excipients. For example, the pharmaceutical composition may comprise neat particles of amphotericin B, may comprise neat particles of amphotericin B together with other particles, and/or may comprise particulates comprising amphotericin B and one or more active ingredients and/or one or more pharmaceutically acceptable excipients.

Thus, the pharmaceutical composition according to one or more embodiments of the invention may, if desired, contain a combination of amphotericin B and one or more other active ingredients. Examples of other active agents include, but are not limited to, agents that may be delivered through the lungs or nasal passages. For example, the other active agent(s) may be long-acting agents and/or active agents that are active against pulmonary and/or nasal infections such as antivirals, antifungals, and/or antibiotics.

Examples of antivirals include, but are not limited to, acyclovir, gangcyclovir, azidothymidine, cytidine arabinoside, ribavirin, rifampacin, amantadine, iododeoxyuridine, poscarnet, and trifluridine.

Examples of antifungals include, but are not limited to, azoles (e.g., imidazoles, itraconazole, pozaconazole), micafungin, caspafungin, salicylic acid, oxiconazole nitrate, ciclopirox olamine, ketoconazole, miconazole nitrate, and butoconazole nitrate.

Examples of antibiotics include, but are not limited to, penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, azlocillin, carbenicillin, mezlocillin, piperacillin, ticaricillin, and imipenim; cephalosporin and drugs of the cephalosporin family, including but not limited to cefadroxil, cefazolin, caphalexn, cephalothin, cephapirin, cephradine, cefaclor, cefamandole, cefonicid, cefoxin, cefuroxime, ceforanide, cefotetan, cefinetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracyclin and drugs of the tetracyclin family, for example, tetracyclin, oxytetracyclin, democlocyclin, methacyclin, doxycyclin, and minocyclin; quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacatracin, as well as other antimicrobial peptides such as defensins, magainins, cecropins, and others, provided as naturally-occurring or as the result of engineering to make such peptides resistant to the action of pathogen-specific proteases and other deactivating enzymes; other antimicrobial drugs, including chloramphenicol, vancomycin, rifampicin, metronidazole, voriconazole, fluconazole, ethambutol, pyrazinamide, sulfonamides, isoniazid, and erythromycin.

When a combination of active agents is used, the agents may be provided in combination in a single species of pharmaceutical composition or individually in separate species of pharmaceutical compositions. Further, the pharmaceutical composition may be combined with one or more other active or bioactive agents that provide the desired dispersion stability or powder dispersibility.

The amount of active agent(s), e.g., amphotericin B, in the pharmaceutical composition may vary. The amount of active agent(s) is typically at least about 5 wt %, such as at least about 10 wt %, at least about 20 wt %, at least about 30 wt %, at least about 40 wt %, at least about 50 wt %, at least about 60 wt %, at least about 70 wt %, or at least about 80 wt %, of the total amount of the pharmaceutical composition. The amount of active agent(s) generally varies between about 0.1 wt % to 100 wt %, such as about 5 wt % to about 95 wt %, about 10 wt % to about 90 wt %, about 30 wt % to about 80 wt %, about 40 wt % to about 70 wt %, or about 50 wt % to about 60 wt %.

As noted above, the pharmaceutical composition may include one or more pharmaceutically acceptable excipient. Examples of pharmaceutically acceptable excipients include, but are not limited to, lipids, metal ions, surfactants, amino acids, carbohydrates, buffers, salts, polymers, and the like, and combinations thereof.

Examples of lipids include, but are not limited to, phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In one or more embodiments, the phospholipid comprises a saturated phospholipid, such as one or more phosphatidylcholines. Exemplary acyl chain lengths are 16:0 and 18:0 (i.e., palmitoyl and stearoyl). The phospholipid content may be determined by the active agent activity, the mode of delivery, and other factors.

Phospholipids from both natural and synthetic sources may be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids comprise those that have a gel to liquid crystal phase transition greater than about 40° C., such as greater than about 60° C., or greater than about 80° C. The incorporated phospholipids may be relatively long chain (e.g., $C_{16}$-$C_{22}$) saturated lipids. Exemplary phospholipids useful in the disclosed stabilized preparations include, but are not limited to, phosphoglycerides such as dipalmitoylphosphatidylcholine, distearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition may also comprise a polyvalent cation, as disclosed in WO 01/85136 and WO 01/85137, which are incorporated herein by reference in their entireties. The polyvalent cation may be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C. The molar ratio of polyvalent cation to phospholipid may be at least about 0.05:1, such as about 0.05:1 to about 2.0:1 or about 0.25:1 to about 1.0:1. An example of the molar ratio of polyvalent cation:phospholipid is about 0.50:1. When the polyvalent cation is calcium, it may be in the form of calcium chloride. Although metal ion, such as calcium, is often included with phospholipid, none is required.

As noted above, the pharmaceutical composition may include one or more surfactants. For instance, one or more surfactants may be in the liquid phase with one or more being associated with solid particles or particulates of the composition. By "associated with" it is meant that the pharmaceutical compositions may incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and may be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated by reference herein in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338.

Examples of ionic surfactants include, but are not limited to, sodium sulfosuccinate, and fatty acid soaps.

Examples of amino acids include, but are not limited to, hydrophobic amino acids. Use of amino acids as pharmaceutically acceptable excipients is known in the art as disclosed in WO 95/31479, WO 96/32096, and WO 96/32149, which are incorporated herein by reference.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins.

Examples of buffers include, but are not limited to, tris or citrate.

Examples of acids include, but are not limited to, carboxylic acids.

Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like.

Examples of organic solids include, but are not limited to, camphor, and the like.

The pharmaceutical composition of one or more embodiments of the present invention may also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions may be tailored to optimize the effectiveness of the active agent(s).

Besides the above mentioned pharmaceutically acceptable excipients, it may be desirable to add other pharmaceutically acceptable excipients to the pharmaceutical composition to improve particulate rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients may be used to provide structure and form to the particulate compositions (e.g., latex particles). In this regard, it will be appreciated that the rigidifying components can be removed using a post-production technique such as selective solvent extraction.

The pharmaceutical compositions may also include mixtures of pharmaceutically acceptable excipients. For instance, mixtures of carbohydrates and amino acids are within the scope of the present invention.

The compositions of one or more embodiments of the present invention may take various forms, such as dry powders, capsules, tablets, reconstituted powders, suspensions, or dispersions comprising a non-aqueous phase, such as propellants (e.g., chlorofluorocarbon, hydrofluoroalkane). The moisture content of dry powder may be less than about 15 wt %, such as less than about 10 wt %, less than about 5 wt %, less than about 2 wt %, less than about 1 wt %, or less than about 0.5 wt %. Such powders are described in WO 95/24183, WO 96/32149, WO 99/16419, WO 99/16420, and WO 99/16422, which are incorporated herein by reference in their entireties.

One or more embodiments of the invention involve homogeneous compositions of amphotericin B incorporated in a matrix material with little, if any, unincorporated amphotericin B particles. For instance, at least about 40 wt %, at least about 50 wt %, at least about 60 wt %, at least about 70%, at least about 80%, at least about 90 wt %, at least about 95 wt %, or at least about 99 wt %, of the composition may comprise particulates including both amphotericin B and matrix material.

In some cases, however, a heterogeneous composition may be desirable in order to provide a desired pharmacokinetic profile of the amphotericin B to be administered, and in these cases, a large amphotericin B particle (e.g., mass median diameter of about 3 μm to about 10 μm, or larger) may be used.

Homogeneous compositions may comprise small amphotericin B particles. Amphotericin B particles having a mass median diameter less than about 3 μm, as discussed above, can be dispersible and can facilitate production of homogenous compositions of amphotericin B incorporated into matrix material. It has been discovered that if the amphotericin B mass median diameter is greater than about 3 μm, the result may be a heterogeneous composition comprising amphotericin B incorporated in the matrix material and particles comprising amphotericin B without any matrix material. These heterogeneous compositions often exhibit poor powder flow and dispersibility, which may result in dose variation. Compositions made from larger amphotericin B particles have also resulted in toxicity in rats. It should be noted, however, that heterogeneous distribution may be ameliorated via atomization processes, which can afford homogeneous distribution for larger amphotericin B particles.

In view of the above, in some versions, the pharmaceutical composition has high homogeneity, the amphotericin B has a high crystallinity level, and the size of amphotericin B particles forming the composition is small. The degree of homogeneity, the crystallinity level, and the particle size may be any of those discussed above. For instance, in one version, the crystallinity level is at least about 50%, and the mass median diameter is less than about 3 μm. In another version, the crystallinity level is at least about 70%, and the mass median diameter is less than about 2.8 μm. In still another version, the crystallinity level is at least about 80%, and the mass median diameter is less than about 2.6 μm. In yet another version, the crystallinity level is at least about 90%, and the mass median diameter is less than about 2.4 μm.

In some cases, however, the degree of homogeneity is high, and one or more of the crystallinity level and amphotericin B are outside the ranges discussed above. Alternatively, in some cases, the degree of homogeneity is low, and one or more of the crystallinity level and amphotericin B are within the ranges discussed above.

In one version, the pharmaceutical composition comprises amphotericin B incorporated into a phospholipid matrix. The pharmaceutical composition may comprise phospholipid matrices that incorporate the active agent and that are in the form of particulates that are hollow and/or porous microstructures, as described in the aforementioned WO 99/16419, WO 99/16420, WO 99/16422, WO 01/85136, and WO 01/85137, which are incorporated herein by reference in their entireties. The hollow and/or porous microstructures are useful in delivering the amphotericin B to the lungs because the density, size, and aerodynamic qualities of the hollow and/or porous microstructures facilitate transport into the deep lungs during a user's inhalation, In addition, the phospholipid-based hollow and/or porous microstructures reduce the attraction forces between particulates, making the pharmaceutical composition easier to deagglomerate during aerosolization and improving the flow properties of the pharmaceutical composition making it easier to process.

In one version, the pharmaceutical composition is composed of hollow and/or porous microstructures having a bulk density less than about 1.0 g/cm$^3$, less than about 0.5 g/cm$^3$, less than about 0.3 g/cm$^3$, less than about 0.2 g/cm$^3$, or less than about 0.1 g/cm$^3$. By providing low bulk density particles or particulates, the minimum powder mass that can be filled into a unit dose container is reduced, which eliminates the need for carrier particles. That is, the relatively low density of the powders of one or more embodiments of the present invention provides for the reproducible administration of relatively low dose pharmaceutical compounds. Moreover, the elimination of carrier particles will potentially reduce throat deposition and any "gag" effect or coughing, since large carrier particles, e.g., lactose particles, will impact the throat and upper airways due to their size.

In one version, the pharmaceutical composition is in dry powder form and is contained within a unit dose receptacle which may be inserted into or near the aerosolization apparatus to aerosolize the unit dose of the pharmaceutical composition. This version is useful in that the dry powder form may be stably stored in its unit dose receptacle for a long period of time. In some examples, pharmaceutical compositions of one or more embodiments of the present invention have been stable for at least about 2 years. In some versions, no refrigeration is required to obtain stability. In other versions, reduced temperatures, e.g., at 2-8° C., may be used to prolong stable storage. In many versions, the storage stability allows aerosolization with an external power source.

It will be appreciated that the pharmaceutical compositions disclosed herein may comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, some embodiments comprise approximately spherical shapes. However, collapsed, deformed or fractured particulates are also compatible.

In one version, the amphotericin B is incorporated in a matrix that forms a discrete particulate, and the pharmaceutical composition comprises a plurality of the discrete particulates. The discrete particulates may be sized so that they are effectively administered and/or so that they are available where needed. For example, for an aerosolizable pharmaceutical composition, the particulates are of a size that allows the particulates to be aerosolized and delivered to a user's respiratory tract during the user's inhalation.

In some versions, the pharmaceutical composition comprises particulates having a mass median diameter less than about 20 μm, such as less than about 10 μm, less than about 7 µm, or less than about 5 µm. The particulates may have a mass median aerodynamic diameter ranging from about 1 µm to about 6 µm, such as about 1.5 µm to about 5 µm, or about 2 µm to about 4 µm. If the particulates are too large, toxicity in rats has been observed. If the particulates are too small, a larger percentage of the particulates may be exhaled.

In view of the above, in some versions, the pharmaceutical composition comprises particulates having a small mass median aerodynamic diameter, the pharmaceutical composition has high homogeneity, the amphotericin B has a high crystallinity level, and the size of amphotericin B particles forming the pharmaceutical composition is small. The mass median aerodynamic diameter, degree of homogeneity, crystallinity level, and amphotericin B particle size may be any of those discussed above. For instance, in one version, the mass median aerodynamic diameter is less than about 20 µm, at least about 60 wt % of the pharmaceutical composition comprise both amphotericin B and matrix material, the crystallinity level is at least about 50%, and the mass median diameter is less than about 3 µm. In another version, the mass median aerodynamic diameter is less than about 10 µm, at least about 70 wt % of the pharmaceutical composition comprise both amphotericin B and matrix material, the crystallinity level is at least about 70%, and the mass median diameter is less than about 2.8 µm. In still another version, the mass median aerodynamic diameter is less than about 7 µm, at least about 80 wt % of the pharmaceutical composition comprise both amphotericin B and matrix material, the crystallinity level is at least about 80%, and the mass median diameter is less than about 2.6 µm. In yet another version, the mass median aerodynamic diameter is less than about 7 µm, at least about 90 wt % of the pharmaceutical composition comprise both amphotericin B and matrix material, the crystallinity level is at least about 90%, and the mass median diameter is less than about 2.4 µm.

In some cases, however, the mass median aerodynamic diameter is small and one or more of the homogeneity, crystallinity level, and amphotericin B particle size are outside the ranges discussed above. Similarly, in other cases, the mass median aerodynamic diameter is large and one or more of the homogeneity, crystallinity level, and amphotericin B particle size are within the ranges discussed above.

In view of the above, the toxicity of inhaled amphotericin B particulates or particles in rats is dependent on several factors. While not wishing to be bound by theory, these factors appear to include, but are not limited to, amphotericin B crystallinity level, amphotericin B particle size used to make inhaled particles or particulates, homogeneity of inhaled particulates, and size of inhaled particles or particulates.

The matrix material may comprise a hydrophobic or a partially hydrophobic material. For example, the matrix material may comprise a lipid, such as a phospholipid, and/or a hydrophobic amino acid, such as leucine or trileucine. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; and 6,503,480, and in copending and co-owned U.S. application Ser. No. 10/750,934, filed on Dec. 31, 2003, all of which are incorporated herein by reference in their entireties. Examples of hydrophobic amino acid matrices are described in U.S. Pat. Nos. 6,372,258 and 6,358,530, and in U.S. application Ser. No. 10/032,239, filed on Dec. 21, 2001, which are incorporated herein by reference in their entireties.

When phospholipids are utilized as the matrix material, the pharmaceutical composition may also comprise a polyvalent cation, as disclosed in WO 01/85136 and WO 01/85137, which are incorporated herein by reference in their entireties.

According to another embodiment, release kinetics of the active agent(s) containing composition is controlled. According to one or more embodiments, the compositions of the present invention provide immediate release of the active agent(s). Alternatively, the compositions of other embodiments of the present invention may be provided as non-homogeneous mixtures of active agent incorporated into a matrix material and unincorporated active agent in order to provide desirable release rates of antifungal agent. According to this embodiment, antifungal agents formulated using the emulsion-based manufacturing process of one or more embodiments of the present invention have utility in immediate release applications when administered to the respiratory tract. Rapid release is facilitated by: (a) the high specific surface area of the low density porous powders; (b) the small size of the drug crystals that are incorporated therein, and; (c) the low surface energy of the particulates.

Alternatively, it may be desirable to engineer the particulate matrix so that extended release of the active agent(s) is effected. This may be particularly desirable when the active agent(s) is rapidly cleared from the lungs or when sustained release is desired. For example, the nature of the phase behavior of phospholipid molecules is influenced by the nature of their chemical structure and/or preparation methods in spray-drying feedstock and drying conditions and other composition components utilized. In the case of spray-drying of active agent(s) solubilized within a small unilamellar vesicle (SUV) or multilamellar vesicle (MLV), the active agent(s) are encapsulated within multiple bilayers and are released over an extended time.

In contrast, spray-drying of a feedstock comprised of emulsion droplets and dispersed or dissolved active agent(s) in accordance with the teachings herein leads to a phospholipid matrix with less long-range order, thereby facilitating rapid release. While not being bound to any particular theory, it is believed that this is due in part to the fact that the active agent(s) are never formally encapsulated in the phospholipid, and the fact that the phospholipid is initially present on the surface of the emulsion droplets as a monolayer (not a bilayer as in the case of liposomes). The spray-dried particulates prepared by the emulsion-based manufacturing process of one or more embodiments of the present invention often have a high degree of disorder. Also, the spray-dried particulates typically have low surface energies, where values as low as 20 mN/m have been observed for spray-dried DSPC particulates (determined by inverse gas chromatography). Small angle X-ray scattering (SAXS) studies conducted with spray-dried phospholipid particulates have also shown a high degree of disorder for the lipid, with scattering peaks smeared out, and length scales extending in some instances only beyond a few nearest neighbors.

It should be noted that a matrix having a high gel to liquid crystal phase transition temperature is not sufficient in itself to achieve sustained release of the active agent(s). Having sufficient order for the bilayer structures is also important for achieving sustained release. To facilitate rapid release, an emulsion-system of high porosity (high surface area), and minimal interaction between the drug substance and phospholipid may be used. The pharmaceutical composition formation process may also include the additions of other composition components (e.g., small polymers such as Pluronic F-68; carbohydrates, salts, hydrotropes) to break the bilayer structure are also contemplated.

To achieve a sustained release, incorporation of the phospholipid in bilayer form may be used, especially if the active agent is encapsulated therein. In this case increasing the $T_m$ of the phospholipid may provide benefit via incorporation of divalent counterions or cholesterol. As well, increasing the interaction between the phospholipid and drug substance via the formation of ion-pairs (negatively charged active+steaylamine, positively charged active+phosphatidylglycerol) would tend to decrease the dissolution rate. If the active is amphiphilic, surfactant/surfactant interactions may also slow active dissolution.

The addition of divalent counterions (e.g., calcium or magnesium ions) to long-chain saturated phosphatidylcholines results in an interaction between the negatively charged phosphate portion of the zwitterionic headgroup and the positively charged metal ion. This results in a displacement of water of hydration and a condensation of the packing of the phospholipid lipid headgroup and acyl chains. Further, this results in an increase in the Tm of the phospholipid. The decrease in headgroup hydration can have profound effects on the spreading properties of spray-dried phospholipid particulates on contact with water. A fully hydrated phosphatidylcholine molecule will diffuse very slowly to a dispersed crystal via molecular diffusion through the water phase. The process is exceedingly slow because the solubility of the phospholipid in water is very low (about $10^{-10}$ mol/L for DPPC). Prior art attempts to overcome this phenomenon include homogenizing the crystals in the presence of the phospholipid. In this case, the high degree of shear and radius of curvature of the homogenized crystals facilitates coating of the phospholipid on the crystals. In contrast, "dry" phospholipid powders according to one or more embodiments of this invention can spread rapidly when contacted with an aqueous phase, thereby coating dispersed crystals without the need to apply high energies.

For example, upon reconstitution, the surface tension of spray-dried DSPC/Ca mixtures at the air/water interface decreases to equilibrium values (about 20 mN/m) as fast as a measurement can be taken. In contrast, liposomes of DSPC decrease the surface tension (about 50 mN/m) very little over a period of hours, and it is likely that this reduction is due to the presence of hydrolysis degradation products such as free fatty acids in the phospholipid. Single-tailed fatty acids can diffuse much more rapidly to the air/water interface than can the hydrophobic parent compound. Hence the addition of calcium ions to phosphatidylcholines can facilitate the rapid encapsulation of crystalline drugs more rapidly and with lower applied energy.

In another version, the pharmaceutical composition comprises low density particulates achieved by co-spray-drying nanocrystals with a perfluorocarbon-in-water emulsion. The nanocrystals may be formed by precipitation and may, e.g., range in size from about 45 μm to about 80 μm. Examples of perfluorocarbons include, but are not limited to, perfluorohexane, perfluorooctyl bromide, perfluorooctyl ethane, perfluorodecalin, perfluorobutyl ethane.

In accordance with the teachings herein the particulate compositions will preferably be provided in a "dry" state. That is, in one or more embodiments, the particulates will possess a moisture content that allows the powder to remain chemically and physically stable during storage at ambient or reduced temperature and remain dispersible. In this regard, there is little or no change in primary particulate size, content, purity, and aerodynamic particulate size distribution.

As such, the moisture content of the particulates is typically less than about 10 wt %, such as less than about 6 wt %, less than about 3 wt %, or less than about 1 wt %. The moisture content is, at least in part, dictated by the composition and is controlled by the process conditions employed, e.g., inlet temperature, feed concentration, pump rate, and blowing agent type, concentration and post drying. Reduction in bound water leads to significant improvements in the dispersibility and flowability of phospholipid based powders, leading to the potential for highly efficient delivery of powdered lung surfactants or particulate composition comprising active agent dispersed in the phospholipid. The improved dispersibility allows simple passive DPI devices to be used to effectively deliver these powders.

Yet another version of the pharmaceutical composition includes particulate compositions that may comprise, or may be partially or completely coated with, charged species that prolong residence time at the point of contact or enhance penetration through mucosae. For example, anionic charges are known to favor mucoadhesion while cationic charges may be used to associate the formed particulate with negatively charged bioactive agents such as genetic material. The charges may be imparted through the association or incorporation of polyanionic or polycationic materials such as polyacrylic acids, polylysine, polylactic acid, and chitosan.

These unit dose pharmaceutical compositions may be contained in a container. Examples of containers include, but are not limited to, capsules, blisters, vials, ampoules, or container closure systems made of metal, polymer (e.g., plastic, elastomer), glass, or the like.

The container may be inserted into an aerosolization device. The container may be of a suitable shape, size, and material to contain the pharmaceutical composition and to provide the pharmaceutical composition in a usable condition. For example, the capsule or blister may comprise a wall which comprises a material that does not adversely react with the pharmaceutical composition. In addition, the wall may comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion may be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

In one version, the pharmaceutical composition comprising crystalline amphotericin B is aerosolizable so that it may be delivered to the lungs of a patient during the patient's inhalation. In this way the amphotericin B in the pharmaceutical composition is delivered directly to the site of infection. This is advantageous over systemic administration. Because the active agent(s) often have renal or other toxicity, minimizing systemic exposure is typically preferred. Therefore, the amount of active agent(s) that may be delivered to the lungs is preferably limited to the minimum pharmacologically effective dose. By administering the active agent(s) directly to the lungs, a greater amount may be delivered to the site in need of the therapy while significantly reducing systemic exposure. Furthermore, by predominantly delivering amphotericin B in its crystalline form, the desired concentration of amphotericin B can be maintained at the site of infection over a period of time with a reduced likelihood of the generation of a toxic effect within the lungs.

The pharmaceutical compositions of one or more embodiments of the present invention lack taste. In this regard, although taste masking agents are optionally included within the composition, the compositions often lack taste even without a taste masking agent.

The particles, particulates, and compositions of one or more embodiments of the present invention may be made by any of the various methods and techniques known and available to those skilled in the art.

As noted above, the crystallinity level of the amphotericin B affects performance. A skilled artisan would be able to adjust the crystallinity level of the amphotericin B by adjusting crystallization conditions. For instance, the crystallinity level may be adjusted by varying the solvent, amphotericin B concentration, pH, rate of pH adjustment, purity level, temperature, cooling/heating rate, annealing time, use of seed crystals, solvent addition rate, agitation rate, cosolvent type/concentration, and holding period used during crystallization.

Alternatively, the crystallinity level may be adjusted through recrystallization. Recrystallization techniques are known in the art. Exemplary recrystallization techniques are described as follows.

During recrystallization processes, the amphotericin B is preferably protected from light. Amphotericin B may be dissolved in a solvent. Examples of solvents include solvent systems, such as one including methanol, dimethylformamide, and citric acid monohydrate. Once the solids are essentially dissolved, the solution is optionally filtered.

After filtration, an additional solvent, e.g., methylene chloride, may be added to the filtrate. Chilled water may then be added with stirring.

Precipitation of amphotericin B may be achieved through pH adjustment of the solution, e.g., to pH~7, by adding a base, such as triethanolamine. While not wishing to be bound by theory, the rate of precipitation affects the level of crystallinity. Slower precipitation generally results in higher crystallinity.

Thus, to obtain more amorphous amphotericin B, the base may be added quickly, e.g., in a single pour with stirring. The resulting relatively amorphous amphotericin B may then be isolated. For example, amorphous amphotericin B may be isolated through centrifugation of the slurry followed by decantation of the supernatant. The product may be washed by resuspension of the cake in, e.g., chilled methanol, followed by centrifugation and decantation. The washing process may be repeated or may involve additional washing steps, e.g., using acetone at room temperature.

To obtain more crystalline amphotericin B, the base may be added slowly, e.g., dropwise with stirring. The resulting slurry may then be heated, e.g., 44-46° C. for 90 minutes followed by cooling, e.g., to room temperature for 30 minutes and then to 2-8° C. for 60 minutes. The crystalline form may then be ready for isolation. For example, the crystalline form of amphotericin B may be captured by vacuum filtration. The product may be washed, e.g., by using chilled 40% methanol followed by acetone at room temperature.

Once the amphotericin B is isolated and washed, it may be dried. For example, the amphotericin B may be vacuum dried, e.g., for 1 to 3 days at room temperature with the product protected from light. Optionally, during the drying process, larger aggregates may be broken, e.g., by using a spatula, to facilitate evaporation of residual solvents.

As noted above, smaller amphotericin B particle sizes are often desirable. In many instances, the amphotericin B in bulk form has a mass median diameter greater than about 3.0 µm, and in many cases greater than about 10 µm. Accordingly, in one or more embodiments of the invention, the bulk amphotericin B is subjected to a size reduction process to reduce the mass median diameter to below about 3 µm prior to use. Suitable size reduction processes are known in the art and include supercritical fluid processing methods such as disclosed in WO 95/01221, WO 96/00610, and WO 98/36825, which are incorporated herein by reference in their entireties, cryogenic milling, wet milling, ultrasound, high pressure homogenization, microfluidization, crystallization processes, and in processes disclosed in U.S. Pat. No. 5,858,410, which is incorporated herein by reference in its entirety.

In one or more embodiments of the invention, a method of making a pharmaceutical composition comprises providing particles of amphotericin B as a starting material, wherein at least about 50% of the amphotericin B is in crystalline form. In other versions, at least about 60%, at least about 70%, at least about 80%, at least about 90%, at least about 95%, or at least about 99%, of the amphotericin B is in crystalline form. Amphotericin B particles of the starting material may be suspended in a liquid feedstock optionally comprising one or more pharmaceutically acceptable excipients. The suspension feedstock is then dried, such as by spray drying, to produce particulates comprising crystalline amphotericin B and the one or more pharmaceutically acceptable excipients. In one version, in the produced particulates comprising amphotericin B, at least about 70% of the amphotericin B in the produced particulates is in crystalline form. In other versions, at least about 80%, at least about 85%, at least about 90%, at least about 95%, or at least about 99% of the amphotericin B in the produced particulates is in crystalline form.

In one version, the crystallinity level of the starting material of the amphotericin B particles is determined. For example, before introduction into the feedstock, the X-ray powder diffraction pattern of the material may be measured. From these data, the crystallinity level may be determined. Alternatively, infrared spectroscopy, Raman spectroscopy, dynamic vapor sorption, heat of solution calorimetry, or isothermal microcalorimetry may alternatively be used to determine the crystallinity level, as would be recognized by those skilled in the art. If the crystallinity level is above a predetermined amount, such as the percentages above, then the starting material is used. If the crystallinity level is below the predetermined amount, the starting material may, e.g., be discarded or recrystallized.

In other versions, the amorphicity of the amphotericin B is determined. Thus, in one version, a method of making a pharmaceutical composition comprises providing particles of amphotericin B as a starting material, wherein less than about 50% of the amphotericin B is in amorphous form. In other versions, less than about 40%, less than about 30%, less than about 20%, less than about 10%, less than about 5%, or less than about 1% of the amphotericin B is in amorphous form. Amphotericin B particles of the starting material may be suspended in a liquid feedstock optionally comprising one or more pharmaceutically acceptable excipients. The suspension feedstock is then dried, such as by spray drying, to produce particulates comprising amphotericin B and the one or more pharmaceutically acceptable excipients. In one version, in the produced particulates comprising amphotericin B, at least about 70% of the amphotericin B in the produced particulates is in crystalline form. In other versions, at least about 80%, at least about 85%, at least about 90%, at least about 95%, or at least about 99% of the amphotericin B in the produced particulates is in crystalline form.

The amorphicity may be determined using known techniques. For example, the amorphicity may be determined using infrared spectroscopy, Raman spectroscopy, dynamic vapor sorption, differential scanning calorimetry, and the like. If the amorphicity is below a predetermined amount, such as the percentages above, then the starting material is used. If the amorphicity is above the predetermined amount, the starting material may be discarded or recrystallized.

In still another version, a recrystallization process may be performed as part of the preparation process instead of or in addition to the determination of the crystallinity level. The recrystallization process may be performed by dissolving the amphotericin B in a suitable solvent, such as ethanol or other polar solvent, and slowly drying the solution to generate crystalline amphotericin B or causing the crystalline amphotericin B to precipitate out of the solution. In one version, a supercritical fluid may be used to simultaneously disperse and extract the crystalline material, as disclosed in WO 95/01221, WO 96/00610, and WO 98/36825, which are incorporated herein by reference in their entireties. In another version, a multi-zonal spray-drying process, as disclosed in WO 01/00312, which is incorporated herein by reference in its entirety, may be used to form the crystalline amphotericin B.

Another version involves determining the crystallinity level of the produced particles or particulates, which may comprise crystalline amphotericin B and, optionally, pharmaceutically acceptable excipient and/or other active ingredient(s). If the crystallinity level in the produced particles or particulates is above a predetermined percentage, such as above about 70%, above about 80%, above about 90%, above about 95%, or above about 99%, then the produced particles or particulates may be released for administration to a patient. If the crystallinity level is below the predetermined amount, then the produced particles or particulates may be discarded or reformulated.

The pharmaceutical composition may be produced using various known techniques. For example, the composition may be formed by spray drying, lyophilization, milling (e.g., wet milling, dry milling), and the like.

In spray drying, the preparation to be spray dried or feedstock can be any solution, coarse suspension, slurry, colloidal dispersion, or paste that may be atomized using the selected spray drying apparatus. In the case of insoluble agents, the feedstock may comprise a suspension as described above. Alternatively, a dilute solution and/or one or more solvents may be utilized in the feedstock. In one or more embodiments, the feed stock will comprise a colloidal system such as an emulsion, reverse emulsion, microemulsion, multiple emulsion, particle dispersion, or slurry.

In one version, the amphotericin B and the matrix material are added to an aqueous feedstock to form a feedstock solution, suspension, or emulsion. The feedstock is then spray dried to produce dried particulates comprising the matrix material and the crystalline amphotericin B. Suitable spray-drying processes are known in the art, for example as disclosed in WO 99/16419 and U.S. Pat. Nos. 6,077,543; 6,051,256; 6,001,336; 5,985,248; and 5,976,574, which are incorporated herein by reference in their entireties.

Whatever components are selected, the first step in particulate production typically comprises feedstock preparation. If a phospholipids-based particulate is intended to act as a carrier for the amphotericin B, the selected active agent(s) may be introduced into a liquid, such as water, to produce a concentrated suspension. The concentration of amphotericin B and optional active agents typically depends on the amount of agent required in the final powder and the performance of the delivery device employed (e.g., the fine particle dose for a metered dose inhaler (MDI) or a dry powder inhaler (DPI)).

Any additional active agent(s) may be incorporated in a single feedstock preparation and spray dried to provide a single pharmaceutical composition species comprising a plurality of active agents. Conversely, individual active agents could be added to separate stocks and spray dried separately to provide a plurality of pharmaceutical composition species with different compositions. These individual species could be added to the suspension medium or dry powder dispensing compartment in any desired proportion and placed in the aerosol delivery system as described below.

Polyvalent cation may be combined with the amphotericin B suspension, combined with the phospholipid emulsion, or combined with an oil-in-water emulsion formed in a separate vessel. The amphotericin B may also be dispersed directly in the emulsion.

For example, polyvalent cation and phospholipid may be homogenized in hot distilled water (e.g., 70° C.) using a suitable high shear mechanical mixer (e.g., Ultra-Turrax model T-25 mixer) at 8000 rpm for 2 to 5 min. Typically, 5 to 25 g of fluorocarbon is added dropwise to the dispersed surfactant solution while mixing. The resulting polyvalent cation-containing perfluorocarbon in water emulsion may then be processed using a high pressure homogenizer to reduce the particle size. Typically, the emulsion is processed for five discrete passes at 12,000 to 18,000 PSI and kept at about 50° C. to about 80° C.

When the polyvalent cation is combined with an oil-in-water emulsion, the dispersion stability and dispersibility of the spray dried pharmaceutical composition can be improved by using a blowing agent, as described in WO 99/16419, which is incorporated herein by reference in its entirety. This process forms an emulsion, optionally stabilized by an incorporated surfactant, typically comprising submicron droplets of water immiscible blowing agent dispersed in an aqueous continuous phase. The blowing agent may be a fluorinated compound (e.g. perfluorohexane, perfluorooctyl bromide, perfluorooctyl ethane, perfluorodecalin, perfluorobutyl ethane) which vaporizes during the spray-drying process, leaving behind generally hollow, porous aerodynamically light particulates. Other suitable liquid blowing agents include non-fluorinated oils, chloroform, Freon® fluorocarbons, ethyl acetate, alcohols, hydrocarbons, nitrogen, and carbon dioxide gases. The blowing agent may be emulsified with a phospholipid.

Although the pharmaceutical compositions may be formed using a blowing agent as described above, it will be appreciated that, in some instances, no additional blowing agent is required and an aqueous dispersion of the amphotericin B and/or pharmaceutically acceptable excipients and surfactant(s) are spray dried directly. In such cases, the pharmaceutical composition may possess certain physicochemical properties (e.g., high crystallinity, elevated melting temperature, surface activity, etc.) that make it particularly suitable for use in such techniques.

As needed, cosurfactants such as poloxamer 188 or span 80 may be dispersed into this annex solution. Additionally, pharmaceutically acceptable excipients such as sugars and starches can also be added.

The feedstock(s) may then be fed into a spray dryer. Typically, the feedstock is sprayed into a current of warm filtered air that evaporates the solvent and conveys the dried product to a collector. The spent air is then exhausted with the solvent. Commercial spray dryers manufactured by Büchi Ltd. or Niro Corp. may be modified for use to produce the pharmaceutical composition. Examples of spray drying methods and systems suitable for making the dry powders of one or more embodiments of the present invention are disclosed in U.S. Pat. Nos. 6,077,543; 6,051,256; 6,001,336; 5,985,248; and 5,976,574, which are incorporated herein by reference in their entireties.

Operating conditions of the spray dryer such as inlet and outlet temperature, feed rate, atomization pressure, flow rate of the drying air, and nozzle configuration can be adjusted in order to produce the required particulate size, and production yield of the resulting dry particulates. The selection of appropriate apparatus and processing conditions are within the purview of a skilled artisan in view of the teachings herein and may be accomplished without undue experimentation. Exemplary settings are as follows: an air inlet temperature between about 60° C. and about 170° C.; an air outlet between about 40° C. to about 120° C.; a feed rate between about 3 mL/min to about 15 mL/min; an aspiration air flow of about 300 L/min; and an atomization air flow rate between about 25/min and about 50 L/min. The settings will, of course, vary depending on the type of equipment used. In any event, the use of these and similar methods allow formation of aerodynamically light particulates with diameters appropriate for aerosol deposition into the lung.

Hollow and/or porous microstructures may be formed by spray drying, as disclosed in WO 99/16419, which is incorporated herein by reference. The spray-drying process can result in the formation of a pharmaceutical composition comprising particulates having a relatively thin porous wall defining a large internal void. The spray-drying process is also often advantageous over other processes in that the particulates formed are less likely to rupture during processing or during deagglomeration.

Pharmaceutical compositions useful in one or more embodiments of the present invention may alternatively be formed by lyophilization. Lyophilization is a freeze-drying process in which water is sublimed from the composition after it is frozen. The lyophilization process is often used because biologicals and pharmaceuticals that are relatively unstable in an aqueous solution may be dried without exposure to elevated temperatures, and then stored in a dry state where there are fewer stability problems. With respect to one or more embodiments of the instant invention, such techniques are particularly compatible with the incorporation of peptides, proteins, genetic material and other natural and synthetic macromolecules in pharmaceutical compositions without compromising physiological activity. Lyophilized cake containing a fine foam-like structure can be micronized using techniques known in the art to provide particulates of the desired size.

The compositions of one or more embodiments of the present invention may be administered by known techniques, such as inhalation, oral, intramuscular, intravenous, intratracheal, intraperitoneal, subcutaneous, and transdermal.

For example, the pharmaceutical compositions of one or more embodiments of the invention are effective in the treatment, including adjunctive treatment, of pulmonary and/or nasal fungal infections. Amphotericin B acts as an antifungal agent to treat a pulmonary and/or nasal fungal infection and/or to prevent the onset of a pulmonary and/or nasal fungal infection. It is believed that amphotericin B acts to slow down the growth and multiplication of susceptible fungi. If the concentrations of amphotericin B are sufficiently high, they can also destroy the fungi. Amphotericin B appears to act on the cell membrane of the fungi, altering the integrity of the cell membrane.

In one version, the compositions, when inhaled, penetrate into the nasal cavities and/or airways of the lungs to achieve effective amphotericin B concentrations, such as in the infected secretions and lung tissue, including the epithelial lining fluid, alveolar macrophages, and neutrophils. Moreover, the doses of composition that are inhaled are typically much less than those administered by other routes and required to obtain similar antifungal effects, due to the efficient targeting of the inhaled composition directly to the site of fungal infection.

In one or more embodiments of the invention, a pharmaceutical composition comprising amphotericin B, wherein a predominant amount of the amphotericin B is in crystalline form, is administered to the lungs of a patient in need thereof. For example, the patient may have been diagnosed with a pulmonary and/or nasal fungal infection or the patient may be determined to be susceptible to a pulmonary and/or nasal fungal infection. Examples of pulmonary and/or nasal fungal infections include aspergillosis, blastomycosis, disseminated candidiasis, coccidioidomycosis, cryptococcosis, histoplasmosis, mucormycosis, sporotrichosis, some infections caused by *Candida* spp, and others as known in the art.

Thus, the pharmaceutical compositions of one or more embodiments of the present invention can be used to treat and/or provide prophylaxis for a broad range of patients. A suitable patient for receiving treatment and/or prophylaxis as described herein is any mammalian patient in need thereof, preferably such mammal is a human. Examples of patients include, but are not limited to, pediatric patients, adult patients, and geriatric patients. The patients are typically at risk for obtaining a fungal infection.

In one version, the pharmaceutical compositions of one or more embodiments of the present invention are useful in the prophylaxis of pulmonary and/or nasal fungal infections, such as for immunocompromised patients, e.g., individuals undergoing chemotherapy or radiation therapy for cancer, organ transplant recipients, patients suffering from conditions that adversely affect the immune system, such as HIV, or any other condition which predisposes a patient to pulmonary and/or nasal fungal infections. The pharmaceutical compositions may also be used in the treatment of active pulmonary and/or nasal fungal infections, such as aspergillosis (most commonly due to *Aspergillus fumigatus, Aspergillus flavus, Aspergillus niger, Aspergillus nidulans*, and *Aspergillus terreus*), coccidioidomycosis, histoplasmosis, blastomycosis, and other fungal pathogens.

In one version, an aerosolizeable pharmaceutical composition comprising amphotericin B is administered to the lungs and/or nasal cavity of a patient in a manner that results in an amphotericin B concentration greater than a minimum inhibitory concentration (MIC) of the fungus. The MIC is defined as the lowest concentration of amphotericin B that inhibits fungal growth. The MIC may be expressed as a particular concentration value or as a range of concentrations. A method according to one or more embodiments of the present invention administers a sufficient amount of the pharmaceutical composition to achieve a target lung concentration of amphotericin B that falls within the range of MIC values or is above a particular MIC value. In another version, the target lung concentration of amphotericin B exceeds the MIC range. In another version, the target lung concentration of amphotericin B exceeds the lowest value in an MIC range. In another version, the target amphotericin B concentration is a concentration that exceeds the MIC range and is at least about 2 times, such as at least about 3 times, at least about 4 times, or at least about 5 times, the maximum of the MIC range. The target amphotericin B concentration may be a target lung concentration range. In one version, the target lung amphotericin B concentration range fluctuates above and below a value that is from about 2 to about 20 times the midrange value of the MIC range, such as about 3 to about 10 times the midrange value, or about 5 times the midrange value. In one version, the amphotericin B concentrations and the MIC determinations are based on the concentrations in the epithelial lining fluid. In another version, the amphotericin B concentrations and the MIC determinations are based on the concentrations in the solid lung tissue. As used herein, unless otherwise specified, the MIC value shall be taken to be the particular value when a particular MIC value is determined and shall be taken to be a midrange value when a range of MIC values is determined. MIC determinations may be made according to processes known in the art.

In one version, the pharmaceutical composition comprising amphotericin B is administered so that a target concentration is maintained over a desired period of time. For example, it has been determined that an administration routine that maintains a target concentration of amphotericin B that is at least about 2 times, such as at least about 3 times, the determined MIC value is effective in treating and/or providing prophylaxis against a pulmonary and/or nasal fungal infection. It has been further determined that by maintaining the amphotericin B concentration at the target lung concentration for a period of at least about 1 week, such as at least about 2 weeks, or at least about 3 weeks, a pulmonary and/or nasal fungal infection can be effectively treated in some patients. Additionally or alternatively, by maintaining the amphotericin B lung concentration at the target concentration for the above periods in an immunocompromised patient, the likelihood of the patient developing a pulmonary and/or nasal fungal infection can be reduced. In many cases, the period of treatment and/or the period of prophylaxis may be extended to be more than about 1 month, more than about 2 months, more than about 3 months (e.g., 17 weeks), more than about 4 months, or longer.

In one version, the method of administering the crystalline amphotericin B takes advantage of the lung retention properties of the pharmaceutical composition comprising amphotericin B. In this regard, one or more embodiments of the present invention involves the discovery that amphotericin B of the pharmaceutical compositions has an amphotericin B lung-residence half-life of (1) at least about 10 hours, such as at least about 15 hours or at least about 20 hours in lung epithelial fluid; as measured by bronchoalveolar lavage, and/or (2) at least about 1 week, such as at least about 2 weeks, in lung tissue, as measured by lung tissue homogenization.

Since the amphotericin B has a long lung-residence half-life and since low doses may be used in one or more embodiments, systemic exposure (blood/plasma amphotericin B concentrations) remains low enough to avoid renal and/or hepatic toxicity. For instance, after a 5 mg dose of inhaled amphotericin B, the blood level of the amphotericin B can remain less than about 1000 ng/mL, such as less than about 750 ng/mL, less than about 500 ng/mL, less than about 250 ng/mL, less than about 100 ng/mL, less than about 80 ng/mL, less than about 60 ng/mL, or less than about 40 ng/mL.

In view of the long residence half-life, once the target lung tissue amphotericin B concentration is reached, limited dosing is required to maintain the lung tissue amphotericin B concentration. For example, the pharmaceutical composition may be administered once per week in order to maintain the lung amphotericin B concentration within the target.

The dosage necessary and the frequency of dosing for maintaining the amphotericin B concentration within the target concentration depends on the composition and concentration of the amphotericin B within the composition. In each of the administration regimens, the dosages and frequencies are determined to give a lung amphotericin B concentration that is maintained within a certain target range. In one version, the amphotericin B may be administered weekly. In this version, the weekly dosage of amphotericin B ranges from about 2 mg to about 75 mg, such as about 2 mg to about 50 mg, about 4 mg to about 25 mg, about 5 mg to about 20 mg, and about 7 mg to about 10 mg.

The dose may be administered during a single inhalation or may be administered during several inhalations. The fluctuations of lung amphotericin B concentration can be reduced by administering the pharmaceutical composition more often or may be increased by administering the pharmaceutical composition less often. Therefore, the pharmaceutical composition of one or more embodiments of the present invention may be administered from about three times daily to about once a month, such as about once daily to about once every two weeks, about once every two days to about once a week, and about once per week.

In one version, the pharmaceutical composition is administered prophylactically to a patient who is likely to become immunocompromised. For example, a patient who will undergo drug immunosuppressive therapy, such as a patient expecting a bone marrow transplant, can be prophylactically treated with a pharmaceutical composition comprising crystalline amphotericin B to reduce the likelihood of developing a fungal infection during an immunocompromised risk period. In this version, the amphotericin B administration is initiated a sufficient amount of time before the patient is immunocompromised to allow the lung amphotericin B concentration to reach the target concentration on or before the time of immunocompromise. When a dose is administered once weekly, the prophylactic period may vary from about 1 week to about 20 weeks, depending on the composition and dosage. However, in one or more embodiments of the invention, the time to effective prophylactic amphotericin B concentrations is shortened by either providing high doses of amphotericin B during the initial prophylactic period and/or by more frequently administering the dosages during the initial prophylactic period (e.g., loading dose). In this version, additional doses are administered during the first week of therapy. For example, doses may be administered on Days 1, 2, 3, and 4 (or 4 doses on Day 1) and then on every seventh day thereafter. This early loading allows the target lung amphotericin B concentrations to be achieved much sooner. Accordingly, the time for attaining effective prophylaxis is reduced and a patient may begin his or her immunocompromised period sooner. In the some examples, a patient may become immunocompromised after 1-4 days, with a significantly reduced likelihood of developing a pulmonary and/or nasal fungal infection. Additionally or alternatively, the dosage administered during the pre-immunosuppression period may be higher than the dosage administered to maintain the target lung amphotericin B concentration (e.g., loading dose). For example, in one version, the first dose may be at least about two times the steady-state dosage given once the target lung amphotericin B concentration has been achieved.

Thus, in one version, the amphotericin B is administered as a loading dose followed by maintenance doses. The loading dose of amphotericin may range, e.g., from about 5 mg to about 75 mg, such as from about 10 mg to about 50 mg, from about 15 mg to about 40 mg, or from about 20 mg to about 30 mg, such as about 25 mg. The maintenance doses may be administered on a regular basis, e.g., weekly, after the loading dose. The maintenance dose typically ranges from about 2 mg to about 20 mg, such as from about 3 mg to about 15 mg or from about 4 mg to about 10 mg, such as about 5 mg.

The early loading may also be desirable when treating a patient who has been diagnosed with a pulmonary and/or nasal fungal infection. By early loading, the target lung amphotericin B concentration is achieved sooner than when no early loading is administered. Therefore, the treatment of the pulmonary and/or nasal fungal infection may be more rapidly initiated or provided.

In one specific therapeutic method, prophylaxis of pulmonary and/or nasal fungal infections is provided for a patient undergoing immunosuppressive therapy. According to this version, the patient is administered at least about 5 mg, such as from about 5 mg to about 10 mg, of aerosolized amphotericin B during the patient's inhalation at least about two times per week during an initial period. The aerosolized amphotericin B can be administered at least about three times per week during the initial period. In one version, the initial period may last from about one week to about three weeks. Following the initial period, the patient is administered the same dosage less frequently. For example, the aerosolized amphotericin B may be administered once every two weeks, and more preferably once per week. Following the initial period or near the end of the initial period, the immunosuppressive therapy can be initiated. The second period of administration is continued so that the target lung amphotericin B concentration is maintained at least through the immunocompromised risk period and longer if needed or if a pulmonary and/or nasal fungal infection develops. Additionally or alternatively, the dosage administered during the first period may be larger than the dosage administered during the second period. For example, during the first period, from about 10 mg to about 20 mg of amphotericin B may be administered and a lesser amount, such as from about 5 mg to about 10 mg, is administered during the second period. Optionally, a third dosing period may be provided where the dosage is administered less frequently and/or in a lesser amount than in the second period. The third dosing period may be initiated near the end of an immunocompromised period, such as by being initiated when the immunosuppressive therapy is terminated or reduced in severity.

In one version, the amphotericin B concentration is maintained for a period of time at a concentration above a determined minimum inhibitory concentration, such as described in U.S. application Ser. No. 10/751,342, filed on Dec. 31, 2003, which is incorporated herein by reference in its entirety. The lung amphotericin B concentration may either be the amphotericin B concentration in the epithelial lining or the amphotericin B concentration in solid lung tissue, and is preferably the latter. In some versions, the lung amphotericin B concentration is at least about 4 µg/g, such as at least about 9 µg/g, and may range from about 4.5 µg/g to about 20 µg/g, such as about 9 µg/g to about 15 µg/g.

For prophylaxis, the amount per dose of amphotericin B may be an amount that is effective to prevent pulmonary and/or nasal infection by a fungus and generally ranges from about 0.01 mg/kg to about 5.0 mg/kg, such as about 0.4 mg/kg to about 4.0 mg/kg, or about 0.7 mg/kg to about 3.0 mg/kg.

The pharmaceutical composition may be administered to a patient in any regimen which is effective to prevent pulmonary infection by a fungus. Illustrative prophylactic regimes include administering an antifungal dry powder as described herein 1 to 21 times per week over a time course from 1 to 6 weeks, followed, if needed, thereafter by administration once or twice weekly.

An example of an embodiment of the present invention for administration of aerosolized predominantly crystalline amphotericin B is shown in FIG. 1, which shows prophylactic loading. The MIC value for amphotericin B in this version has been determined to range from about 0.5 µg/g to about 4 µg/g, as shown by block 300. The midrange MIC value 300' is about 2.25 µg/g. The curve 301 shows a predicted lung amphotericin B concentration according to a particular administration regimen. As can be seen, the amphotericin B concentration reaches a target lung amphotericin B concentration range 302 that is above the MIC range 300 and is at least two times greater than the midrange MIC value 300'. The target lung amphotericin B concentration range 302 may in this version range from 4 μg/g to 50 μg/g, more preferably from 4.5 μg/g to 20 μg/g. In the specific version shown, the target lung amphotericin B concentration range 302 is a range from 9 μg/g to 15 μg/g, and fluctuates about a concentration value that is about five times the midpoint value 300' of the MIC range 300.

The maintenance of the lung amphotericin B concentration within a target lung amphotericin B concentration range according to one or more embodiments of the present invention is advantageous in its effectiveness in treating and/or providing prophylaxis against fungal infections and is also safer than conventional treatment. FIG. 2 shows the resulting predicted plasma amphotericin B concentration 400 during administration of amphotericin B according to one or more embodiments of the invention. As can be seen, the amphotericin B concentrations are significantly less than the plasma amphotericin B concentration minimum toxicity concentrations 401, thereby increasing the safety of the administration.

For treating a patient suffering from a pulmonary and/or nasal fungal infection, the amount per dose of amphotericin B administered may be an amount that is effective to treat the infection. The amount of amphotericin B for the treatment of infection will generally be higher than that used for prevention, and will typically range from about 0.01 mg/kg to 7.0 mg/kg, such as from about 0.2 mg/kg to about 6.0 mg/kg, or from about 0.8 mg/kg to about 5.0 mg/kg. In one exemplary treatment regimen, an antifungal powder in accordance with one or more embodiments of the invention may be administered about 1 to about 8 times daily, preferably from about 2 to about 6 times daily, over a course of from about 7 to about 28 days.

In treating these respiratory fungal conditions, the pharmaceutical compositions are typically administered in doses that are about 3 to about 10 or more times the MIC of the causative fungal pathogens. Generally, the dose of amphotericin B delivered to a patient will range from about 2 mg to about 400 mg daily, such as from about 10 mg to 200 mg daily, depending on the condition being treated, the age and weight of the patient, and the like.

While not wishing to be bound by theory, by providing the amphotericin B in accordance with one or more embodiments of the invention, the local toxicity of the amphotericin B can be reduced by decreasing the rate of dissolution of the amphotericin B and/or by increasing deposition throughout the lung and avoiding local toxicity in the upper lung. Thus, the administration of crystalline amphotericin B is believed to be safer than the administration of a predominantly amorphous form of amphotericin B. Furthermore, the administration of smaller inhaled particulates formed from smaller amphotericin B particles tends to improve safety.

When larger doses are administered, safety becomes a more important issue. Thus, higher crystallinity amphotericin B, smaller amphotericin B particle size, and smaller inhaled particle or particulate sizes are suggested for higher doses. For instance, for a dose of greater than 50 mg, a skilled artisan may want to use a composition in which the amphotericin B crystallinity level is at least about 90%, the amphotericin B mass median diameter is less than about 2.8 µm, and the inhaled particle or particulate has an MMAD of less than about 2.8 µm.

When solid particles or particulates comprising amphotericin B are administered to the lungs, it has been determined that it is desirable to control the rate of dissolution of the solid particles or particulates within the lungs. When the rate of dissolution is undesirably high, soluble, supermolecular aggregates form at local sites within the lungs. These soluble aggregates may in some instances be toxic to the lung tissue. However, when the rate of dissolution is sufficiently low, there is a lower likelihood that soluble toxic aggregates will develop. While not wishing to be bound by theory, it is believed that providing the solid particles or particulates comprising crystalline amphotericin B lowers the rate of dissolution when compared to amphotericin B in its amorphous form. Furthermore, it has been discovered that the lung amphotericin B concentrations in its crystalline form may be maintained at concentrations that are sufficiently high to provide a therapeutic effect against pulmonary and/or nasal fungal infections while significantly decreasing or preventing the development of toxic soluble aggregates.

Thus, in one version, the pharmaceutical composition may be delivered to the lungs of a patient in the form of a dry powder. Accordingly, the pharmaceutical composition comprises a dry powder that may be effectively delivered to the deep lungs or to another target site. This pharmaceutical composition is in the form of a dry powder comprising particles or particulates having a size selected to permit penetration into the alveoli of the lungs.

In some instances, it is desirable to deliver a unit dose, such as doses of 5 mg or 10 mg or greater of amphotericin B to the lung in a single inhalation. The above described phospholipid hollow and/or porous dry powder particulates allow for doses of about 5 mg or greater, often greater than about 10 mg, and sometimes greater than about 25 mg, to be delivered in a single inhalation and in an advantageous manner. Alternatively, a dosage may be delivered over two or more inhalations. For example, a 10 mg dosage may be delivered by providing two unit doses of 5 mg each, and the two unit doses may be separately inhaled.

The dispersions or powder pharmaceutical compositions may be administered using an aerosolization device. The aerosolization device may be a nebulizer, a metered dose inhaler, a liquid dose instillation device, or a dry powder inhaler. The powder pharmaceutical composition may be delivered by a nebulizer as described in WO 99/16420, by a metered dose inhaler as described in WO 99/16422, by a liquid dose instillation apparatus as described in WO 99/16421, and by a dry powder inhaler as described in U.S. patent application Ser. No. 09/888,311 filed on Jun. 22, 2001, in WO 99/16419, in WO 02/83220, in U.S. Pat. No. 6,546,929, and in U.S. patent application Ser. No. 10/616,448, filed on Jul. 8, 2003, which are incorporated herein by reference in their entireties. As such, an inhaler may comprise a canister containing the particles or particulates and propellant, and wherein the inhaler comprises a metering valve in communication with an interior of the canister. The propellant may be a hydrofluoroalkane.

The pharmaceutical composition of one or more embodiments of the present invention typically has improved emitted dose efficiency. Accordingly, high doses of the pharmaceutical composition may be delivered using a variety of aerosolization devices and techniques.

The emitted dose (ED) of these powders may be greater than about 30%, such as greater than about 40%, greater than about 50%, greater than about 60%, or greater than about 70%.

Figure 3A:
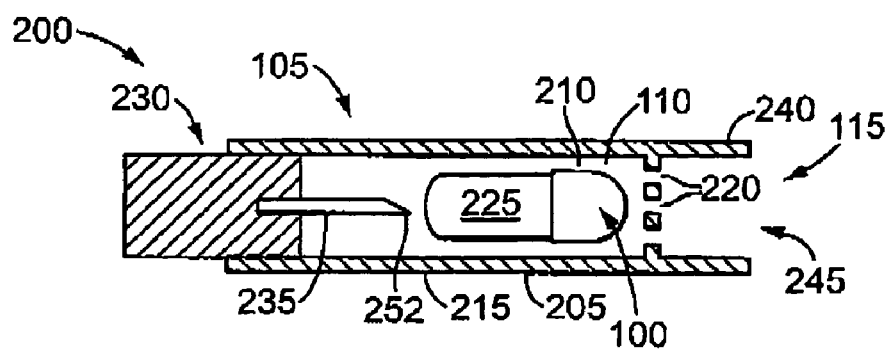
FIGS. 3A-3E are schematic sectional side views showing the operation of a dry powder inhaler that may be used to aerosolize pharmaceutical compositions of the present invention.

An example of a dry powder aerosolization apparatus particularly useful in aerosolizing a pharmaceutical composition 100 according to one or more embodiments of the present invention is shown schematically in FIG. 3A. The aerosolization apparatus 200 comprises a housing 205 defining a chamber 210 having one or more air inlets 215 and one or more air outlets 220. The chamber 210 is sized to receive a capsule 225 which contains an aerosolizable pharmaceutical composition comprising crystalline amphotericin B. A puncturing mechanism 230 comprises a puncture member 235 that is moveable within the chamber 210. Near or adjacent the outlet 220 is an end section 240 that may be sized and shaped to be received in a user's mouth or nose so that the user may inhale through an opening 245 in the end section 240 that is in communication with the outlet 220.

The dry powder aerosolization apparatus 200 utilizes air flowing through the chamber 210 to aerosolize the pharmaceutical composition in the capsule 225. For example, FIGS. 3A-3E illustrate the operation of a version of an aerosolization apparatus 200 where air flowing through the inlet 215 is used to aerosolize the pharmaceutical composition and the aerosolized pharmaceutical composition flows through the outlet 220 so that it may be delivered to the user through the opening 245 in the end section 240. The dry powder aerosolization apparatus 200 is shown in its initial condition in FIG. 3A. The capsule 225 is positioned within the chamber 210 and the pharmaceutical composition is contained within the capsule 225.

Figure 3B:
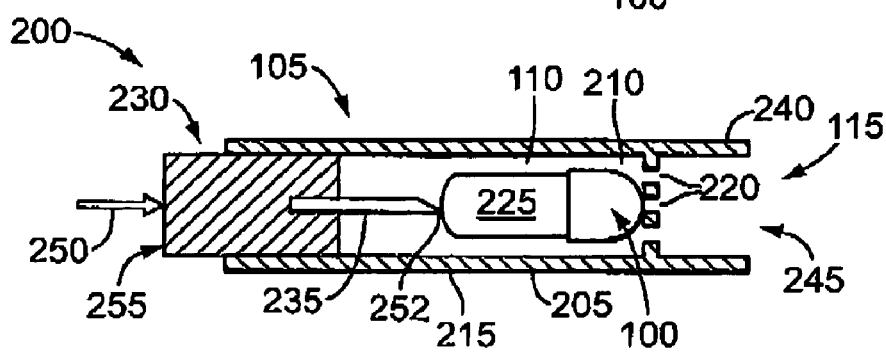
Figure 3C:
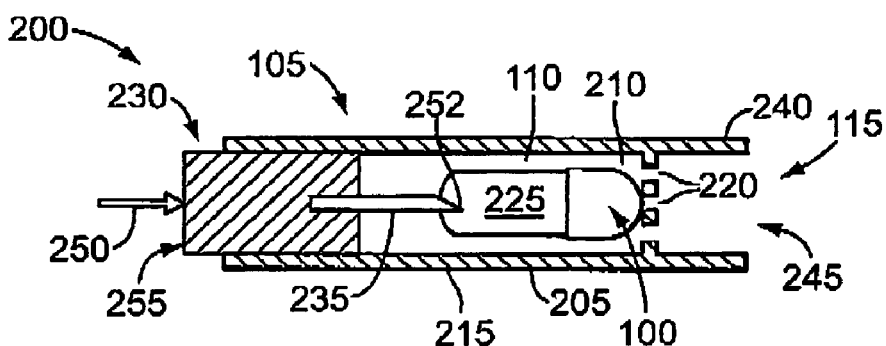
Figure 3D:
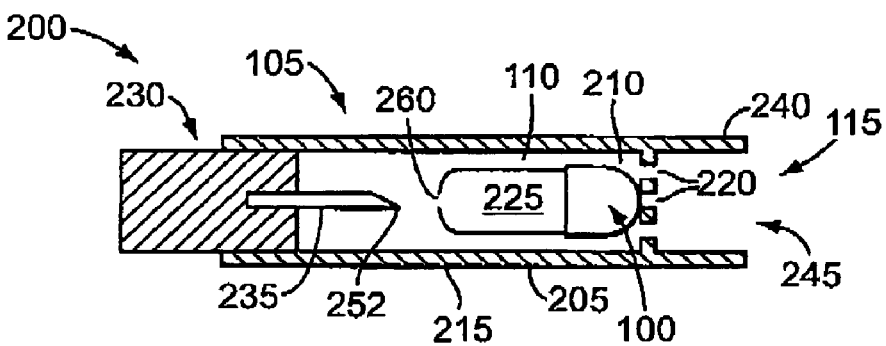

To use the aerosolization apparatus 200, the pharmaceutical composition in the capsule 225 is exposed to allow it to be aerosolized. In the version of FIGS. 3A-3E, the puncture mechanism 230 is advanced within the chamber 210 by applying a force 250 to the puncture mechanism 230. For example, a user may press against a surface 255 of the puncturing mechanism 230 to cause the puncturing mechanism 230 to slide within the housing 205 so that the puncture member 235 contacts the capsule 225 in the chamber 210, as shown in FIG. 3B. By continuing to apply the force 250, the puncture member 235 is advanced into and through the wall of the capsule 225, as shown in FIG. 3C. The puncture member may comprise one or more sharpened tips 252 to facilitate the advancement through the wall of the capsule 225. The puncturing mechanism 230 is then retracted to the position shown in FIG. 3D, leaving an opening 260 through the wall of the capsule 225 to expose the pharmaceutical composition in the capsule 225.

Figure 3E:
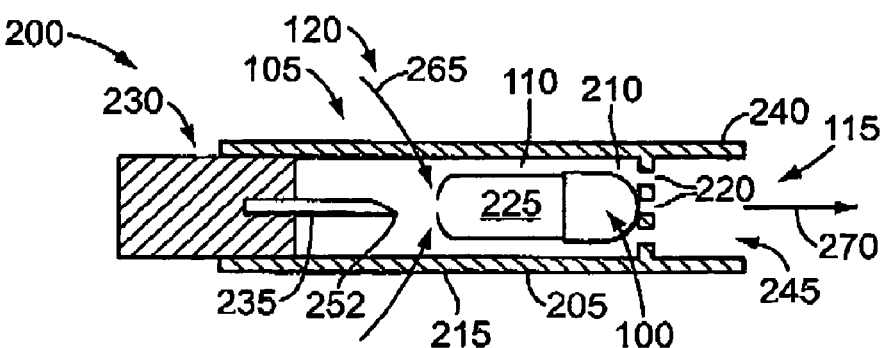

Air or other gas then flows through an inlet 215, as shown by arrows 265 in FIG. 3E. The flow of air causes the pharmaceutical composition to be aerosolized. When the user inhales 270 through the end section 240 the aerosolized pharmaceutical composition is delivered to the user's respiratory tract. In one version, the air flow 265 may be caused by the user's inhalation 270. In another version, compressed air or other gas may be ejected into the inlet 215 to cause the aerosolizing air flow 265.

A specific version of a dry powder aerosolization apparatus 200 is described in U.S. Pat. Nos. 4,069,819 and 4,995,385, which are incorporated herein by reference in their entireties. In such an arrangement, the chamber 210 comprises a longitudinal axis that lies generally in the inhalation direction, and the capsule 225 is insertable lengthwise into the chamber 210 so that the capsule's longitudinal axis may be parallel to the longitudinal axis of the chamber 210. The chamber 210 is sized to receive a capsule 225 containing a pharmaceutical composition in a manner which allows the capsule to move within the chamber 210. The inlets 215 comprise a plurality of tangentially oriented slots. When a user inhales through the endpiece, outside air is caused to flow through the tangential slots. This airflow creates a swirling airflow within the chamber 210. The swirling airflow causes the capsule 225 to contact a partition and then to move within the chamber 210 in a manner that causes the pharmaceutical composition to exit the capsule 225 and become entrained within the swirling airflow. This version is particularly effective in consistently aerosolizing high doses of the pharmaceutical composition. In one version, the capsule 225 rotates within the chamber 210 in a manner where the longitudinal axis of the capsule is remains at an angle less than 80 degrees, and preferably less than 45 degrees from the longitudinal axis of the chamber. The movement of the capsule 225 in the chamber 210 may be caused by the width of the chamber 210 being less than the length of the capsule 225. In one specific version, the chamber 210 comprises a tapered section that terminates at an edge. During the flow of swirling air in the chamber 210, the forward end of the capsule 225 contacts and rests on the partition and a sidewall of the capsule 225 contacts the edge and slides and/or rotates along the edge. This motion of the capsule is particularly effective in forcing a large amount of the pharmaceutical composition through one or more openings 260 in the rear of the capsule 225.

In another passive dry powder inhaler version, the dry powder aerosolization apparatus 200 may be configured differently than as shown in FIGS. 3A-3E. For example, the chamber 210 may be sized and shaped to receive the capsule 225 so that the capsule 225 is orthogonal to the inhalation direction, as described in U.S. Pat. No. 3,991,761, which is incorporated herein by reference in its entirety. As also described in U.S. Pat. No. 3,991,761, the puncturing mechanism 230 may puncture both ends of the capsule 225. In another version, the chamber may receive the capsule 225 in a manner where air flows through the capsule 225 as described for example in U.S. Pat. Nos. 4,338,931 and 5,619,985. In another version, the aerosolization of the pharmaceutical composition may be accomplished by pressurized gas flowing through the inlets, as described for example in U.S. Pat. Nos. 5,458,135; 5,785,049; and 6,257,233, or propellant, as described in WO 00/72904 and U.S. Pat. No. 4,114,615, which are incorporated herein by reference. These types of dry powder inhalers are generally referred to as active dry powder inhalers.

The pharmaceutical composition disclosed herein may also be administered to the pulmonary and/or nasal air passages of a patient via aerosolization, such as with a metered dose inhaler. The use of such stabilized preparations provides for superior dose reproducibility and improved lung deposition as disclosed in WO 99/16422, which is incorporated herein by reference in its entirety. MDIs are well known in the art and could be employed for administration of the amphotericin B. Breath activated MDIs, as well as those comprising other types of improvements which have been, or will be, developed are also compatible with the pharmaceutical composition of one or more embodiments of the present invention.

Nebulizers are known in the art and could easily be employed for administration of the claimed dispersions without undue experimentation. Breath activated nebulizers, as well as those comprising other types of improvements which have been, or will be, developed are also compatible with the stabilized dispersions, which are contemplated as being with in the scope of one or more embodiments of the present invention. Along with the aforementioned embodiments, the stabilized dispersions of one or more embodiments of the present invention may also be used in conjunction with nebulizers as disclosed in WO 99/16420, which is incorporated herein by reference in its entirety, in order to provide an aerosolized medicament that may be administered to the pulmonary and/or nasal air passages of a patient in need thereof.

Along with DPIs, MDIs and nebulizers, it will be appreciated that the stabilized dispersions of one or more embodiments of the present invention may be used in conjunction with liquid dose instillation or LDI techniques as disclosed in, for example, WO 99/16421, which is incorporated herein by reference in its entirety. Liquid dose instillation involves the direct administration of a stabilized dispersion to the lung. In this regard, direct pulmonary and/or nasal administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The time for dosing is typically short. For a single capsule (e.g., 5 mg dose), the total dosing time is normally less than about 1 minute. A 2 capsule dose (e.g., 10 mg) usually takes about 1 min. A 5 capsule dose (e.g., 25 mg) may take about 3.5 min to administer. Thus, the time for dosing may be less than about 5 min, such as less than about 4 min, less than about 3 min, less than about 2 min, or less than about 1 min.

The foregoing description will be more fully understood with reference to the following Examples. Such Examples, are, however, merely representative of methods of practicing one or more embodiments of the present invention and should not be read as limiting the scope of the invention.

EXAMPLE 1

Variability in Crystallinity Level of Amphotericin B between Different Lots

This Example involved determining the percent crystallinity values of several lots of amphotericin B by quantitative X-ray powder diffraction. This Example shows the range of crystallinity level for different lots of amphotericin B.

Equipment and Materials
  Equipment
  Sample holder
  Shimadzu X-ray diffractometer model XRD-6000
  Materials
  Silicon reference standard, NIST (National Institute of Standards and Technology) 640c
  Lithium Fluoride, particle size <5 μm
  Amphotericin B crystalline standard, sieved <48 μm
  Amphotericin B "amorphous", sieved <48 μm
  Vehicle powder (DSPC/CaCl$_2$ in a 2:1 molar ratio)

Method
  Alignment verification of the Shimadzu X-ray diffractometer model XRD-6000 was performed with the silicon reference standard. During alignment verification, the divergence slit was set at 1°, the scattering slit was set at 1.0°, and the receiving slit was set at 0.15 mm.
  Once the diffractometer was calibrated, X-ray powder diffraction data were acquired on calibration standards and lots of unknown crystallinity (sample size of about 60 mg). The following settings were used for this data acquisition:
  Dwell time: 2 seconds (fixed time scan)
  Step size: 0.02°2θ
  Scanning range: 3-42°2θ
  Slits: 0.5° divergence slit, 1° scattering slit, and 0.3 mm receiving slit.

To prepare calibration plots to determine crystallinity of amphotericin B in samples, an internal standard method was used. The internal standard was LiF. Physical mixtures of the crystalline and wide-angle X-ray amorphous standards were prepared. Hereafter in this Example, the wide-angle X-ray amorphous standard will be referred to as "amorphous." These physical mixtures were then doped with LiF at 20 wt %.

The crystalline standard was selected from among several lots of highly crystalline amphotericin B. Based on a qualitative comparison of X-ray powder diffraction patterns, the material with the smallest amorphous background was selected. An amorphous standard was prepared by cryogenically milling the crystalline material (i.e., the same lot of amphotericin B was used for both amorphous and crystalline amphotericin B standards). Both standards were sieved to less than 48 μm before preparation of physical mixtures. Physical mixtures were prepared at 40±5% RH (20-25° C.). All weighing was done on an analytical balance with a resolution of at least 0.01 mg.

Data Analysis
  The ratio of the integrated intensities of diffraction peaks of crystalline amphotericin B to a peak of LiF was calculated from the diffraction pattern of each LiF-doped physical mixture. The integrated intensity ratio, IIR, is given by:

$$IIR = \frac{I_{AmB,Cr}}{I_{LiF}}$$

where $I_{AmB,Cr}$ and $I_{LiF}$ are the integrated intensities of the selected reference peaks of crystalline Amphotericin B and LiF, respectively. A single diffraction peak (38 to 39.5°2θ was selected for LiF, and a narrow angular range was selected for amphotericin B (12.75-16.25°2θ). Only a couple of amphotericin B peaks were used because it eliminated the need to draw/interpolate a curved baseline, and these peaks were sensitive to incipient crystallinity. Peaks were integrated using Jade software (MDI Inc.), version 7.1.2.

Results and Discussion
  Table 1 shows the crystallinity results for several lots of amphotericin B. The maximum variance of the drug substance method is about ±10% crystalline, and is dependent on the percent crystallinity. While not wishing to be bound by theory, due to the vastly different bulk densities of the selected standards, the uncertainty in the results is due to variability in the compression used to fill the sample holder. An improvement in the precision could likely be attained by using a lower sample mass (resulting in less need for sample compression)

TABLE 1

| Lot | Sample Number | % Crystallinity | Average % Crystallinity |
| --- | --- | --- | --- |
| A | N = 1 | 61 | 60 |
|   | N = 2 | 61 |   |
|   | N = 3 | 59 |   |
| B | N = 1 | 82 | 80 |
|   | N = 2 | 77 |   |
| C | N = 1 | 11 | 11 |
|   | N = 2 | 10 |   |
|   | N = 3 | 10 |   |
| D | N = 1 | 46 | 48 |
|   | N = 2 | 47 |   |
|   | N = 3 | 50 |   |
| E | N = 1 | 94 | 94 |
| F | N = 1 | 6 | 6 |
|   | N = 2 | 6 |   |
| G | N = 1 | 104 | 104 |
| H | N = 1 | 93 | 93 |
| I | N = 1 | 102 | 102 |
| J | N = 1 | 90 | 90 |
|   | N = 2 | 90 |   |

EXAMPLE 2

Preparation of Spray-dried Amphotericin B Particulates

Amphotericin B particulates were prepared by a two-step process. In the first step, 10.52 g of amphotericin B (Alpharma, Copenhagen, Denmark), 10.12 g of distearoyl phosphatidylcholine (DSPC) (Genzyme, Cambridge, Mass.), and 0.84 g calcium chloride (JT Baker, Phillipsburg, N.J.) were dispersed in 1045 g of hot deionized water (T=70° C.) using an Ultra-Turrax mixer (model T-25) at 10,000 rpm for 2 to 5 min. Mixing was continued until the DSPC and amphotericin B appeared visually to be dispersed.

381 g of perfluorooctyl ethane (PFOE) was then added slowly at a rate of approximately 50-60 mL/min during mixing. After the addition was complete, the emulsion/drug dispersion was mixed for an additional period of not less than 5 min at 12,000 rpm. The coarse emulsion was then passed through a high pressure homogenizer (Avestin, Ottawa, Canada) at 12,000-18,000 psi for 3 passes, followed by 2 passes at 20,000-23,000 psi.

The resulting fine emulsion was utilized as the feedstock in for the second step, i.e. spray-drying on a Niro Mobile Minor. The following spray conditions were employed: total flow rate=70 SCFM, inlet temperature=110° C., outlet temperature=57° C., feed pump=38 mL/min, atomizer pressure=105 psig, atomizer flow rate=12 SCFM.

A free-flowing pale yellow powder was collected using a cyclone separator. The collection efficiency was 60%. The geometric diameter of the amphotericin B particulates was confirmed by laser diffraction (Sympatec Helos, Clausthal-Zellerfeld, Germany), where a volume weighted mean diameter (VMD) of 2.44 µm was found. Scanning electron microscopy (SEM) analysis showed the powders to be small porous particulates with high surface roughness. There was no evidence of any unincorporated amphotericin B crystals in the 5 SEM views of powder from each collector. Differential scanning calorimetry analysis of the dry particulates revealed the $T_m$ of the distearoyl phosphatidylcholine in the powder to be 78° C., which is similar to what is observed for spray-dried neat distearoyl phosphatidylcholine.

EXAMPLE 3

Aerosol Performance for Spray-dried Amphotericin B Particulates

The resulting dry amphotericin B particulates prepared in Example 2 were hand filled into #2 HPMC capsules (Shionogi, Japan) that had been allowed to equilibrate at 15-20% RH overnight at ambient temperature. A fill mass of approximately 10 mg was used, which represented approximately ½ the fill volume of the #2 HPMC capsule.

Figure 4:
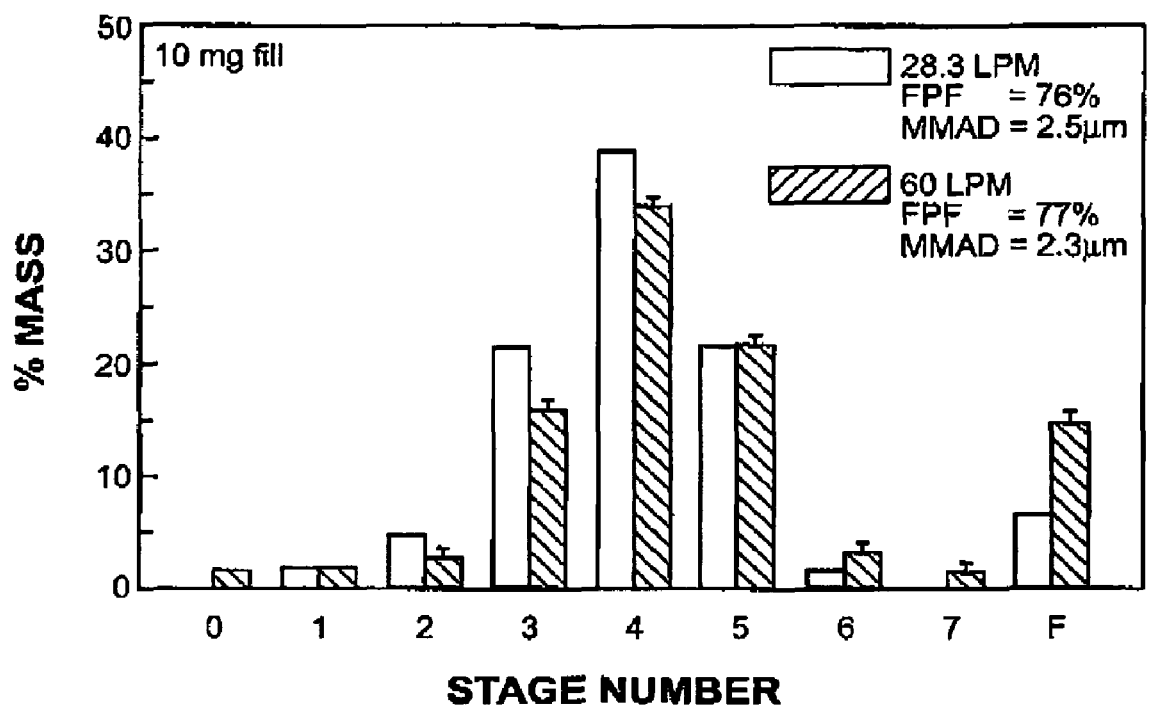
FIG. 4 is a graphical representation showing a plot of flow rate dependence of deposition in an Anderson Cascade Impactor (ACI) for an amphotericin B powder of the present invention.

Aerodynamic particulate size distributions were determined gravimetrically on an Andersen cascade impactor (ACI). Particulate size distributions were measured at flow rates of 28.3 L/min (i.e., comfortable inhalation effort) and 56.6 L/min (i.e., forceful inhalation effort) using the Turbospin® DPI device described in U.S. Pat. Nos. 4,069,819 and 4,995,385, which are incorporated herein by reference in their entireties. A total volume of 2 liters was drawn through the device. At the higher flow rate, two ACIs were used in parallel at a calibrated flow rate of 28.3 L/min and a total flow through the device of 56.6 L/min. In both cases the set-up represents conditions at which the ACI impactor plates are calibrated. Excellent aerosol characteristics were observed as evidenced by a MMAD less than 2.6 µm and $FPF_{<3.3\ \mu m}$ greater than 72%. The effect of flow rate on performance was also assessed (FIG. 4) using the Turbospin® (PH&T, Italy) DPI device operated at 56.6 L/min into 2 ACIs used in parallel. No significant difference in the deposition profile was observed at the higher flow rates, demonstrating minimal flow rate dependant performance. This abovementioned example illustrates the aerosol performance of the present powder is independent of flow rate, which should lead to more reproducible patient dosing.

EXAMPLE 4

Effect of Storage on Aerosolization of Amphotericin B Particulates

The resulting dry amphotericin B particulates prepared in Example 2 were hand filled into #2 HPMC capsules (Shionogi, Japan) that had been allowed to equilibrate at 15-20% RH overnight. A fill mass of approximately 10 mg was used, which represented approximately ½ the fill volume of the #2 HPMC capsule. The filled capsules were placed in individually indexed glass vials that were packaged in laminated foil-sealed pouch and subsequently stored at 25° C./60% RH or 40° C./75% RH.

Emitted dose (ED) measurements were performed using the Turbospin® (PH&T, Italy) DPI device, described in U.S. Pat. No. 4,069,819 and in U.S. Pat. No. 4,995,385, operated at its optimal sampling flow rate of 60 L/min, and using a total volume of 2 liters. A total of 10 measurements were determined for each storage variant.

The aerodynamic particulate size distributions were determined gravimetrically on an Andersen cascade impactor (ACI). Particulate size distributions were measured at flow rates of 28.3 L/min using the Turbospin® DPI device and using a total volume of 2 L.

Figure 5:
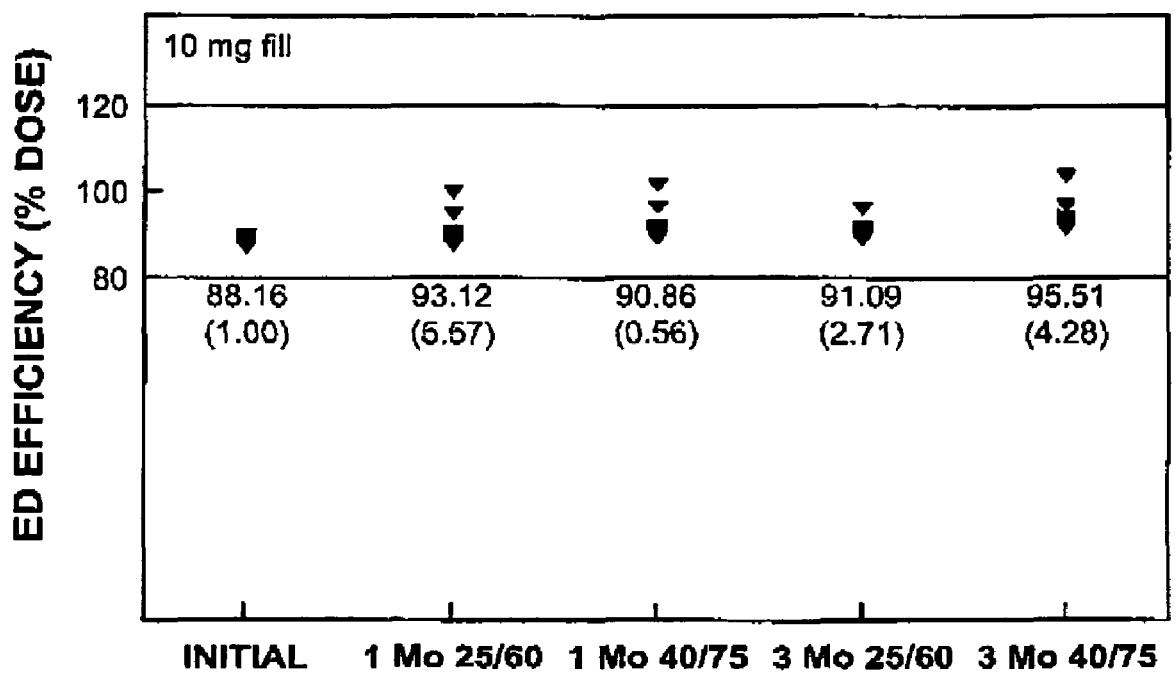
FIG. 5 is a graphical representation showing stability of an amphotericin B powder of the present invention emitted dose (ED) using the Turbospin® DPI device at 60 L/min.
Figure 6:
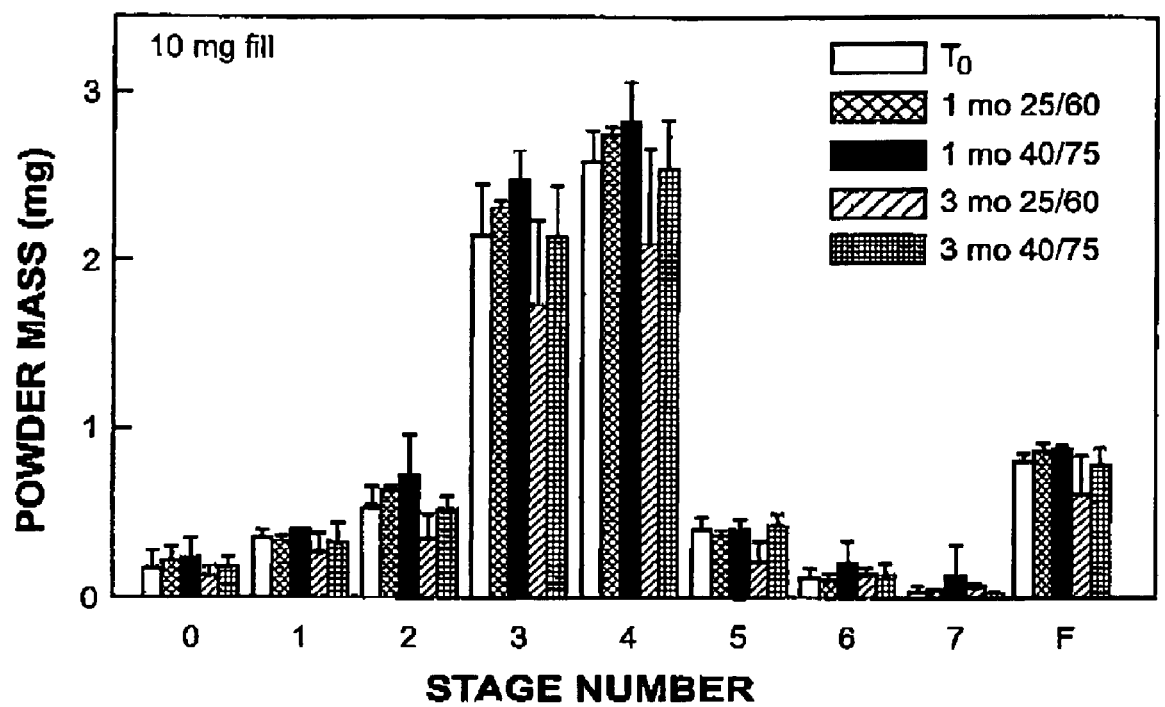
FIG. 6 is a graphical representation showing a plot of stability of an amphotericin B powder of the present invention aerosol performance using the Turbospin® DPI device at 28.3 L/min.

Excellent aerosol characteristics were observed as evidenced by a mean ED of 93%±5.3%, MMAD=2.6 µm and $FPF_{<3.3\ \mu m}$=72% (FIGS. 5 and 6). No significant change in aerosol performance (ED, MMAD or FPF) was observed after storage at elevated temperature and humidity, demonstrating excellent stability characteristics. Current USP requirements for ED performance stipulate that >90% of the delivered doses be within ±25% of the label claim, with less than 10% of the doses beyond ±25% but within ±35%. A recent draft guidance published by the FDA proposes that the limits be tightened, such that >90% of the delivered doses be within ±20% of the label claim, with none outside of ±25%. Statistically speaking, an RSD of 6% would be required to meet the proposed FDA specifications.

Not only are the results of the foregoing example within the current guidelines, but they are also within the limits of the proposed guidelines. Accordingly, the composition had good dispersibility, aerosol characteristics, and stability.

EXAMPLE 5

Spray-dried Amphotericin B Particulates Using Various Phosphatidylcholines

Spray-dried particulates comprising approximately 50 wt % amphotericin B were prepared using various phosphatidylcholines (PC) as the surfactant following the two-step process described in Example 2. Compositions were prepared using dipalmitoyl phosphatidylcholine (DPPC) (Genzyme, Cambridge, Mass.), distearoyl phosphatidylcholine (DSPC) (Genzyme, Cambridge, Mass.), and SPC-3 (Lipoid KG, Ludwigshafen, Germany). The feed solution was prepared using the identical equipment and process conditions described therein. The 50 wt % amphotericin B composition is as follows:

| | |
|---|---|
| Amphotericin B | 0.733 g |
| PC | 0.714 g |
| $CaCl_2$ | 60 mg |
| PFOB | 32 g |
| DI water | 75 g |

The resulting multi-particulate emulsion was utilized as the feedstock for the second step, i.e. spray-drying on a B-191 Mini Spray-Drier (Büchi, Flawil, Switzerland). The following nominal spray conditions were employed: aspiration=100%, inlet temperature=85° C., outlet temperature=60° C., feed pump=1.9 mL/min, atomizer pressure=60-65 psig, atomizer flow rate=30-35 cm. The aspiration flow (69-75%) was adjusted to maintain an exhaust bag pressure of 30-31 mbar. Free flowing yellow powders were collected using a standard cyclone separator. The geometric diameter of the amphotericin B particulates was measured by laser diffraction (Sympatec Helos, Clausthal-Zellerfeld, Germany), where the volume weighted mean diameter (VMD) ranged from 2.65 to 2.75 μm. Scanning electron microscopy (SEM) analysis showed the powders to be small porous particulates with high surface roughness.

Figure 7:
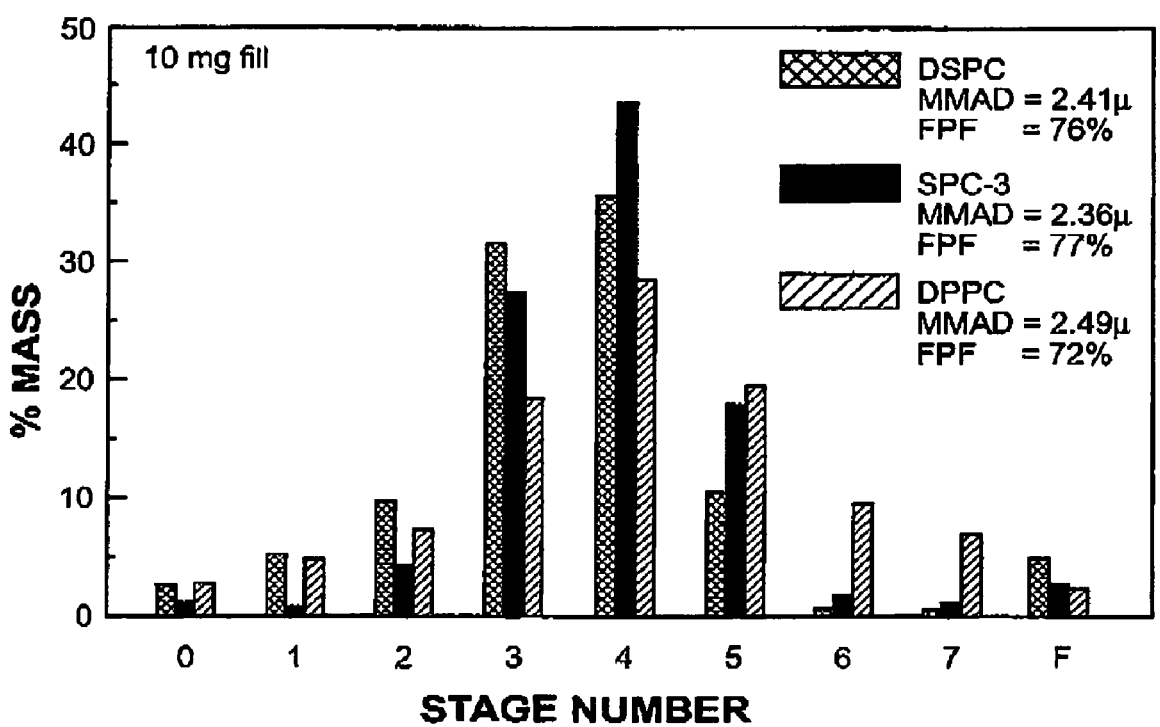
FIG. 7 is a graphical representation showing a plot of aerosol performance of a pharmaceutical composition of the present invention comprising amphotericin B and various phosphatidylcholines.

Aerodynamic particulate size distributions were determined gravimetrically using an Andersen cascade impactor (ACI), see FIG. 7. Particulate size distributions were measured at flow rates of 56.6 L/min (i.e., forceful inhalation effort) using the Turbospin® DPI device. A total volume of 2 liters was drawn through the device. Two ACIs were used in parallel at a calibrated flow rate of 28.3 L/min and a total flow through the devices of 56.6 L/min. Similar aerosol characteristics were observed in the amphotericin B produced with the 3 types of phosphatidylcholines, with MMADs less than 2.5 μm and $FPF_{<3.3\ \mu m}$ greater than 72%. This abovementioned example illustrates the flexibility of the composition technology to produce amphotericin B powders independent of the type of phosphatidylcholine employed.

EXAMPLE 6

Preparation of 70 Wt % Amphotericin B Spray-dried Particulates

Amphotericin particulates were prepared following the two-step process described in Example 2. The feed solution was prepared using the identical equipment and process conditions described therein. The 70 wt % amphotericin B composition is as follows:

| | |
|---|---|
| Amphotericin B | 0.70 g |
| DSPC | 0.265 g |
| CaCl$_2$ | 24 mg |
| PFOB | 12 g |
| DI water | 35 g |

The resulting multi-particulate emulsion was utilized as the feedstock for the second step, i.e. spray-drying on a B-191 Mini Spray-Drier (Büchi, Flawil, Switzerland). The following spray conditions were employed: aspiration=100%, inlet temperature=85° C., outlet temperature=60° C., feed pump=1.9 mL min$^{-1}$, atomizer pressure=60-65 psi, atomizer flow rate=30-35 cm. The aspiration flow (69-75%) was adjusted to maintain an exhaust bag pressure of 30-31 mbar. A free flowing yellow powder was collected using a standard cyclone separator. The geometric diameter of the amphotericin B particulates was measured by laser diffraction (Sympatec Helos, Clausthal-Zellerfeld, Germany), where a volume weighted mean diameter (VMD) of 2.96 μm was determined. Scanning electron microscopy (SEM) analysis showed the powders to be small porous particulates with high surface roughness. This foregoing example illustrates the flexibility of the present powder engineering technology to produce high amphotericin B content using the herein described multi-particulate approach.

EXAMPLE 7

Aerosol Performance of Spray-dried Amphotericin B Particulates

The resulting dry amphotericin B particulates prepared in Example 6 were hand filled into #2 HPMC (Shionogi, Japan) or #3 HPMC (Capsugel, Greenwood, S.C.) capsules and allowed to equilibrate at 15-20% RH overnight at ambient temperature. A fill mass of approximately 10 mg was used, which represents approximately half the fill volume for a #2 HPMC capsule or ⅝ for a #3 HPMC capsule. The aerosol characteristics were examined using Turbospin® (PH&T, Italy), Eclipse® (Aventis, UK), and Cyclohaler® (Novartis, Switzerland) DPI devices. The Cyclohaler® utilizes a # 3 HPMC capsule, whereas the Turbospin® and Cyclohaler® devices utilize size # 2 HPMC capsules.

Figure 8:
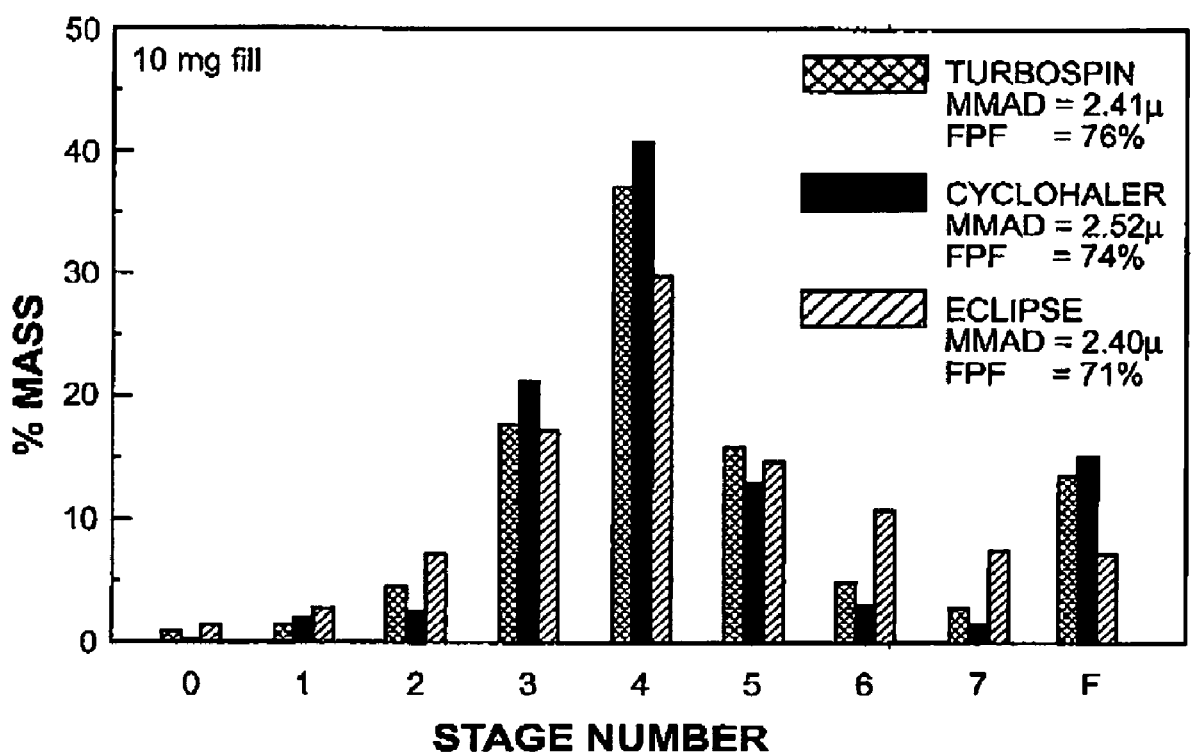
FIG. 8 is a graphical representation showing a plot of aerosol performance of a pharmaceutical composition of the present invention comprising 70 wt % amphotericin B using various passive DPI devices at 56.6 L/min.

Aerodynamic particulate size distributions were determined gravimetrically using an Andersen cascade impactor (ACI), see FIG. 8. Particulate size distributions were measured at a flow rate 56.6 L/min, which represents a forceful inhalation effort for both Turbospin® and Eclipse® DPI devices and comfortable for Cyclohaler® devices. A total volume of 2 L was drawn through the device. Two ACIs were used in parallel at a calibrated flow rate of 28.3 L/min and a total flow through the devices of 56.6 L/min. Similar aerosol characteristics were observed in all devices as evidenced by a MMAD less than 2.5 μm and $FPF_{<3.3\ \mu m}$ greater than 71%. This abovementioned example illustrates the aerosol performance of the present powder is independent of device design with medium and low resistance, and independent of capsule size, which demonstrates the dispersibility of the amphotericin B powder tested.

EXAMPLE 8

Aerosol Performance of Spray-dried Amphotericin B Particulates

This Example further examines the aerosol performance of developmental lots of amphotericin B particulates.

Figure 9:
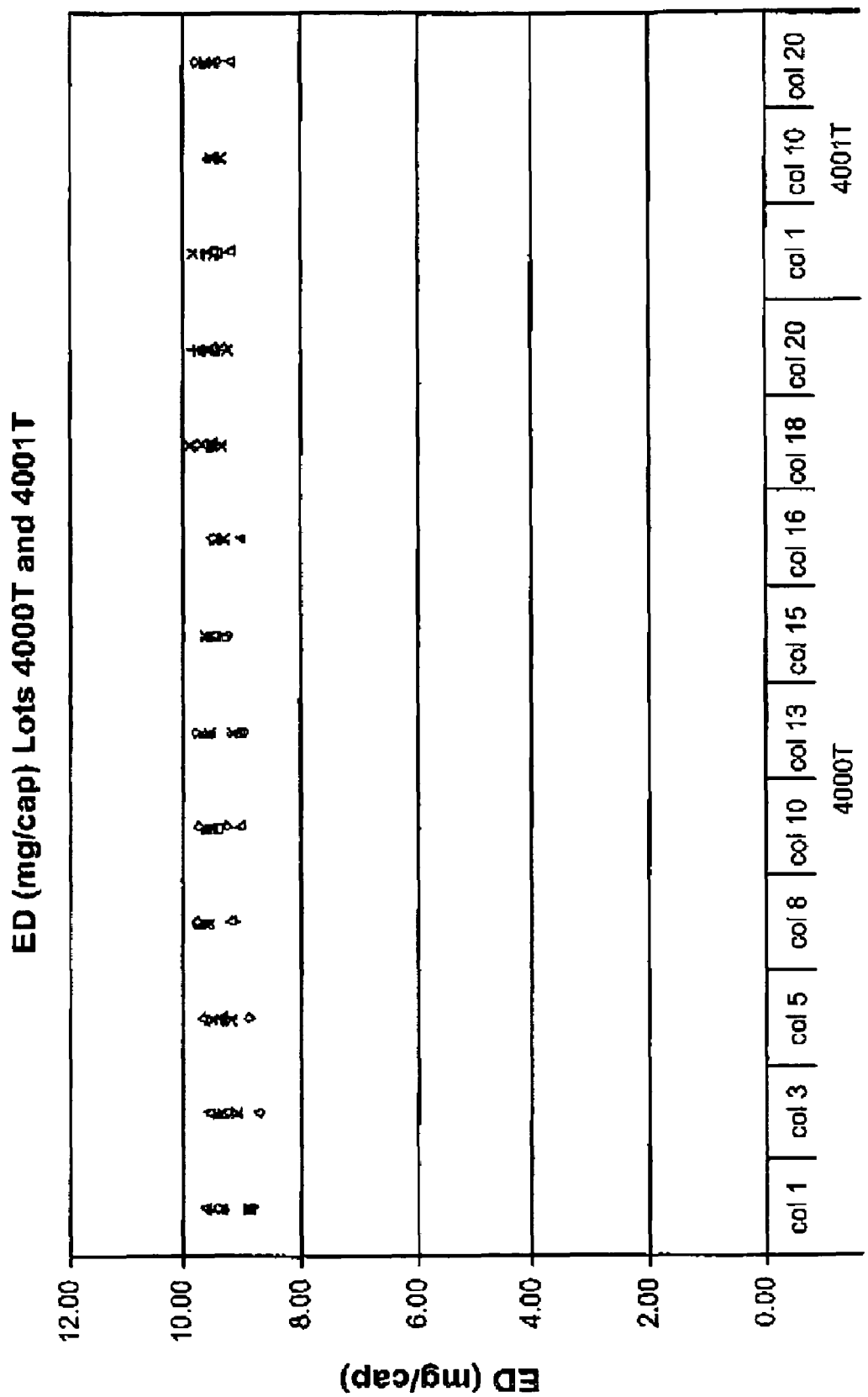
FIG. 9 shows the ED obtained per collector from powders of the present invention.
Figure 10:
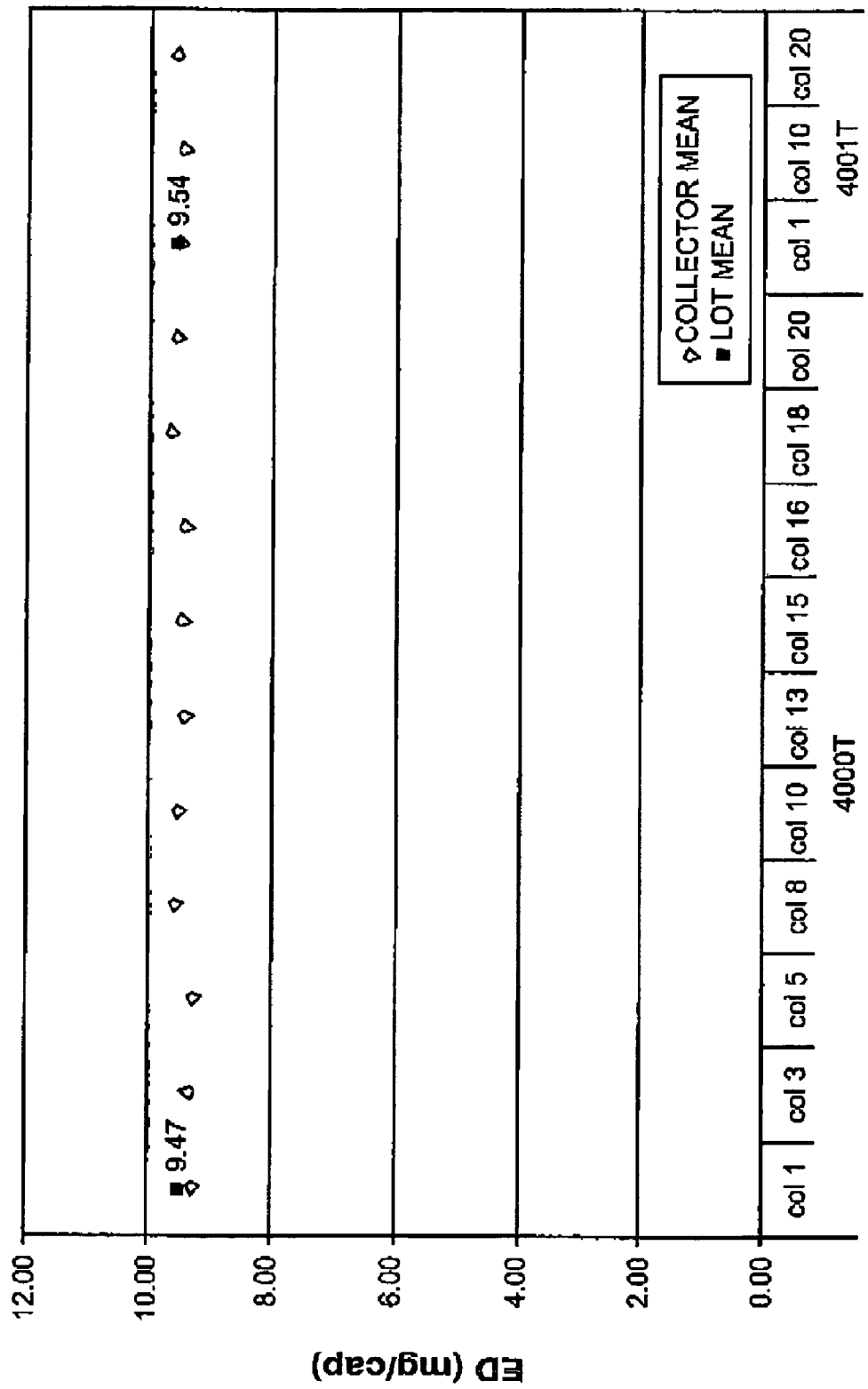
FIG. 10 shows the mean ED per lot from powders of the present invention.

The following amphotericin B particulates were formed using the process of Example 2, wherein the amphotericin B was obtained from Alpharma.
4000T
4001T FIGS. 9 and 10 show the emitted dose (ED) (mg/capsule) and mean ED per collector and per lot, respectively. To determine the ED, an inhaler device as shown in U.S. application Ser. No. 10/298,177, which is herein incorporated by reference in its entirety, was used.

Figure 11:
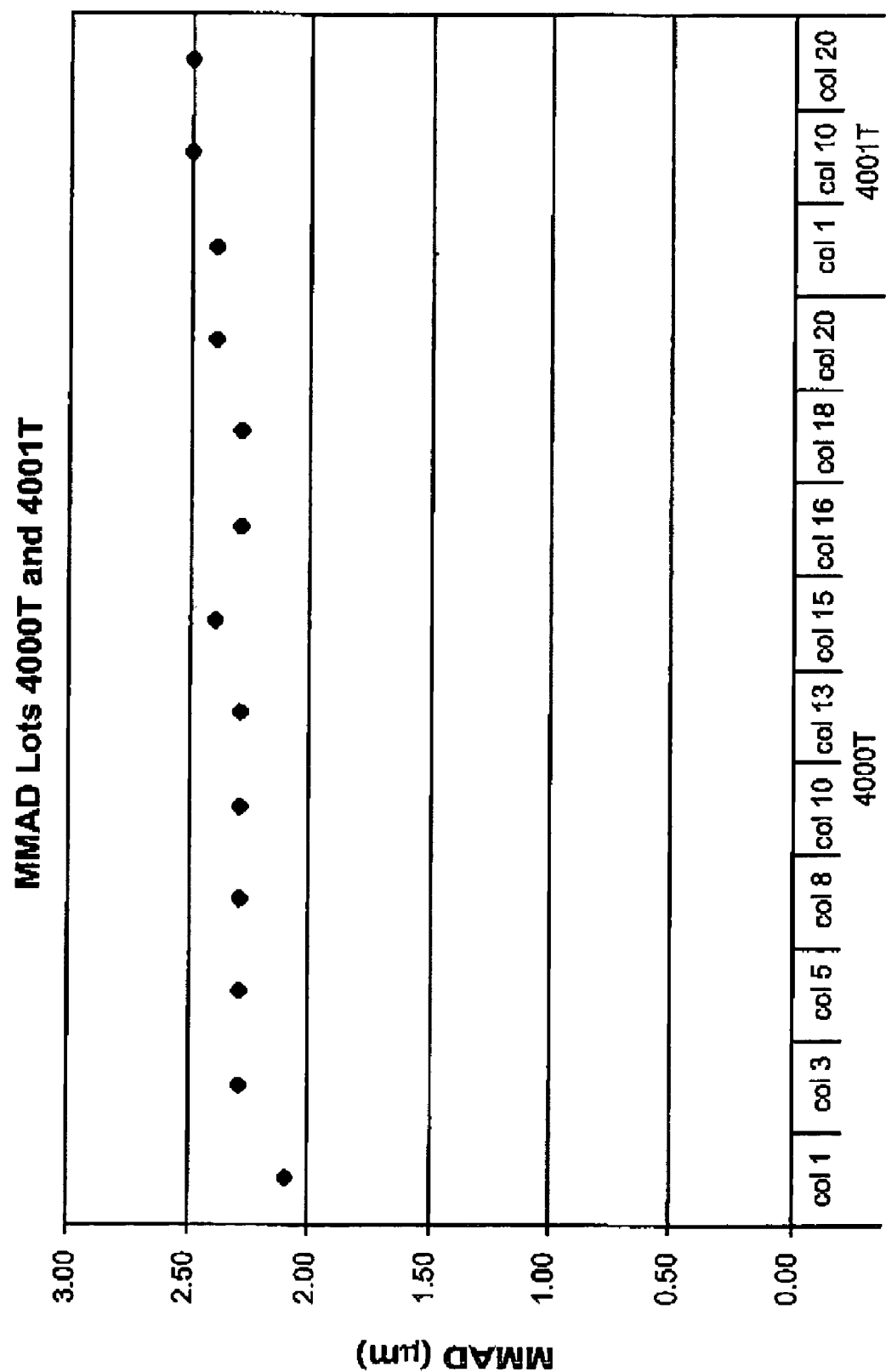
FIG. 11 shows mass median aerodynamic diameters (MMAD) per collector of powders of the present invention.
Figure 12:
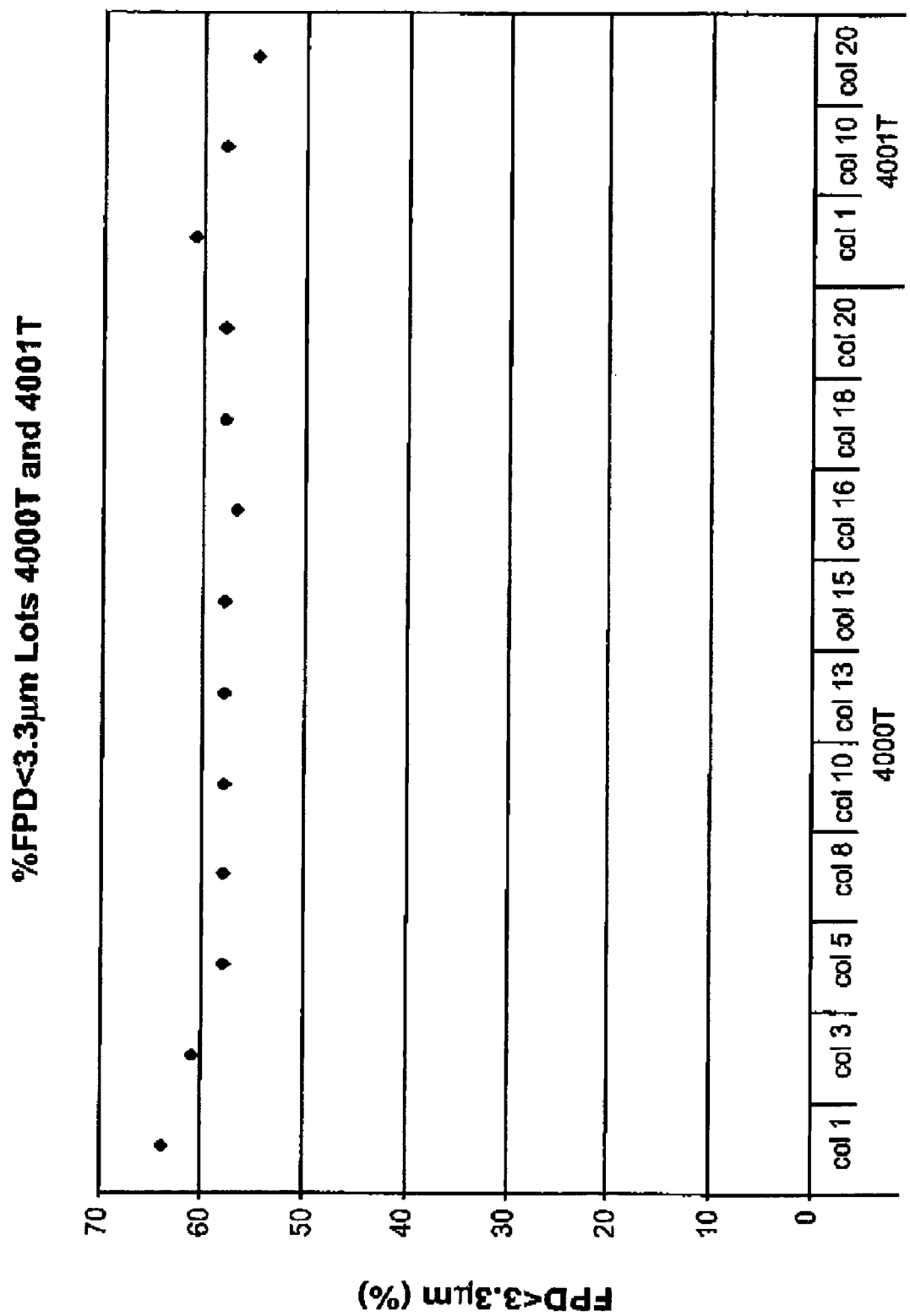
FIG. 12 shows fine particle doses (%FPD<3.31 μm) per collector of powders of the present invention.

FIGS. 11 and 12 show the mass median aerodynamic diameter (MMAD) and fine particle dose (%FPD<3.3 μm) per collector, respectively.

Figure 13:
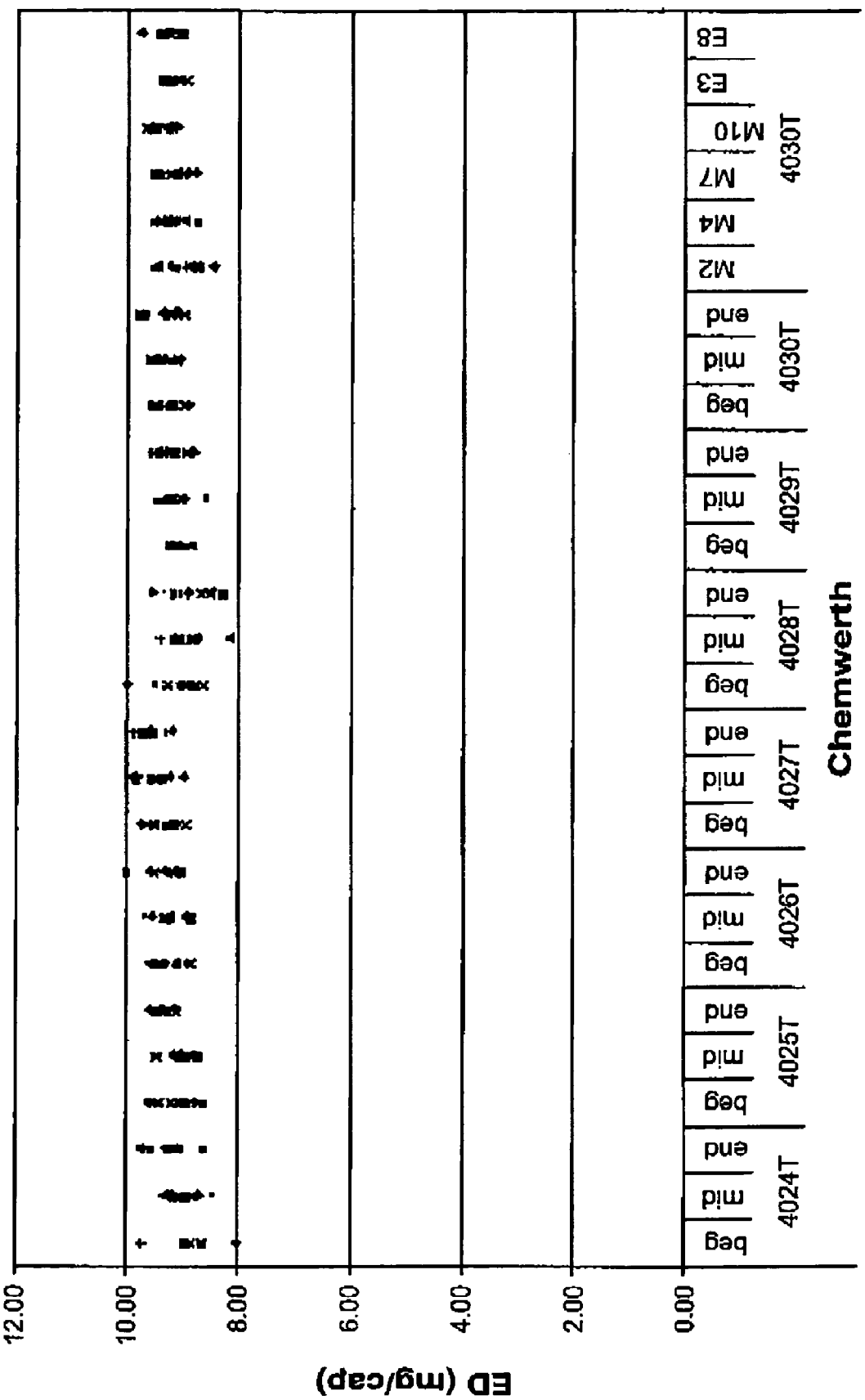
FIG. 13 shows ED (mg/capsule) per collector of powders of the present invention.
Figure 14:
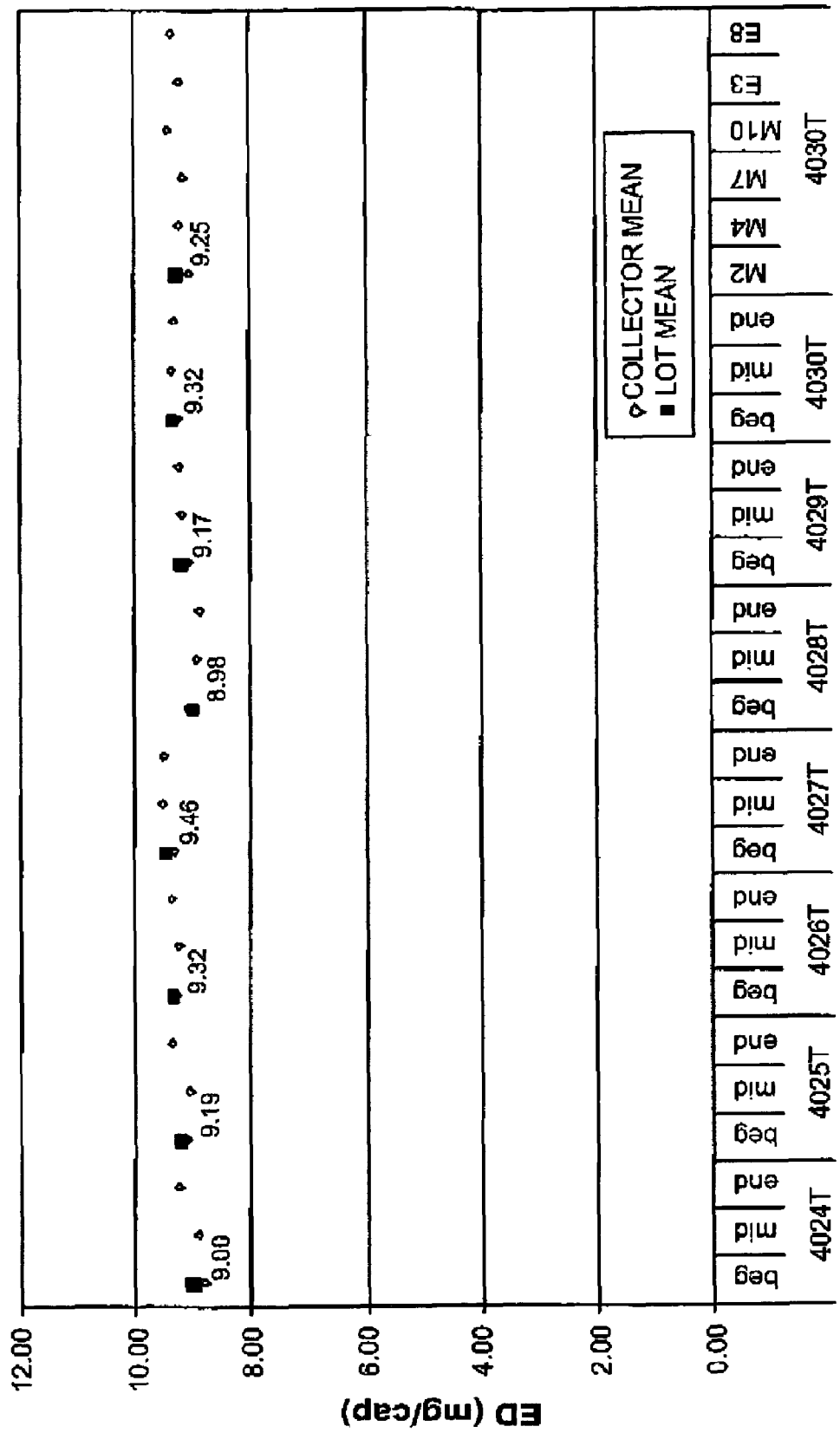
FIG. 14 shows mean ED per collector and per lot of powders of the present invention.

The following amphotericin B particulates were formed using the process of Example 2, wherein the amphotericin B was obtained from Chemwerth.
4024T
4025T
4026T
4027T
4028T
4029T
4030T FIGS. 13 and 14 show the emitted dose (ED) (mg/capsule) and mean ED per collector and per lot, respectively.

Figure 15:
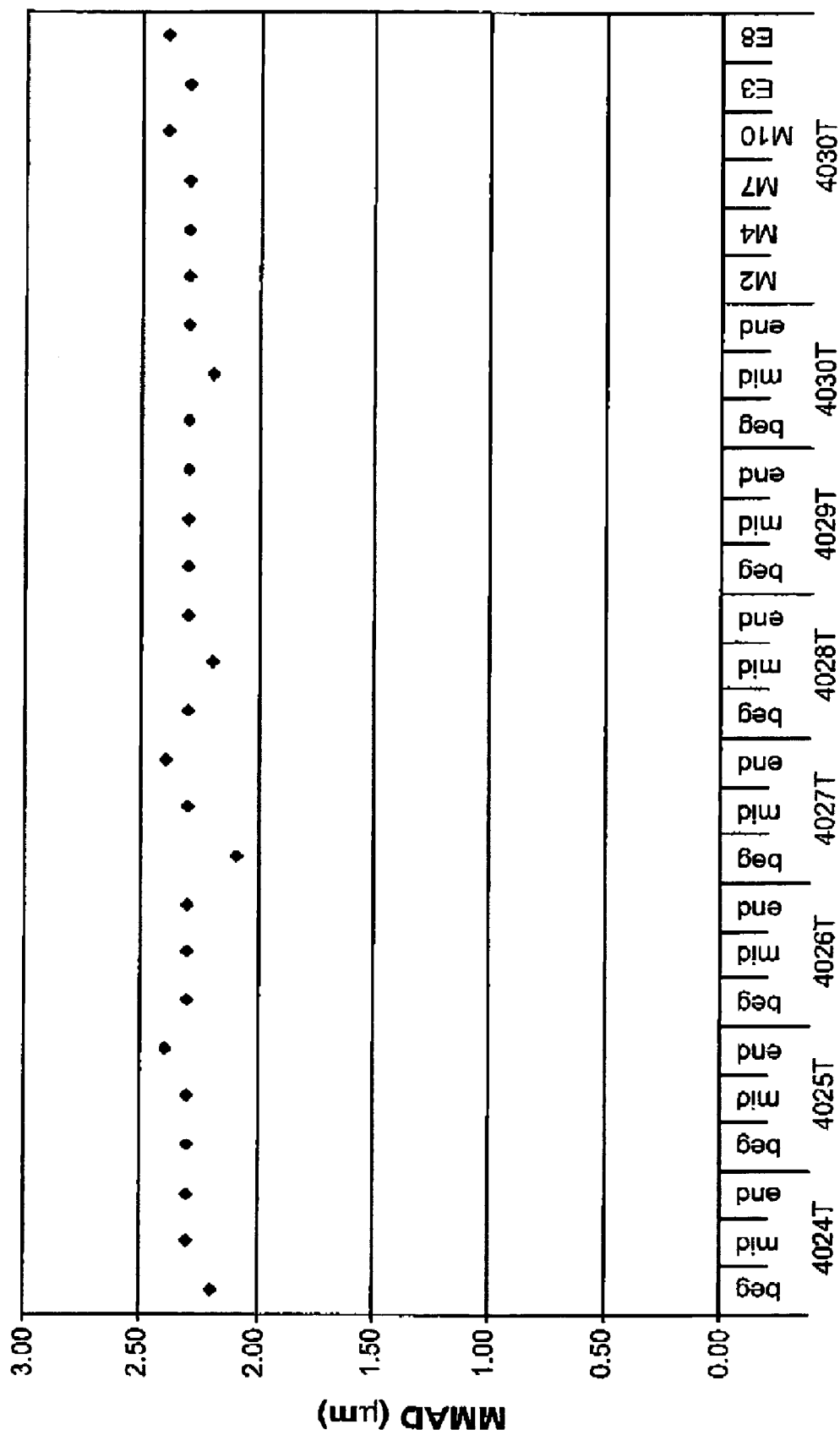
FIG. 15 shows MMAD per collector of powders of the present invention.
Figure 16:
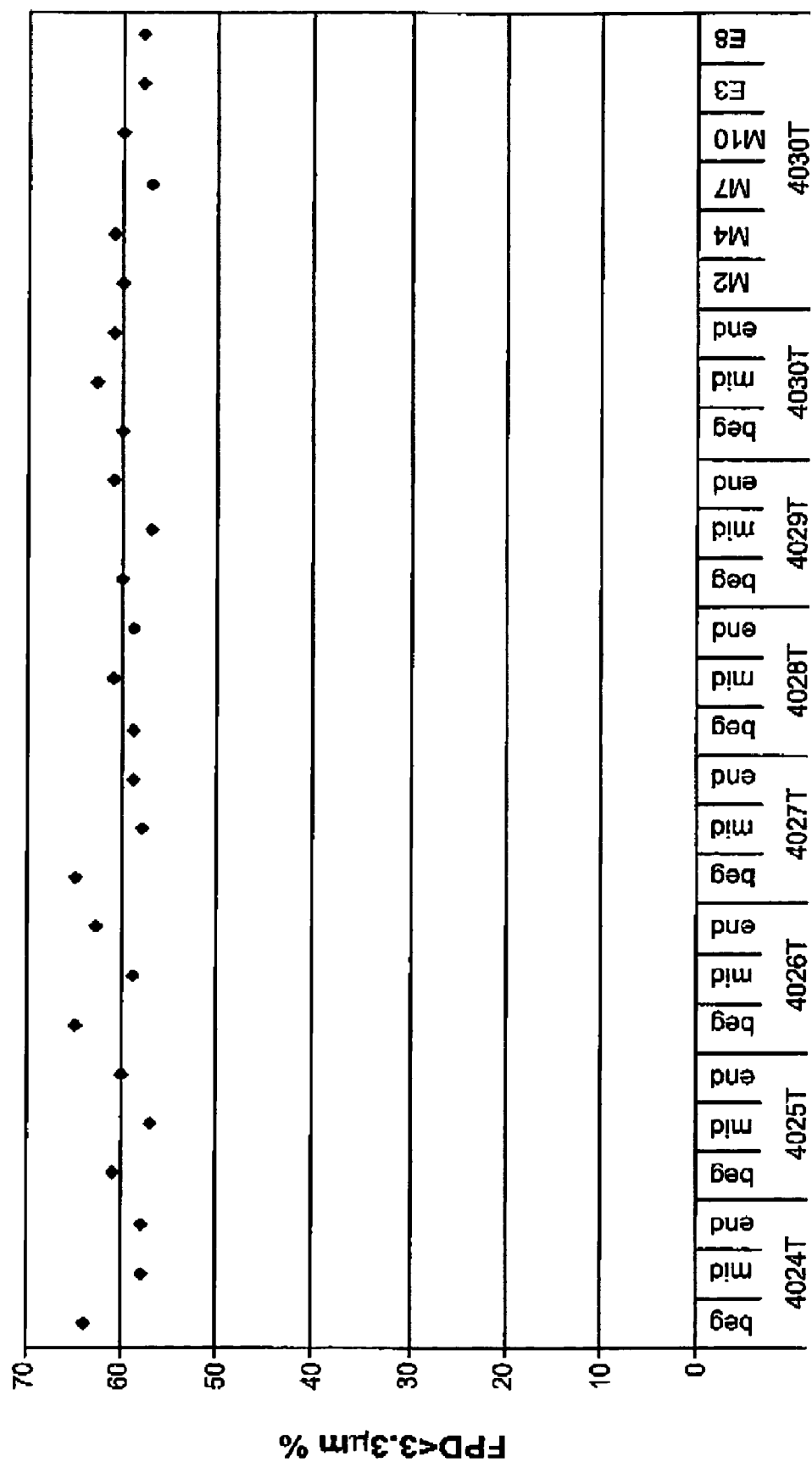
FIG. 16 shows %FPD<3.3 μm per collector of powders of the present invention.

FIGS. 15 and 16 show the mass median aerodynamic diameter (MMAD) and %FPD<3.3 μm per collector, respectively.

As described in more detail below, the following amphotericin B particulates were formed using processed amphotericin B:
N020226 (from highly crystalline API)
N020227 (from highly amorphous API)

These amphotericin B particulates were formed using a variation of the process of Example 2, wherein the amphotericin B was originally manufactured by Alpharma. Before spray drying, however, the amphotericin B was processed to achieve either (i) highly amorphous; or (ii) highly crystalline API batches (as determined by X-Ray powder diffraction).

Specifically, the procedure for reprocessing amphotericin B is provided below. As shown in the below flow diagram and following description, both crystalline and amorphous forms were produced from the same starting material.

pH Adjustment and Precipitation/Crystallization

Precipitation of Amphotericin B was achieved through adjustment of the solution to pH~7 using 40% triethanolamine (~140 mL). For the amorphous form, the base was added in a single pour with stirring. The amorphous form was then ready for isolation as described below.

For the crystalline form, the base was added dropwise over 30 minutes with stirring. The slurry was then heated to 44-46° C. for 90 minutes followed by cooling to room

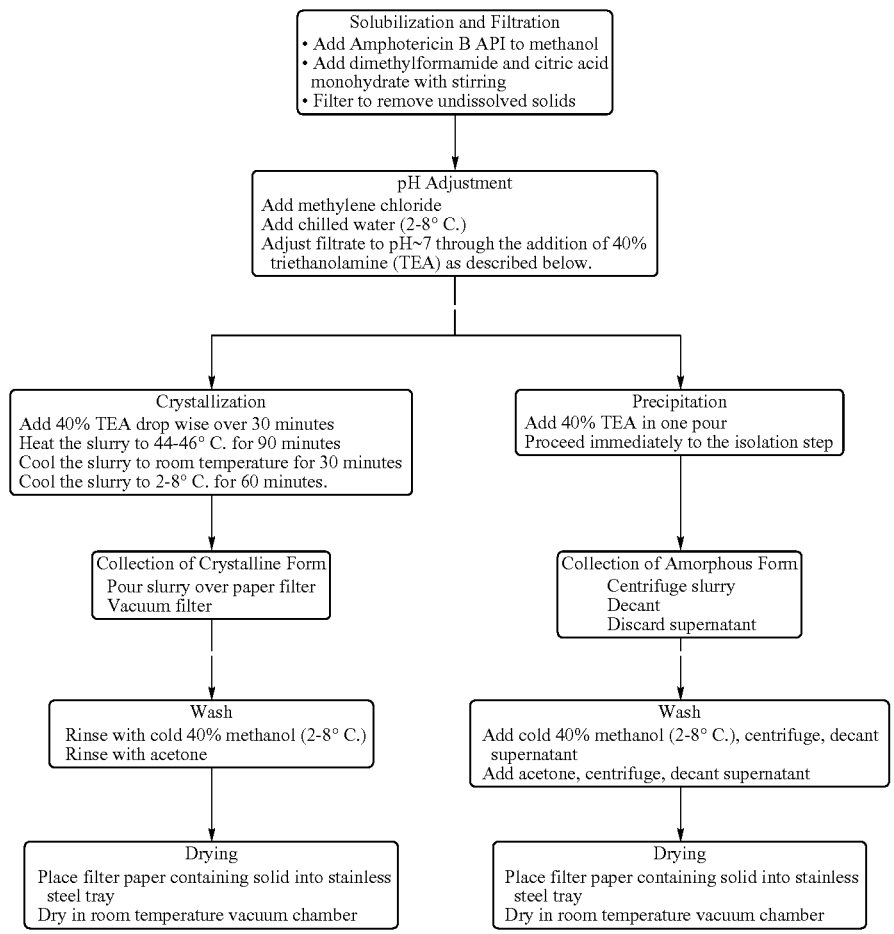

Description of Reprocessing Procedure for Amphotericin B Drug Substance (API)

Solubilization and Filtration

Approximately 20 g of amphotericin B was added to 1130 mL methanol at room temperature with stirring. Approximately 450 mL dimethylformamide followed by 39 g citric acid monohydrate were added to the Amphotericin B suspension with continuous stirring. Once all solids were essentially dissolved, the solution was clarified by filtration.

Approximately 280 mL of methylene chloride was added to the filtrate. The vessel containing the product was protected from light for the duration of reprocessing. Approximately 450 mL of chilled (2-8° C.) water was added, and the solution was stirred for 15 minutes.

temperature for 30 minutes. Finally, the slurry was cooled at 2-8° C. for 60 minutes. The crystalline form was then ready for isolation.

Collection and Washing of the Crystalline Form

The crystalline form of amphotericin B was captured by vacuum filtration using a large stainless steel Buchner funnel lined with a paper filter. The product was washed using 170 mL of chilled 40% methanol (2-8° C.) followed by 100 mL acetone (room temperature).

Collection and Washing of the Amorphous Form

The amorphous form of amphotericin B was captured through centrifugation of the slurry followed by decanting of the supernatant. The product was washed by resuspension of the cake in 600 mL of chilled 40% methanol (2-8° C.)

followed by centrifugation and decanting. The washing process was repeated using 600 mL acetone (room temperature).

Drying of the Crystalline and Amorphous Forms

Filter paper containing the washed crystalline amphotericin B was placed in a stainless steel tray within a vacuum chamber. Similarly, washed amorphous amphotericin B was removed from the centrifuge bottles and spread onto a paper filter lined stainless steel tray within the chamber. The drying process proceeded for 1 to 3 days at room temperature with the product protected from light. Occasionally, during the drying process, larger particles were broken using a spatula to facilitate evaporation of residual solvents. The final amphotericin B product was transferred to amber glass jars for storage at 2-8° C.

Figure 17:
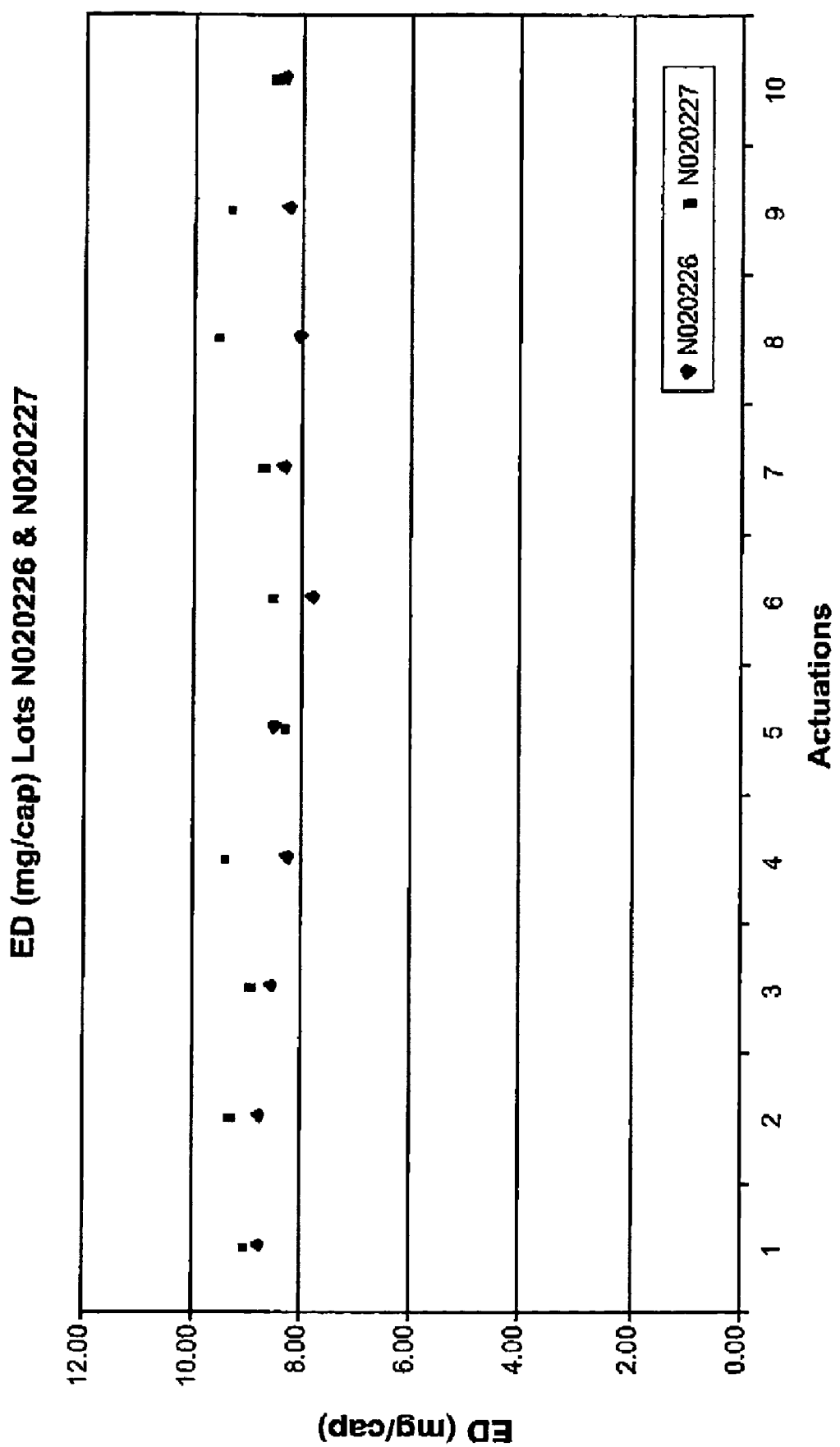
FIG. 17 shows ED (mg/capsule) for two powders of the present invention.
Figure 18:
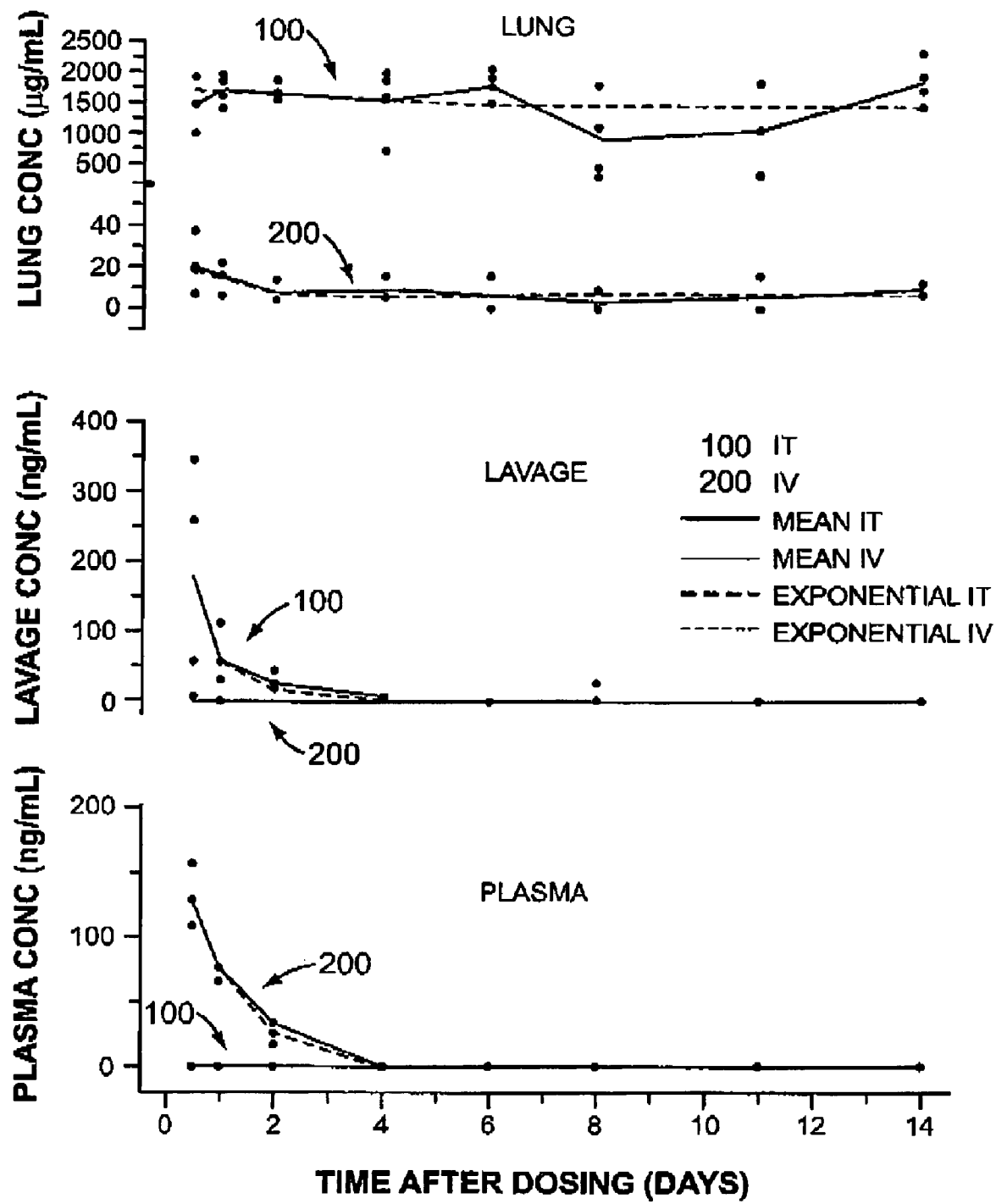
FIG. 18 is a graphical representation showing the amphotericin B concentrations at various locations in the body of rat after intratracheal administration and intravenous administration.

As noted above, the amphotericin B particulates were then formed using the process of Example 2. FIG. 17 shows the Emitted Dose (ED) (mg/capsule) for both N020226 and N020227. The mass median aerodynamic diameter (MMAD) for N020226 and N020227 were found to be 2.4 μm and 2.6 μm, respectively. The %FPD<3.3 μm for N020226 and N020227 were found to be 55% and 47%, respectively.

EXAMPLE 9 AND COMPARATIVE EXAMPLE 1

Comparison of Intratracheal and Intravenous Administration

This Example involved determining the concentrations of amphotericin B in plasma, lung lavage fluid, and lung tissue following intratracheal administration of an amphotericin B solution or intravenous administration of a commercial amphotericin B deoxycholate solution.

Materials and Methods

Sprague-Dawley Rats (Hilltop Lab Animals Inc, Scottdale, Pa.) supplied pre-cannulated jugular vein cannula [JVC]) and weighing between 334-366 grams were used in this Example. Amphotericin B was administered by intratracheal instillation or intravenous injection. The study design is presented in Table 2.

TABLE 2

| Group | Route of Administration | Number/ Gender of Animals | Dose | Dose Volume (mL) | Blood, Lung Tissue, BAL Collection (Day) |
|---|---|---|---|---|---|
| Amphotericin B Powder | Intratracheal (IT) | 32 M | 4.0 mg (~11 mg/kg) | 0.3 | 0.5, 1, 2, 4, 6, 8, 11, and 14 |
| Amphotericin B Deoxycholate Formulation | Intravenous (IV) | 24 M | 0.5 mg (~14 mg/kg) | 1.0 | 0.5, 1, 2, 4, 6, 8, 11, and 14 |

BAL = bronchoalveolar lavage
M = Male

The amphotericin B solution for intratracheal instillation was prepared in phosphate buffered saline (PBS) at a concentration of 13.3 mg amphotericin B/mL. The amphotericin B deoxycholate intravenous formulation was provided as a 50 mg amphotericin B lyophilized cake that was reconstituted to make a solution containing 1 mg/mL.

Study endpoints and procedures included body weights prior to dose administration, collection of blood, BAL, and tissue collection for drug concentration analysis and gross necropsy observations.

Blood, BAL, and lung tissue samples were collected at 12 hours, 1, 2, 4, 6, 8, 11, and 14 days post-dose. At each sampling time, four (4) animals from the IT group and (3) three animals from the IV group were sacrificed and blood, lung lavage fluid and lung tissue samples taken.

Plasma and lavage samples were analyzed for amphotericin B concentrations by MDS Pharma Services, Montreal, Canada. Lung tissue samples were analyzed for amphotericin B concentrations by MedTox Laboratories, St. Paul, Minn.

Results

Gross Necropsy Observations

Rats administered amphotericin B by intratracheal instillation exhibited gross signs of lung toxicity. Observations included lung edema, bleeding in the lung, and discoloration of lung tissue.

Amphotericin B Concentrations in BAL, Lung Tissue, and Plasma

The plasma, BAL, and lung tissue amphotericin B concentrations, and estimated ELF amphotericin B concentrations after delivery of amphotericin B intratracheally 100 and intravenously 200, is shown in FIG. 18. As can be seen, when administered to the respiratory tract, little amphotericin B was present systemically. In contrast, high amphotericin B concentrations were present in the blood for up to four days following intravenous administration. As also demonstrated in FIG. 18, the pulmonary amphotericin B concentrations were higher for intratracheal administration 100 than for intravenous administration 200. In the experiment conducted, the lung amphotericin B concentrations were many times greater for intratracheal administration than for intravenous administration while the plasma amphotericin B concentrations were less for intratracheal administration.

Conclusions and Discussion

Rats administered amphotericin B by intratracheal liquid instillation exhibited gross signs of toxicity. Observations included lung edema, bleeding in the lung, and discoloration of lung tissue.

Amphotericin B was not measurable in any of the plasma samples taken from animals that received the test article via intratracheal administration. Measurable concentrations were found in the BAL and lung tissue from animals administered amphotericin B by intratracheal instillation. Drug was measured in the BAL of all animals for 2 days post IT dose and in 1 out of 4 animals 8 days post dose. Drug was measured in lung tissue for all animals at 14 days post IT dose.

In animals given amphotericin B intraveneously, drug was measured for up to 2 days postdose in the plasma, but the animals had no measurable drug in the lung at any of the time points, and only 1 animal had measurable concentrations of amphotericin B in the BAL at 12 hours post-dose.

In conclusion, intratracheal delivery of 11 mg/kg amphotericin B in solution at a concentration of 13.3 mg/mL resulted in local lung toxicity. Intratracheal administration also resulted in concentrations above the limit of quantitation for 14 Days after dose administration. In contrast, the concentration of amphotericin B was below the limit of quantitation in the lung tissue of animals administered amphotericin B intravenously.

EXAMPLE 10 AND COMPARATIVE EXAMPLE 2

Comparison of Aerosolized and Intravenous Administration

Aerosolizable amphotericin B powder was pulmonarily administered to dogs for 14 days. The amphotericin B was delivered in daily doses of up to 11.5 mg/kg. The dose of amphotericin B powder was delivered to conscious dogs using a face mask containing a one way valve to exhaust exhaled air and an inhalation line connected to a central holding chamber containing the aerosolized powder. A respirable dry powder aerosol of the formulated amphotericin B powder was created using by dispersing the powder with a rotating brush generator and delivered to the central chamber for the 30 min inhalation exposure.

Figure 19:
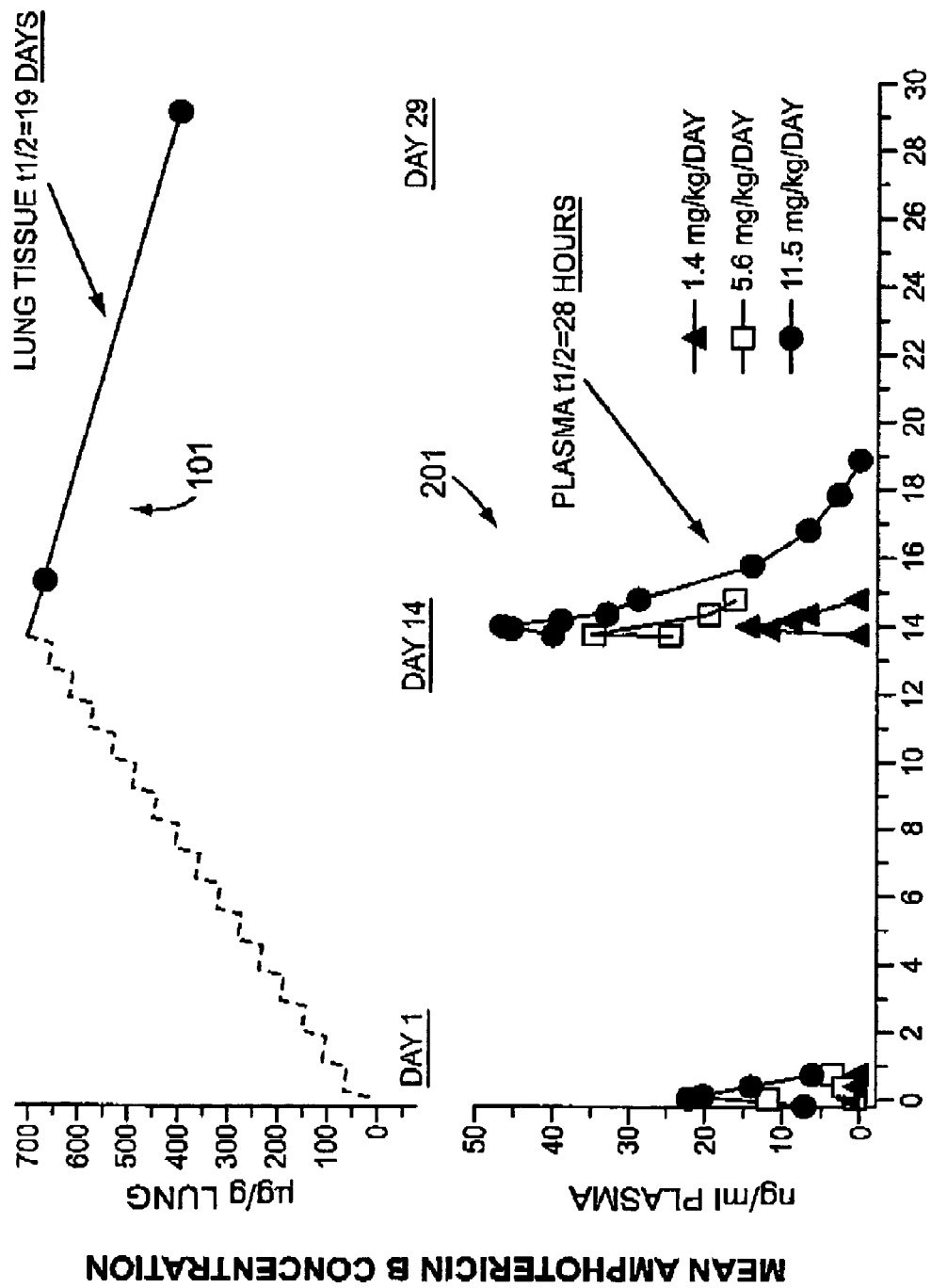
FIG. 19 is a graphical representation showing the mean amphotericin B concentration-time profiles in the lungs of dogs after 14 days of pulmonary administration.

FIG. 19 shows the mean lung amphotericin B concentration-time profiles in dogs 101 following administration. As can be seen, the amphotericin B resided in the lungs for several days following administration with an observed half-life of approximately 19 days. In contrast, the intravenous administration 201 was not well retained, having an observed half-life of about 28 hr.

EXAMPLE 11

Increased Survival Rate with Prophylactic Administration

Summary

This Example involved determining if amphotericin B administered prophylactically via inhalation was efficacious against Aspergillus fumigatus in an immunosuppressed rabbit model. An objective of this study was to determine if a single administration of amphotericin B by inhalation prior to an Aspergillus fumigatus inoculum would increase survival time and/or decrease total mortality.

This study had three groups, with 10 animals each. Group 1 received the immunosuppressive regimen of intravenous cytarabine and methyl prednisolone and a sham saline inoculation. Group 2 received the immunosuppressive regimen and $5 \times 10^7$ conidia of A. fumigatus. Group 3 received the immunosuppressive regimen and an estimated amphotericin B dose of 1.5 mg/kg via inhalation one day prior to an inoculation of $5 \times 10^7$ conidia of A. fumigatus. The amphotericin B dry powder formulation and A. fumigatus were administered to anesthetized rabbits via an endotracheal tube. The immunosuppressive agents were administered by intravenous injection. Antibiotics to prevent bacterial infections were administered by intravenous injection or in the drinking water.

Evaluations performed in this study included mortality and morbidity, daily clinical observations, body weights, clinical pathology (hematology and clinical chemistry), gross necropsy, lung weight, enumeration of visible lung infarctions, fungal colony forming unit (CFU) measurements in BAL, blood, and lung tissue samples, and histopathological evaluation of lung tissue.

The percentage of animals surviving until the planned conclusion of the study on Day 14 was as follows: 60% in Group 1, 20% in Group 2, and 70% in Group 3. The average survival time for animals in Groups 1 and 3 was 13 days and the median day of death or sacrifice for both groups was Day 14. In contrast, the average survival for animals in Group 2 was 10 days and the median day of death or sacrifice was Day 10. Kaplan-Meier (KM) analysis showed a significant ($p<0.05$) increase in the survival of animals administered amphotericin B prior to inoculation with A. fumigatus (Group 3) compared with animals administered only A. fumigatus (Group 2). Survival of Group 1 (control) animals was also significantly increased compared with Group 2. There was no significant difference when Groups 1 and 3 were compared.

Clinical signs of respiratory effects, including gasping, wheezing, or rales were observed in Group 2 and 3 animals. These signs were not observed in Group 1 animals. In Group 2 seven of the animals group exhibited gasping, wheezing, or rales beginning on study Day 7. All the animals in Group 2 that exhibited signs of respiratory effects were either found dead or became moribund within one day of exhibiting the signs. In Group 3, five of the animals were observed wheezing, gasping, or having rales. However, while the earliest incidence of respiratory signs was also on Day 7, only two of the animals that exhibited signs of respiratory effects became moribund. The other 3 animals survived until their scheduled necropsy with two of the three (both which had rales) ceased to exhibit signs of respiratory effects by Day 14.

Effects on body weights were observed in all groups. Body weight decreased in all groups by approximately Day 8. All the groups exhibited a decrease of approximately 6% by Day 8. After the initial decline, the body weights for the remaining animals in Group 1 and Group 2 remained stable for the duration of the study. In contrast, the average group body weight of the animals in Group 3 continued to decrease and by Day 14 were 18% below their starting body weight and were 10% lower than Group 1 body weight average.

Effects were seen on the measured hematology and clinical chemistry parameters in all groups. The primary effect seen on hematology parameters was a decreased level of white blood cells (WBC), including decreased segmented neutrophils (ANS) and platelets (PLC). These effects were seen in all groups.

Additional effects were noted on the levels of red blood cells, hemoglobin, hematocrit, total protein, albumin, aspartate aminotransferase, alanine aminotransferase, total bilirubin, direct bilirubin, cholesterol, globulin, and triglycerides in Groups 2 and 3. The decreased levels of red blood cells (RBC), hemoglobin (HGB), and hematocrit (HCT) seen in groups 2 and 3 are indicative of anemia and are consistent with the hemorrhage seen microscopically in lung tissue. The decreased levels of total protein (TPR), albumin (ALB) along with the increased levels of aspartate aminotransferase (AST), alanine aminotransferase (ALT), total bilirubin (TBI) and direct bilirubin (DBI) and cholesterol (CHO) seen in Groups 2 and 3 are consistent with hepatic effects. The increased globulin (GLO) is likely the result of a response to the fungal infection and/or inflammation that was observed microscopically in the lung. The increased triglycerides (TRI) levels are consistent with fat mobilization seen with decreased food consumption and body weight observed in this study.

A gross necropsy was performed on surviving animals on Day 14 as well as on animals that were sacrificed after becoming moribund. The number of lung infarctions per animal were counted during the gross necropsy. There were no visible infarctions in Group 1. Seven of eight (88%) animals in Group 2 that were available for necropsy had visible lung infarctions and of these animals 6 of 8 (75%) had more than 20 grossly visible infarctions. In Group 3, eight of ten animals (80%) had visible lung infarction, however in contrast to Group 2, only two of 10 (20%) had more than 20 grossly visible lung infarctions.

A microbiological evaluation of bronchoalveolar lavage fluid, blood, and lung tissue samples taken at necropsy was performed. No colony forming units (CFU) were detected in any of the samples from Group 1. For Group 2, samples for culture were obtained from 8 of the 10 animals. No samples were available from the 2 animals found dead. Six of the animals evaluated (75%) had 1 or more tissues that were positive for fungus. For Group 3, samples for culture were obtained from 9 of 10 animals, with 4 of the animals (44%) having 1 or more tissues positive for fungus.

Absolute lung weights as well as the lung-to-body weight increased in Groups 2 and 3 compared with Group 1.

The lung histopathological evaluations showed that no mycotic hyphae were present in any of the pulmonary tissue evaluated from control rabbits. Mycotic hyphae were present in 44% of the Group 2 animals evaluated and in 50% of the Group 3 animals. There were no differences microscopically between the tissues of either group. Lung sections from rabbits having mycotic infection also had associated secondary changes that included edema, necrosis, hemorrhage, alveolar macrophage proliferation, interstitial inflammation, and/or perivascular inflammation. The changes present were similar in severity and prevalence. The microscopic evaluation of the available tissue sections was able to verify fungal infection in approximately half of the animals evaluated. There were no differences microscopically between the tissues or mycotic hyphae in Groups 2 or 3.

In conclusion, based on the mortality data along with the supporting clinical observations, microbiology data, and lung infarction, amphotericin B provided a prophylactic effect against *A. fumigatus* induced mortality in the immunosuppressed rabbit model used for this study.

Study Design

There were 3 study groups with 10 animals in each group in this experiment. Group 1 received the immunosuppressive regimen of intravenous cytarabine and methyl prednisolone and a sham saline inoculation. Group 2 received the immunosuppressive regimen and $5 \times 10^7$ conidia of *A. fumigatus*. Group 3 received the immunosuppressive regimen and an estimated amphotericin B pulmonary dose of 1.5 mg/kg one day prior to an inoculation of $5 \times 10^7$ conidia of *A. fumigatus*. The general design is given in Table 3, below.

TABLE 3

| Group | Immunosuppressive Regimen | Target Dose of Amphotericin B (mg/kg) | *A. fumigatus* (Conidia/animal) |
|---|---|---|---|
| 1 | Yes | None | 0[a] |
| 2 | Yes | None | $5 \times 10^7$ |
| 3 | Yes | 1.5[b] | $5 \times 10^7$ |

[a]Inoculated with diluent (0.025% Tween 20 in 0.9% sodium chloride)
[b]Amphotericin B treated on Day-1

Mammalian Test System and Animal Husbandry

New Zealand White SPF rabbits that were dual catheterized with vascular access ports (VAPs) and weighing between 2.5 to 4.0 kg at study initiation were used. The rabbits were randomly assigned to treatment groups using a computerized body weight stratification procedure.

Number/Gender per Group

10/female per group; 3 groups

Immunosuppression and Neutropenia

Immunosuppression was induced in rabbits to simulate the condition of human patients, as shown in Table 4, below.

TABLE 4

| Drug | Purpose | Dose Level | Route of Admin. | Frequency | Study Days |
|---|---|---|---|---|---|
| Cytarabine | Immunosuppression | 44 mg/kg | IV | sid | −1, 1, 2, 3, 4 |
| Cytarabine | Maintain neutropenia | 40 mg/kg | IV | sid | 7, 8, 12, 13 |
| Methylprednisolone | Inhibit macrophage production | 5 mg/kg | IV | sid | −1, 1 |
| Ceftazidime | Prevent bacterial infection | 75 mg/kg | IV | bid | 3 thru 13 |
| Gentamicin | Prevent bacterial infection | 5 mg/kg | IV | qod | 3, 5, 7, 9, 11, 13 |
| Vancomycin | Prevent bacterial infection | 15 mg/kg | IV | sid | 3 thru 13 |
| Vancomycin | Prevent bacterial infection | 50 mg/L | Drinking water | sid | 3 thru 13 | iv = intravenous
sid = single daily dose
bid = twice daily dose
qod = every other day In Vitro Delivery Efficiency Determination of Small Animal Aerosol Delivery System Dry powder amphotericin B was delivered to anesthetized rabbits via the inhalation (IH) route using an endotracheal tube connected to a small animal aerosol delivery system, involving an aerosol delivery device, as disclosed in U.S. Pat. No. 6,257,233, which is incorporated by reference herein in its entirety, connected to a small animal ventilator. In this regard, powder from a blister pack was actuated from the inhaler into a chamber. The small animal ventilator pushed the dispersed powder into an endotracheal tube. The delivery efficiency to the animal was determined by measuring the gravimetric mass of the powder collected on a filter connected to the end of the endotracheal tube. The mass collected on the filter was normalized to the actual blister pack fill weight. The delivery efficiency was used to calculate the estimated dose (mg) for the in vivo experiments.

Treatment Groups

Table 5, below, summarizes the treatment regimen.

TABLE 5

| Group No. | Test Article | Route of Administration | Average Number of Blister Packs | Target Dose of AmB (mg/kg) | Estimated Delivered Dose (mg/kg) | Number of Animals/ Gender |
|---|---|---|---|---|---|---|
| 1 | NA | NA | 0 | 0 | 0 | 10/F |
| 2 | NA | NA | 0 | 0 | 0 | 10/F |
| 3 | AmB | Inhalation | 20 | 1.5 | 0.6 | 10/F |

Figure 20:
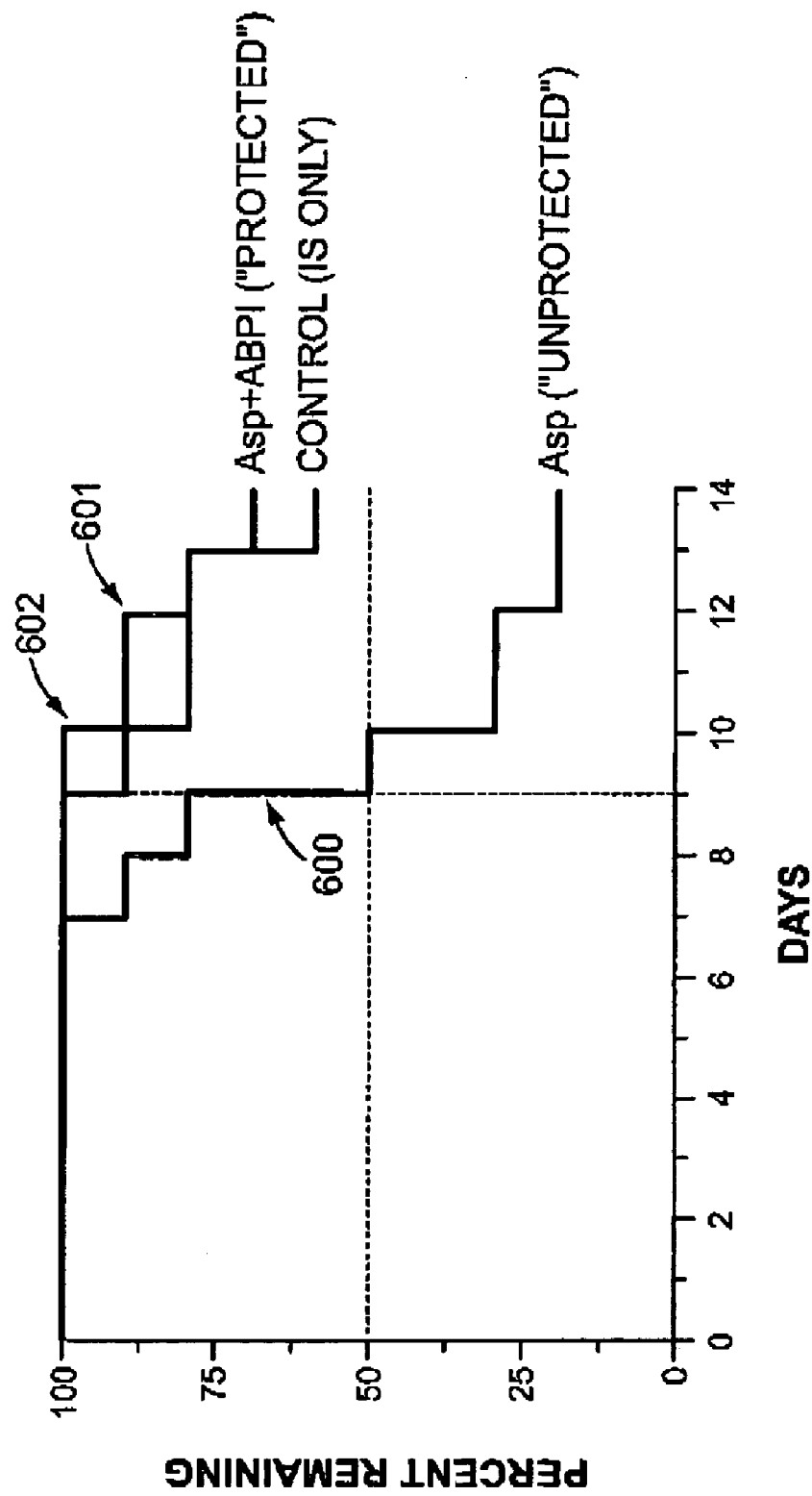
FIG. 20 is a Kaplan-Meier Survival Curve showing the effectiveness of one form of the present invention.

FIG. 20 shows Kaplan-Meier survival curves from the neutropenic rabbits. Of the rabbits that were immunosuppressed and were actively exposed to *Aspergillus fumigatus* 600, only 50% survived beyond nine days. In contrast, of the rabbits that were immunosuppressed, exposed to *Aspergillus fumigatus*, and administered amphotericin B 601, 100% survived beyond nine days. Curve 602 shows a control group of rabbits that were immunosuppressed only. In the longer term, less than 25% of the untreated exposed rabbits 600 survived beyond 14 days whereas about 70% of the treated and exposed rabbits 602 survived beyond 14 days.

EXAMPLE 12

Pharmacokinetics of Amphotericin B Delivered by Inhalation in Rabbits

This Example involves determining the concentrations of amphotericin B in the plasma, bronchoalveolar lavage (BAL) fluid, and lung tissue of rabbits following a single administration of amphotericin B powder by inhalation. This Example describes results obtained in the plasma and lung tissue only.

Materials and Methods

Amphotericin B (AmB) was formulated as an inhaleable powder containing 50 wt % active ingredient, using the process described in Example 2. The lot number of the formulation was N020042. The test powder was hand-filled into blister packs and contact sealed at 340° F. for 1.0 second, with an approximate fill weight of approximately 1.5 mg per blister pack.

The test article was delivered to anesthetized rabbits via the inhalation (IH) route using an endotracheal tube connected to a small animal aerosol delivery system, involving an aerosol delivery device, as disclosed in U.S. Pat. No. 6,257,233, which is incorporated by reference herein in its entirety, connected to a small animal ventilator. The test inhalation was administered in a single inhalation exposure.

The study included two groups each comprised of 48 rabbits. Groups 1 and 2 respectively received a target dose of 0.25 and 1.5 mg/kg amphotericin B IH. Four animals were sacrificed at each of the following time points after dosing: 0.16, 0.3, 1, 1.3, 2, 3, 4, 5, 14, 21, 28, and 45 days. Plasma and lung tissue were collected and analyzed for amphotericin B content using LC/MS. Limits of quantitation (LOQ) of the assays were 5 ng/ml in plasma and 20 ng/g in lung tissue.

Discussion and Conclusions

The objective of this Example was to determine the concentrations of amphotericin B in the plasma, BAL fluid, and lung tissue of rabbits following a single administration of amphotericin B powder by inhalation. Two target lung doses were examined 0.25 and 1.5 mg/kg. This Example describes results obtained in the plasma and lung tissue only.

The limit of quantitation (LOQ) in plasma was 5 ng/ml. Plasma amphotericin B concentrations of all animals, at all time points, and at both tested doses were below LOQ. Thus, there was little systemic exposure following IH administration of amphotericin B.

However, IH administration of amphotericin B resulted in high and persistent concentrations of the drug in the lung. Drug concentrations were achieved rapidly. Group mean concentrations of 4.2 and 24.2 μg/g were achieved by the first sampling time of 4 hours. The Tmax was observed at 32 and 24 hours for Groups 1 and 2, respectively, after administration for the 0.25 and 1.5 mg/kg doses. Group mean Cmax values were 8.0 and 46.6 μg/g for the 0.25 and 1.5 mg/kg doses, respectively. Cmax values were dose proportional.

Figure 21:
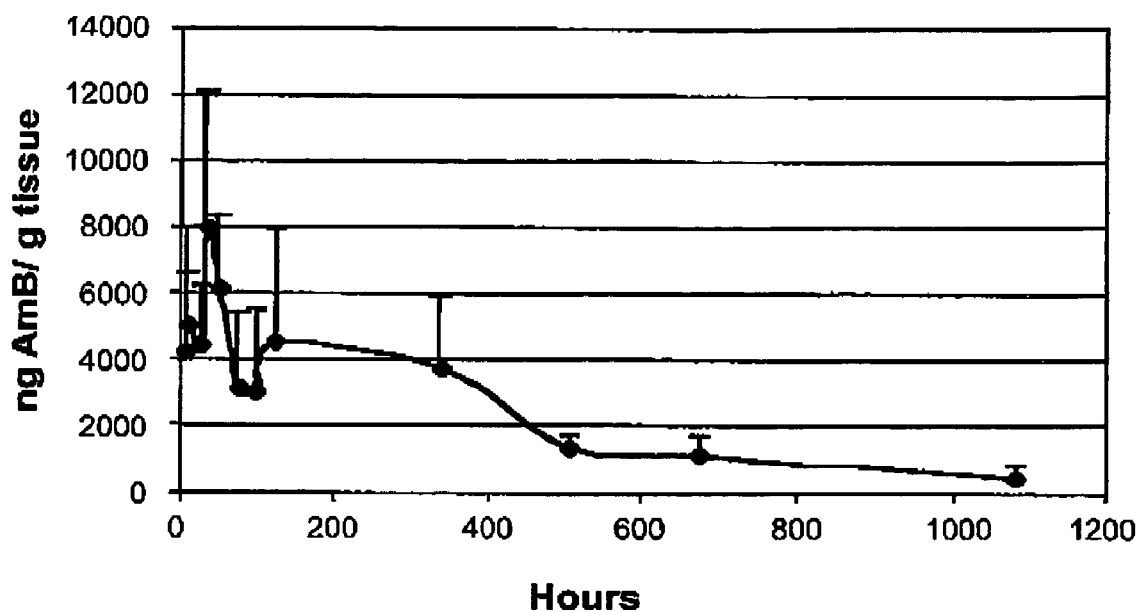
FIG. 21 shows group mean amphotericin B concentrations in lung tissue delivered by inhalation to rabbits.
Figure 22:
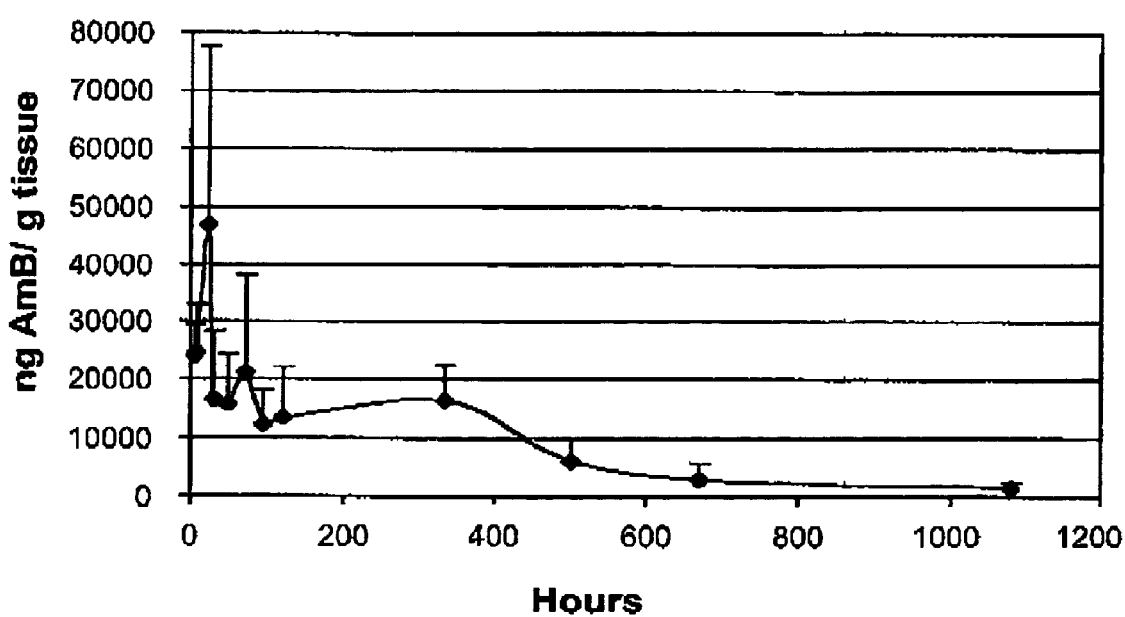
FIG. 22 shows group mean amphotericin B concentrations in lung tissue delivered by inhalation to rabbits.

Drug concentrations were maintained for several weeks following IH administration. As shown in FIGS. 21 and 22, group mean amphotericin B concentrations were still elevated at the last sampling time, i.e., 45 days following administration. The half-life ($t_{1/2}$) for amphotericin B elimination from the lung was 292 hours for the 0.25 mg/kg dose and was 254 hours for the 1.5 mg/kg dose.

The results of this Example demonstrate that IH administration of amphotericin B to rabbits results in plasma amphotericin B concentrations that are uniformly below LOQ (<5 ng/ml). They further show that high and persistent concentrations of amphotericin B are achieved in the lung tissue.

EXAMPLE 13

Efficacy of Inhaled Amphotericin B for Prophylaxis in Rabbits

This Example involves: (1) determining whether amphotericin B (AmB) concentrations in epithelial lining fluid (ELF) or lung parenchyma are more relevant in protection against *A. fumigatus* morbidity; and (2) establishing effective prophylactic dose.

Materials and Methods

The amphotericin B inhaleable powder of Example 14, lot number $NO_{20042}$, was used. The test powder was hand-filled into blister packs and contact sealed at 340° F. for 1.0 second, with an approximate fill weight of approximately 1.5 mg per blister pack.

The test article was delivered to anesthetized rabbits via the inhalation (1H) route using an endotracheal tube connected to a small animal aerosol delivery system, involving an aerosol delivery device, as disclosed in U.S. Pat. No. 6,257,233, which is incorporated by reference herein in its entirety, connected to a small animal ventilator. The test inhalation was administered in a single inhalation exposure.

New Zealand White SPF rabbits, dual catheterized with Vascular Access Ports to femoral veins, ~2.5 to 4.0 kg at study initiation were obtained from Covance Research Products, Denver Pa.

*Aspergillus fumigatus*, NIH strain 4215, was obtained from American Type Culture Collection (ATCC). Inoculum of *A. fumigatus* was prepared on Sabouraud dextrose flasks. Conidia were harvested with a solution of 0.025% Tween 20 in 0.9% sodium chloride, transferred to a conical tube, washed, and counted. The concentration was adjusted with the same solution to achieve $5 \times 10^7$ conidia in 300 µL. Animals in challenged groups were inoculated with the same volume. Inoculation was performed on anesthetized rabbits. Rabbits were intubated using an endotracheal tube and the inoculum was then administered intratracheally with a tuberculin syringe attached to a catheter introduced through the endotracheal tube.

The study included 6 groups each comprised of 10 rabbits. These groups are described in Table 6, below. All groups were immunosuppressed and treated with antibiotics to prevent bacterial infections. The immunosuppression and antibiotic cover regimen is detailed in Table 7, below. Group 1 was neither challenged with *A. fumigatus* not treated with amphotericin B and serves as a control for the immunosuppressive regimen. Group 2 was challenged with *A. fumigatus* but not treated with amphotericin B. Group 3 was treated with 1.5 mg amphotericin B/kg 12 days prior to *A. fumigatus* challenge. Group 4 was treated with 0.15 mg amphotericin B/kg 1 day prior to *A. fumigatus* challenge. Group 5 was treated with 0.5 mg amphotericin B/kg 1 day prior to *A. fumigatus* challenge. Group 6 was treated with 1.5 mg amphotericin B/kg 1 day prior to *A. fumigatus* challenge.

TABLE 6

| Group | Description | Immunosuppression | *Aspergillus fumigatus* inoculation | AmB Treatment (mg/kg) | AmB Treatment (day) |
|---|---|---|---|---|---|
| 1 | Immunosuppressed Uninoculated | Yes | No | 0 | NA* |
| 2 | Immunosuppressed Inoculated/Untreated | Yes | Yes | 0 | NA |
| 3 | Immunosuppressed Inoculated/Day-12 High Dose | Yes | Yes | 1.5 | Day-12 |
| 4 | Immunosuppressed Inoculated/Day-1 Low Dose | Yes | Yes | 0.15 | Day-1 |
| 5 | Immunosuppressed Inoculated/Day-1 Mid Dose | Yes | Yes | 0.5 | Day-1 |
| 6 | Immunosuppressed Inoculated/Day-1 High Dose | Yes | Yes | 1.5 | Day-1 |

*NA = Not Applicable

TABLE 7

| Drug | Purpose | Dose Level (mg/kg) | Route of Admin. | Frequency | Study Days[B] |
|---|---|---|---|---|---|
| Cytarabine | Immunosuppression | 44 mg/kg | iv | sid | −1, 1, 2, 3, 4 |
| Cytarabine | Maintain neutropenia | 40 mg/kg | iv | sid | 7, 8, 12, 13 |
| Methylprednisolone | Inhibit macrophage Function | 5 | iv | sid | −1, 1 |
| Ceftazidime | Prevent bacterial Infection | 75 | iv | bid | 3 ‖13 |
| Gentamicin | Prevent bacterial Infection | 5 | iv | qod | 3, 5, 7, 9, 11, 13 |
| Vancomycin | Prevent bacterial Infection | 15 | iv | sid | 3 ‖13 |
| Vancomycin | Prevent bacterial Infection | 50 mg/L[A] | Drinking water | sid | 3 ‖13 |

TABLE 7-continued

| Drug | Purpose | Dose Level (mg/kg) | Route of Admin. | Frequency | Study Days[B] |
|---|---|---|---|---|---|
| Amphotericin | Therapeutic Treatment | Low, mid, high doses | Inhalation | sid | −12 or −1 |

[A]mg/liter of drinking water
[B]Study Day 1 = day of inoculation with *A. fumigatus*

Results

Figure 23:
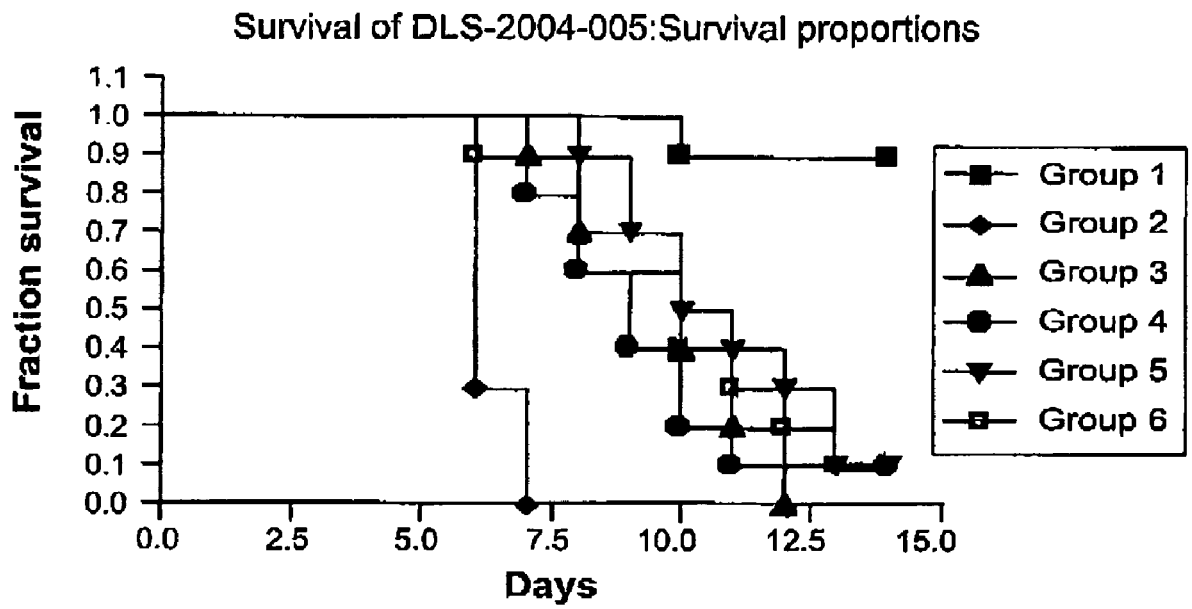
FIG. 23 is a Kaplan-Meier Survival Curve showing the effectiveness of one form of the present invention.

Survival data is presented in FIG. 23. Group 1 was immunosuppressed but neither treated with amphotericin B nor challenged with *A. fumigatus*. All but 1 rabbit in this group survived to the conclusion of the study at day 14 giving a survival rate of 90%.

Group 2 was immunosuppressed, not treated with amphotericin B but challenged with *A. fumigatus*. All rabbits in this group died giving a survival rate of 0%. The median survival time was 6 days.

Group 3 was immunosuppressed, treated at day −12 with 1.5 mg amphotericin B/kg, and challenged with *A. fumigatus*. All rabbits in this group died giving a survival rate of 0%. The median survival time was 10 days.

Group 4 was immunosuppressed, treated at day −1 with 0.15 mg amphotericin B/kg, and challenged with *A. fumigatus*. Nine rabbits in this group died giving a survival rate of 10%. The median survival time was 9 days.

Group 5 was immunosuppressed, treated at day −1 with 0.5 mg amphotericin B/kg, and challenged with *A. fumigatus*. Again 9 rabbits in this group died giving a survival rate of 10%. The median survival time was 10.5 days.

Group 6 was immunosuppressed, treated at day −1 with 1.5 mg amphotericin B/kg, and challenged with *A. fumigatus*. Nine rabbits in this group died giving a survival rate of 10%. The median survival time was 10 days.

Pairwise statistical comparisons of Groups 2 v. 3, 2 v. 4, 2 v. 5, and 2 v. 6 using the Logrank test indicates that inhaled amphotericin B confers significant (P<0.001) protection against *A. fumigatus* challenge. Pairwise comparison of Groups 3, 4, 5, and 6 using the same test does not reveal any difference in the survival curves resulting from the different treatments.

Discussion and Conclusions

This Example examined the protective effect of inhaled amphotericin B on immunosuppressed rabbits inoculated with *A. fumigatus* spores. Comparison of the survival curves of Group 2, inoculated with *A. fumigatus* but untreated, with any of the treated groups indicates that treatment with amphotericin B by inhalation was protective in immunosuppressed rabbits. This was true at all the doses tested (0.15, 0.5, and 1.5 mg/kg). It was also true whether the rabbits were treated 1 or 12 days before *A. fumigatus* challenge.

EXAMPLE 14

One Month Inhalation Toxicity Study in Rats

This Example involved assessing the toxicity of a dry powder formulation of amphotericin B in rats following inhalation administration and evaluating the reversibility of any effects after an approximate one month recovery period. This Example involved looking for locally induced toxicity in the respiratory tract and systemic toxicity.

Amphotericin B powder containing 50 wt % active ingredient was formulated by using the process described in Example 2. The resulting powder had the characteristics shown in Table 8, below.

TABLE 8

| API Lot No. | Mfg. | API, % Crystalline | API Particle Size, ×50 (μm) | Powder Lot Number | Powder, % Crystalline | Powder MMAD, Gravimetric (μm) | Powder MMAD, Drug Specific (μm) |
|---|---|---|---|---|---|---|---|
| 101677 | Chemwerth | 90 | 1.25 | 4001T | 95 | 2.2 | 2.3 |

Rats (198 M and 198 F) were allocated to 6 dose groups and treated as shown in Table 9, below.

TABLE 9

| Dose Group/ Treatment | Day 1 Target formulation Dose Levels (mg/kg/day) | Days 8, 15, 22 and 29 Target Formulation Dose Level (mg/kg/day) | Number of Animals | | |
|---|---|---|---|---|---|
| | | | | Males | Females |
| Air Control | 0 | 0 | Main Study | 101-110 | 129-138 |
| | | | Toxicokinetic | 111-128 | 139-156 |
| Vehicle Control | 80 | 80 | Main Study | 201-210 | 235-244 |
| | | | Recovery | 211-216 | 245-250 |
| | | | Toxicokinetic | 217-234 | 251-268 |

TABLE 9-continued

| Dose Group/ Treatment | Day 1 Target formulation Dose Levels (mg/kg/day) | Days 8, 15, 22 and 29 Target Formulation Dose Level (mg/kg/day) | | Number of Animals | |
|---|---|---|---|---|---|
| | | | | Males | Females |
| Low Dose | 2* | 0.4* | Main Study | 301-310 | 335-344 |
| | | | Recovery | 311-316 | 711, 346-550 |
| | | | Toxicokinetic | 317-334 | 351-368 |
| Intermediate Dose I | 10* | 2* | Main Study | 401-409, 701 | 435, 712, 437-444 |
| | | | Recovery | 411-416 | 445-450 |
| | | | Toxicokinetic | 417-434 | 451-468 |
| Intermediate Dose II | 30* | 6* | Main Study | 501-510 | 535-540, 713, 542-544 |
| | | | Recovery | 511-516 | 545-550 |
| | | | Toxicokinetic | 517-534 | 551-568 |
| High Dose | 80* | 80* | Main Study | 601-610 | 635-644 |
| | | | Recovery | 611-616 | 645-650 |
| | | | Toxicokinetic | 617-634 | 651-668 |

*Dry Powder formulation containing about 50 wt % amphotericin B
Recovery animals were retained for an approximate one month post dose recovery period Animal 410M died prematurely on Day-1 and was replaced by 701M. Following pretrial ophthalmoscopy examinations, Animals 345F, 436F, and 541F were replaced by 711F, 712F, and 713F, respectively The animals were dosed using a snout only exposure technique for about 60 min on 5 occasions at weekly intervals. Recovery animals were retained for an approximate one month recovery period.

The following investigations were performed: clinical observations, body weight, food consumption, ophthalmology, hematology, clinical chemistry, urinalysis, histopathology, and toxicokinetics.

The overall group mean exposure chamber concentration of vehicle formulation aerosol was 2.35 mg/L. Overall group mean exposure chamber concentrations of amphotericin B formulation were 0.06, 0.39, and 0.91 mg/L on Day 1 and 0.02, 0.06, and 0.16 mg/L on subsequent days for Groups 3, 4, and 5, respectively. Overall group mean exposure chamber concentrations of amphotericin B alone (determined analytically) were 0.0290, 0.152, and 0.389 mg/L on Day 1 and 0.00847, 0.0214, and 0.0519 on subsequent days for Groups 3, 4, and 5, respectively. For Group 6, the overall group mean exposure chamber concentration for amphotericin B formulation was 2.22 mg/L or 0.694 mg/L for amphotericin B alone.

The overall (sex combined) group mean estimated achieved dosage of vehicle formulation was 73.56 mg/kg/dose. Overall (sex combined) group mean estimated achieved dosages of amphotericin B formulation were 1.89, 12.27, and 28.45 mg/kg on Day 1 and 0.528, 1.74, and 4.87 mg/kg/day on subsequent days for Groups 3, 4, and 5, respectively. Overall (sex combined) group mean estimated achieved dosages of amphotericin B alone (determined analytically) were 0.914, 4.78, and 12.36 mg/kg on Day 1 and 0.256, 0.646, and 1.58 mg/kg on subsequent days for Groups 3, 4, and 5, respectively. For Group 6, the overall (sex combined) group mean estimated achieved dosage of amphotericin B formulation was 68.24 mg/kg/dose or 21.64 mg/kg/dose for amphotericin B alone.

Particle size distribution data indicated that 64.7% of the vehicle aerosol particles were less than 3.5 µm, with a mass median aerodynamic diameter (MMAD) (±geometric standard deviation (GSD)) of 1.61 µm (3.244), 81.2%, 60.6%, and 70.7% of amphotericin B formulation particulates were below 3.5 µm on Day 1, and 68.2%, 59.0%, and 83.6% were below 3.5 µm on subsequent days with MMADs and (GSDs) of 1.35 µm (2.382), 1.46 µm (4.508), and 1.43 µm (2.560) on Day 1 and 1.42 µm (3.572), 1.89 µm (2.710), and 0.81 µm (4.329) on subsequent days for Groups 3, 4, and 5, respectively.

For amphotericin B alone (determined analytically) 68.1%, 58.1%, and 68.6% of particulates were below 3.5 µm on Day 1 and 66.2%, 55.6%, and 71.1% were below 3.5 µm on subsequent days with MMADs and (GSDs) of 1.69 µm (2.755), 1.71 µm (3.351), and 1.55 µm (2.652) on Day 1 and 1.47 µm (3.599), 2.29 µm (2.525), and 1.06 µm (6.077) on subsequent days for Groups 3, 4, and 5, respectively. For Group 6, particle size data indicated that 57.8% of amphotericin B formulation particulates were below 3.5 µm with a MMAD (+GSD) of 2.11 µm (3.089). For amphotericin B alone (determined analytically) 54.3% of particulates were below 3.5 µm with a MMAD (±GSD) of 2.29 µm (2.966).

The particulates were considered respirable to the test species.

There were no adverse effects on body weight, food consumption, ophthalmology, hematology, clinical chemistry, or organ weights.

There were 181 mortalities during the study, most of which were correlated to clinical signs indicative of respiratory distress including wheezing, crackling, and gasping respiration, which were observed among animals in all amphotericin B treated groups. One death occurred pretrial, and was therefore not considered to be related to treatment.

Necropsy findings in the lungs related to administration of amphotericin B included a mass, adhesions, abnormal contents, raised area/foci, pale foci, consolidation, as well as dark foci, and dark, discolored or spongy lungs. Abnormal contents were noted in the trachea or bronchi of two Group 6 (high dose) animals. Following an approximate one month recovery period, there were lung adhesions in one female animal, Group 3 (low dose).

Microscopically, findings in the lungs of animals given amphotericin B included pneumonia, pleuritis, lobar collapse, luminal exudate in bronchi/bronchioles, bronchial mucosal hypertrophy, increased inflammatory cell infiltration, alveolar inflammation and eosinophil infiltration, as well as congestion/hemorrhage. Pneumonia/pleuritis, collapse or alveolar inflammation were found in 17/110 animals from Groups 3 to 6 in the Main Study.

There were correlations between necropsy and histology findings in the lungs, particularly between adhesions and pleuritis; and between a mass, consolidation, raised area/foci or abnormal contents and pneumonia. Secondary to pneumonia, other findings included necrosis with inflammation in spleen and liver, increased granulopoiesis in sternum and femur, atrophy of lymphoid tissues, peripheral hepatocyte vacuolation and diffuse adrenal cortical cell hypertrophy.

There were no notable differences in the incidence or severity of these findings between any of the amphotericin B treated groups.

Following an approximate one month recovery period, minimal or mild tracheal mucosal hypertrophy was still present in some animals given amphotericin B. There was chronic inflammation and pleuritis in the lungs of Animal 344, one of 18 animals from Groups 3 and 4 in the Recovery Study. The inflammation was characterized by lymphocytic foci and accumulations of pigmented macrophages.

Toxicokinetic analyses revealed that the maximum plasma concentrations generally increased with dose and were generally reached within 4 h of cessation of dosing. No quantifiable levels of amphotericin B were detected in Air or Vehicle Control samples.

In conclusion, snout only administration of amphotericin B at dosages up to 21.64 mg/kg/dose resulted in severe clinical signs indicative of respiratory distress and the premature termination of many animals from all amphotericin B treated groups, including all animals from Groups 5 and 6. Inhalation administration of amphotericin B at all doses was associated with tracheal mucosal hypertrophy associated with a luminal exudate and/or diffuse inflammatory cell infiltration; and in the lungs with pneumonia, pleuritis, lobar collapse, luminal exudate in bronchi/bronchioles, bronchial mucosal hypertrophy and increased inflammatory cell infiltration, alveolar inflammation and eosinophil infiltration, as well as congestion/hemorrhage. Following an approximate one month recovery period, there were reductions in the incidence and severity of tracheal mucosal hypertrophy and pulmonary inflammation.

EXAMPLE 15

Dry Powder Toxicology Study in Rats with Daily or Weekly Dosing

This Example involved determining the toxicity of two different dry powder batches of amphotericin B in rats following inhalation administration using two different dosing regimens. The information obtained was used to select dose levels and/or dose regimens for subsequent toxicity studies.

Figure 24:
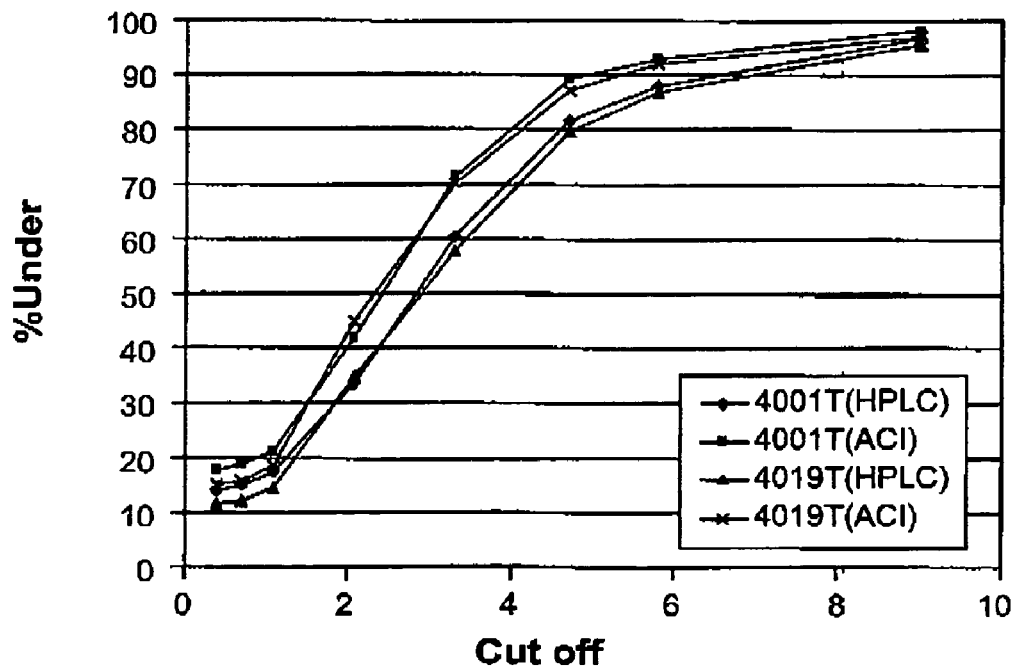
FIG. 24 is a plot comparing the gravimetric and drug-specific particle size distributions of two powders of the present invention.

Amphotericin B powders containing 50 wt % active ingredient were formulated by using the process described in Example 2. The resulting powders had the characteristics shown in Table 10, below. Furthermore, as shown in FIG. 24, the powders were inhomogeneous as measured by drug-specific aerosol particle size versus gravimetric particle size analysis, using an inhaler device as shown in U.S. application Ser. No. 10/298,177, which is herein incorporated by reference in its entirety.

TABLE 10

| API Lot No. | Mfg. | API,% Crystalline | API Particle Size, x50 (μm) | Powder Lot No. | Powder, % Crystalline | Powder MMAD, Gravimetric (μm) | Powder MMAD, Drug Specific (μm) |
| --- | --- | --- | --- | --- | --- | --- | --- |
| 100370 | Alpharma | 11 | NA | 4001T | NA | NA | 2.8 |
| 100581 | Alpharma | 48 | 3.53 | 4019T | 56 | 2.3 | 2.8 |

NA = not available

Ninety male rats were allocated to 10 dose groups and treated as shown in Table 11, below.

TABLE 11

| Dose Group/Treatment | Day 1 Target Formulation Dose Levels (mg/kg) | Days 2 and 3 Formulation Dose Levels (mg/kg) | Days 8 and 15 Formulation Dose Levels (mg/kg) | Animal Numbers |
| --- | --- | --- | --- | --- |
| 1. Vehicle Control | 80 | 80 | N/A | 1-9 |
| 2. Low Dose $^A$ | 30* | 6* | N/A | 10-18 |
| 3. High Dose$^A$ | 80* | 80* | N/A | 19-27 |
| 4. Low Dose $2^B$ | 30* | 6* | N/A | 28-36 |
| 5. High Dose $2^B$ | 80* | 80* | N/A | 37-45 |
| 6. Vehicle Control 2 | 80 | N/A | 80 | 46-54 |
| 7. Low Dose $3^A$ | 30* | N/A | 6* | 55-63 |
| 8. High Dose $3^A$ | 80* | N/A | 80* | 64-71, 91 |
| 9. Low Dose $4^B$ | 30* | N/A | 6* | 73-81 |
| 10. High Dose $4^B$ | 80* | N/A | 80* | 82-90 |

*= Dry Powder formulation containing 50 wt % amphotericin B
$^A$= Dosed using amphotericin B Lot 4001T
$^B$= Dosed using amphotericin B Lot 4019T
N/A = Not applicable
Animal 72 (Group 9) was replaced with Animal 91 prior to commencement of dosing The animals were dosed using a snout only exposure technique once for 1 h per day according to the Table 11, above.

The following investigations were performed: clinical observations, body weight, hematology, clinical chemistry, organ weight, histopathology, toxicokinetics, and bioanalytical chemistry.

The overall group mean exposure concentration of vehicle formulation aerosols were 2.23 and 2.11 mg/L for Groups 1 and 6, respectively. Overall group mean exposure chamber concentrations of amphotericin B formulation were 1.01, 0.88, 1.01, and 0.88 mg/L on Day 1 and 0.18, 0.17, 0.17, and 0.18 mg/L on subsequent days for Groups 2, 4, 7, and 9, respectively. Overall exposure chamber concentrations of amphotericin B formulation were 2.25, 2.33, 2.51, and 2.41 mg/L for Groups 3, 5, 8, and 10, respectively.

Overall group mean exposure chamber concentrations of amphotericin B alone (determined analytically) were 0.353, 0.306, 0.353, and 0.306 mg/L on Day 1 and 0.0684, 0.0598, 0.0615, and 0.0783 mg/L on subsequent days for Groups 2, 4, 7, and 9, respectively. Overall group mean exposure chamber concentrations of amphotericin B alone (determined analytically) were 0.856, 0.927, 0.963, and 0.987 mg/L for Groups 3, 5, 8, and 10, respectively.

The overall group mean estimated achieved dosage of vehicle formulation was 72.79 and 66.34 mg/kg/day for Groups 1 and 6, respectively. Overall group mean estimated achieved dosages of amphotericin B formulation were 33.44, 29.14, 33.44, and 28.95 mg/kg on Day 1 and 2.25, 5.55, 5.22, and 5.49 mg/kg on subsequent days for Groups 2, 4, 7, and 9, respectively. Overall group mean estimated achieved dosages of amphotericin B formulation were 74.85, 75.00, 77.81, and 77.41 mg/kg/dose for Groups 3, 5, 8, and 10, respectively.

Overall group mean estimated achieved dosages of amphotericin B alone (determined analytically) were 11.69, 10.13, 11.69, and 10.07 mg/kg on Day 1 and 2.25, 1.96, 1.89, and 2.38 mg/kg on subsequent days for Groups 2, 4, 7, and 9, respectively. Overall group mean estimated achieved dosages of amphotericin B alone (determined analytically) were 24.45, 29.97, 29.91, and 30.60 for Groups 3, 5, 8, and 10, respectively.

Particle distribution data indicated that 69.7% and 77.6% of vehicle aerosol particles were less than 3.5 μm, with a mass median aerodynamic diameter (MMAD) (±geometric standard deviation (GSD)) of 1.38 μm (2.880) and 1.43 (2.281) for Groups 1 and 6, respectively. 63.0%, 69.2%, 63.0%, and 69.2% of amphotericin B formulation particulates were below 3.5 μm, with MMADs and (GSDs) of 1.36 μm (4.603), 1.54 μm (2.502), 1.36 μm (4.603), and 1.54 μm (2.502) on Day 1 for Groups 2, 4, 7, and 9, respectively. On subsequent days, 77.2%, 69.8%, 71.3%, and 61.3% of amphotericin B formulation particulates were less than 3.5 μm with MMADs (GSDs) of 0.79 μm (4.541), 1.75 μm (2.455), 1.56 μm (3.618), and 2.16 μm (3.228) for Groups 2, 4, 7, and 9, respectively. 69.2%, 63.4%, 64.7%, and 61.8% of amphotericin B formulation particulates were less than 3.5 μm, with MMADs (GSDs) of 0.95 μm (4.344), 1.44 μm (4.312), 1.10 μm (4.759), and 1.52 μm (4.233) for Groups 3, 5, 8, and 10, respectively.

For amphotericin B alone (determined analytically) 56.4%, 61.9%, 56.4%, and 61.9% of aerosol particles were below 3.5 μm, with MMADs (GSDs) of 1.58 μm (3.563), 1.71 μm (3.309), 1.58 μm (3.563), and 1.71 μm (3.309) on Day 1 for Groups 2, 4, 7, and 9, respectively. On subsequent days, 66.8%, 57.4%, 62.0%, and 63.0% of aerosol particles were below 3.5 μm, with MMADs (GSDs) of 1.09 μm (4.181), 1.95 μm (3.386), 1.42 μm (3.372), and 1.83 μm (3.075) for Groups 2, 4, 7, and 9, respectively.

For Groups 3, 5, 8, and 10, respectively, 61.9%, 57.6%, 63.8%, and 61.5% of amphotericin B alone (determined analytically) were below 3.5 μm, with MMADs (GSDs) of 1.30 μm (4.208), 1.77 μm (3.782), 1.20 μm (4.608), and 1.58 (4.097).

Necropsy findings associated with the inhalation of amphotericin B included dark foci in the lungs, dark, reddened or spongy lungs, abnormal contents in the trachea and enlarged bronchial and cervical lymph nodes. Additionally, distended stomach and intestines were noted for animals killed prematurely.

Histological evaluation revealed: diffuse mucosal hypertrophy in the trachea in most animals treated with both lots of amphotericin B by inhalation at both dose regimens. There was an increase in the severity of the mucosal hypertrophy with the second dose regimen (inhalation of amphotericin B at Days 1, 8, and 15) compared to the first dose regimen (inhalation of amphotericin B at Days 1, 2, and 3). There was no significant difference between Lot 4001T (A) and Lot 4019T (B) in terms of incidence and severity of this finding.

Submucosal inflammatory cell infiltration and luminal exudates in the trachea were also expected with administration of amphotericin B by inhalation. These findings were mostly seen in the trachea of animals treated using the second dose regimen (inhalation of amphotericin B at Days 1, 8, and 15). The lower incidence of these findings and the lack of a clear dose-response relationship in the first dose regimen groups were thought to be due to the short duration of this regimen (inhalation of amphotericin B at Days 1, 2, and 3, termination of the animals at Day 4).

Bronchial luminal exudates, bronchopneumonia, and peribronchial/peribronchiolar inflammation or inflammatory cell infiltration were present in the lung, and were also expected findings with administration of amphotericin B. In animals with bronchopneumonia, bronchial exudate was also present, and bronchopneumonia was thought to have been caused by secondary infection resulting from plugging of the larger airways. The lower incidence of bronchial luminal exudates in the lung in the first dose regimen groups was thought to be due to the short duration of this regimen. The incidence of the lung findings was generally higher in the high dose groups than in the low dose groups.

Toxicokinetic analyses revealed that plasma concentrations increased with dose. No quantifiable levels of amphotericin B were detected in Vehicle Control samples.

In conclusion, snout only administration of amphotericin B (alone) at dosages up to 30.60 mg/kg/dose resulted in clinical signs indicative of respiratory distress and/or irritation and the premature demise of 3 animals. Inhalation administration of amphotericin B at all doses was associated with diffuse mucosal hypertrophy in the trachea, submucosal inflammatory cell infiltration, luminal exudates in the trachea and bronchi, bronchopneumonia and peribronchial/peribronchiolar inflammation or inflammatory cell infiltration in the lung. The severity of these findings was increased for the second dose regimen (inhalation of amphotericin B at Days 1, 8 and 15). The lung findings correlated to an apparent dose-related increase in lung weights, which was more significant for animals dosed using the second regimen. The increase was most significant in animals treated with amphotericin B Lot 4001T.

EXAMPLE 16

Toxicity of Two Dry Powders in Rats with Daily or Weekly Dosing

This Example involved determining the toxicity of two different dry powder batches of amphotericin B in rats following inhalation administration using two different dosing regimens.

Amphotericin B powders containing 50 wt % active ingredient were formulated by using the process described in Example 8. The resulting powders had the characteristics shown in Table 12, below.

TABLE 12

| API,% Crystalline | API Particle Size, x50 (μm) | ABIP Lot Number | ABIP, % Crystalline | ABIP MMAD, Gravimetric (μm) | ABIP MMAD, Drug Specific (μm) |
| --- | --- | --- | --- | --- | --- |
| 94 | NA | N020226 | 100 | 2.3 | 2.3 |
| 6 | 3.05 | N020227 | 4 | 2.5 | 3.2 |

NA = not available

One hundred twenty male rats were allocated to 10 dose groups and treated as shown in Table 13, below.

TABLE 13

| Dose Group/ Treatment | Day 1 Target Formulation Dose Levels (mg/kg) | Days 2 and 3 Formulation Dose Levels (mg/kg) | Days 8 and 15 Formulation Dose Levels (mg/kg) | Animal No./Designation | |
| --- | --- | --- | --- | --- | --- |
| 1. Vehicle Control | 30 | 6 | N/A | Main Study | 1-6 |
| | | | | Toxicokinetic | 7-12 |
| 2. Low Dose[A] | 10* | 2* | N/A | Main Study | 13-18 |
| | | | | Toxicokinetic | 19-24 |
| 3. High Dose[A] | 30* | 6* | N/A | Main Study | 25-30 |
| | | | | Toxicokinetic | 31-36 |
| 4. Low Dose 2[B] | 10* | 2* | N/A | Main Study | 37-42 |
| | | | | Toxicokinetic | 43-48 |
| 5. High Dose 2[B] | 30* | 6* | N/A | Main Study | 49-54 |
| | | | | Toxicokinetic | 55-60 |
| 6. Vehicle Control 2 | 30 | N/A | 6 | Main Study | 61-66 |
| | | | | Toxicokinetic | 67-72 |
| 7. Low Dose 3[A] | 10* | N/A | 2* | Main Study | 73-78 |
| | | | | Toxicokinetic | 79-84 |
| 8. High Dose 3[A] | 30* | N/A | 6* | Main Study | 85-90 |
| | | | | Toxicokinetic | 91-96 |
| 9. Low Dose 4[B] | 10* | N/A | 2* | Main Study | 97-102 |
| | | | | Toxicokinetic | 103-108 |
| 10. High Dose 4[B] | 30* | N/A | 6* | Main Study | 109-114 |
| | | | | Toxicokinetic | 115-120 |

*= Dry Powder formulation containing 50 wt % amphotericin B
[A]= Dosed using amphotericin B Lot N020226 (highly crystalline)
[B]= Dosed using amphotericin B Lot N020227 (highly amorphous)
N/A = Not applicable
Spare animals were numbered 121-126

The animals were dosed using a snout only exposure technique once for 1 h per day according to Table 13, above.

The following investigations were performed: clinical observations, body weight, respiratory measurements, hematology, clinical chemistry, histopathology, toxicokinetics, and bioanalytical chemistry.

The overall group mean exposure chamber concentration of vehicle formulations was 0.91 mg/L on Day 1 and 0.22 and 0.17 mg/L on subsequent days for Groups 1 and 6, respectively. Overall group mean exposure chamber concentrations of amphotericin B formulation were 0.31, 0.36, 0.31, and 0.36 mg/L on Day 1 and 0.056, 0.078, 0.073, and 0.088 mg/L on subsequent days for Groups 2, 4, 7, and 9, respectively, and 1.04, 0.94, 1.04, and 0.94 mg/L on Day 1 and 0.18, 0.21, 0.18, and 0.19 mg/L on subsequent days for Groups 3, 5, 8, and 10, respectively.

Overall group mean exposure chamber concentrations of amphotericin B alone (determined analytically) were 0.125, 0.124, 0.125, and 0.124 mg/L on Day 1 and 0.0166, 0.0249, 0.0277, and 0.0278 mg/L on subsequent days for Groups 2, 4, 7, and 9, respectively, and 0.455, 0.330, 0.455, and 0.330 mg/L on Day 1 and 0.0686, 0.0717, 0.0724, and 0.0687 mg/L on subsequent days for Groups 3, 5, 8, and 10, respectively.

The overall group mean estimated achieved dosage of vehicle formulation was 29.29 and 29.40 mg/kg on Day 1 and 6.87 and 4.98 mg/kg on subsequent days for Groups 1 and 6, respectively. Overall group mean estimated achieved dosages of amphotericin B formulation were 10.03, 11.63, 9.93, and 11.65 mg/kg on Day 1 and 1.80, 2.50, 2.19, and 2.66 mg/kg on subsequent days for Groups 2, 4, 7, and 9, respectively, and 33.48, 30.54, 33.83, and 30.58 mg/kg on Day 1 and 5.75, 6.76, 5.47, and 5.81 mg/kg on subsequent days for Groups 3, 5, 8, and 10, respectively.

Overall group mean estimated achieved dosages of amphotericin B alone (determined analytically) were 4.04, 4.01, 4.00, and 4.01 mg/kg on Day 1 and 0.53, 0.79, 0.83, and 0.84 mg/kg on subsequent days for Groups 2, 4, 7, and 9, respectively, and 14.65, 10.72, 14.80, and 10.74 mg/kg on Day 1 and 2.19, 2.31, 2.20, and 2.11 mg/kg on subsequent days for Groups 3, 5, 8, and 10, respectively.

Particle size distribution data indicated that 70.8% of the vehicle aerosol particles were less than 3.5 μm on Day 1 and 77.1% and 75.6% were less than 3.5 μm for Groups 1 and 6, respectively, on subsequent days with a mass median aerodynamic diameter (MMAD) (±geometric standard deviation (GSD)) of 1.56 μm (2.832) on Day 1 and 0.84 μm (3.446) and 1.24 (2.948) for Groups 1 and 6, respectively, on subsequent days, 65.1%, 75.7%, 65.1%, and 75.7% of amphotericin B formulation aerosol particles were below 3.5 μm on Day 1 and 52.2%, 79.4%, 65.8%, and 75.2% were below 3.5 μm on subsequent days with MMADs and (GSDs) of 1.77 μm (3.787), 2.06 μm (2.805), 1.77 μm (3.787), and 2.06 μm (2.805) on Day 1 and 2.88 μm (2.269), 1.81 μm (2.540), 1.97 μm (2.719), and 2.14 μm (2.288) on subsequent days for Groups 2, 4, 7, and 9, respectively. 72.0%, 78.9%, 72.0%, and 78.9% of amphotericin B formulation particulates were below 3.5 μm on Day 1 and 68.6%, 76.0%, 72.4%, and 77.5% were below 3.5 μm on subsequent days with MMADs and (GSDs) of 2.07 μm (2.368), 1.87 μm (2.464), 2.07 μm (2.368), and 1.87 μm (2.464) on Day 1 and 1.67 μm (3.466), 1.77 μm (2.378), 1.42 μm (2.965), and 1.40 μm (2.911) on subsequent days for Groups 3, 5, 8, and 10, respectively.

For amphotericin B alone (determined analytically) 70.4%, 72.6%, 70.4%, and 72.6% of particulates were below 3.5 μm on Day 1 and 68.0%, 75.3%, 77.3%, and 63.0% were below 3.5 μm on subsequent days with MMADs and (GSDs) of 1.80 μm (2.563), 2.06 μm (2.702), 1.80 μm (2.563), and 2.06 μm (2.702) on Day 1 and 2.05 μm (2.230), 2.01 μm (2.752), 1.99 μm (2.005), and 2.60 μm (2.463) on subsequent days for Groups 2, 4, 7, and 9 respectively. 55.4%, 69.9%, 68.0%, and 69.6% of particulates were below 3.5 μm on Day 1 and 67.9%, 63.6%, 67.8%, and 63.3% were below 3.5 μm on subsequent days with MMADs and (GSDs) of 2.74 μm (2.116), 2.03 μm (2.788), 2.05 μm (2.230), and 2.03 μm (2.788) on Day 1 and 1.81 μm (2.428), 1.94 μm (3.310), 1.92 μm (2.402), and 2.04 μm (3.236) on subsequent days for Groups 3, 5, 8, and 10, respectively.

Toxicokinetic analyses revealed that plasma concentrations of amphotericin B generally increased with dose. No quantifiable levels of amphotericin B were detected in Vehicle Control samples.

There were no notable necropsy findings associated with the inhalation of amphotericin B.

Histological evaluation revealed diffuse mucosal hypertrophy in many animals treated with both dry powder batches of amphotericin B at both dose regimens. There was an increase in the incidence and severity of hypertrophy with amphotericin B N020227 (highly amorphous) compared with amphotericin B N020226 (highly crystalline). There also appeared to be a marginal increase in the incidence and severity of hypertrophy found with the second dose regimen (Days 1, 8, and 15) when compared with the first dose regimen (Days 1, 2, and 3).

Diffuse tracheal inflammation was also expected with inhalation of amphotericin B. The incidence and severity of these lesions was increased with amphotericin B N020227 (highly amorphous) compared with amphotericin B N020226 (highly crystalline). The incidence of the lesions decreased with the second dose regimen (weekly) compared to the first dose regimen (daily).

The tracheal and bronchial luminal exudates were only found in animals treated with amphotericin B N020227 (highly amorphous).

In conclusion, snout only administration of amphotericin B (alone) at dosages up to 14.80 mg/kg resulted in clinical signs indicative of respiratory distress. Inhalation of amphotericin B dry powder formulations N020226 (highly crystalline) and N020227 (amorphous), at Days 1, 2, and 3 or days 1, 8, and 15, was associated with tracheal and bronchial mucosal hypertrophy, tracheal inflammation, bronchial mucosal inflammatory cell infiltrate and tracheal and bronchial luminal exudates. Findings were increased in incidence and severity with amphotericin B N020227 (amorphous) compared with amphotericin B N020226 (highly crystalline). There was a marginal increase in incidence and severity of hypertrophy with the second dose regimen (Days 1, 8, and 15) compared with the first (Days 1, 2, and 3), although the severity and incidence of tracheal inflammation was reduced. There was little difference between high and low dose groups treated with amphotericin B N020227 (highly amorphous) in either regimen. The effects were less severe and the incidence reduced in the low dose groups treated with amphotericin B N020226 (highly crystalline), for both dose regimens.

EXAMPLE 17

Toxicity of Two Dry Powders in Dogs with Daily or Weekly Dosing

This Example involved determining the toxicity of two different dry powder batches of amphotericin B in beagle dogs following once weekly administration by the inhalation route.

Amphotericin B powder containing 50 wt % active ingredient was formulated by using the process described in Example 8. The resulting powder had the characteristics shown in Table 14, below.

TABLE 14

| API, % Crystalline | API Particle Size, x50 (μm) | Powder Lot Number | Powder, % Crystalline | Powder MMAD, Gravimetric (μm) | Powder MMAD, Drug Specific (μm) |
|---|---|---|---|---|---|
| 94 | NA | N020226 | 100 | 2.3 | 2.3 |
| 6 | 3.05 | N020227 | 4 | 2.5 | 3.2 |

NA = not available

Four male and 4 female beagle dogs were allocated to 4 dose groups and treated as shown in Table 15, below.

TABLE 15

| Dose Group/ Treatment | Day 1 Target Formulation Dose Levels (mg/kg) | Day 8 and 15 Formulation Dose Levels (mg/kg) | Animal No./Sex |
|---|---|---|---|
| 1. Vehicle Control | 30 | 6 | 1M, 5F |
| 2. Low Dose[A] | 10* | 2* | 2M, 6F |
| 3. High Dose[A] | 30* | 6* | 3M, 7F |
| 4. High Dose[B] | 30* | 6* | 4M, 8F |

*= Dry powder formulation containing 50 wt % amphotericin B
[A]= Dosed using amphotericin B Lot N020226 (highly crystalline)
[B]= Dosed using amphotericin B Lot N020227 (highly amorphous)

The animals were dosed using a close fitting face mask (fitted with a mouth tube) system for 30 min per day according to Table 15, above.

The following investigations were performed: clinical observations, body weight, food consumption, hematology, clinical chemistry, respiratory measurements (tidal volume, respiratory rate, respiratory minute volume), histopathology, toxicokinetics, and bioanalytical chemistry.

The overall group mean exposure chamber concentration of vehicle formulation was 1.34 mg/L on Day 1 and 0.31 mg/L on subsequent days. Overall group mean exposure chamber concentrations of amphotericin B formulation were 0.73, 1.80, and 1.58 mg/L on Day 1 and 0.13, 0.33, and 0.33 mg/L on subsequent days for Groups 2, 3, and 4, respectively. Overall group mean exposure chamber concentrations of amphotericin B alone (determined analytically) were 0.236, 0.521, and 0.769 mg/L on Day 1 and 0.0427, 0.120, and 0.154 mg/L on subsequent days for Groups 2, 3, and 4, respectively.

The overall group mean (sex combined) estimated achieved dose levels of vehicle formulation was 29.3 mg/kg on Day 1 and 6.9 mg/kg on subsequent days. Overall group mean (sex combined) estimated achieved dose levels of amphotericin B formulation were 16.3, 45.1 and 33.0 mg/kg on Day 1 and 2.9, 8.1, and 6.7 mg/kg on subsequent days for Groups 2, 3, and 4, respectively. Overall group mean (sex combined) estimated achieved dose levels for amphotericin B alone (determined analytically) were 5.3, 13.0, and 16.0 mg/kg on Day 1 and 0.96, 3.0, and 3.2 mg/kg on subsequent days for Groups 2, 3, and 4, respectively.

Particle size distribution data indicated that 81.1% of the vehicle aerosol particles were below 5 µm on Day 1 and 78.9% were less than 5 µm on subsequent days, with a mass median aerodynamic diameter (MMAD) (±geometric standard deviation (GSD)) of 0.84 µm (4.553) on Day 1 and 1.41 µm (3.104) on subsequent days. 69.0%, 83.1%, and 43.3% of amphotericin B formulation particulates were below 5 µm on Day 1 and 85.9%, 67.6%, and 57.3% were below 5 µm on subsequent days with MMADs and (GSDs) of 1.96 µm (2.406), 1.17 µm (2.725), and 3.26 µm (2.789) on Day 1 and 0.69 µm (4.623), 1.62 µm (3.137), and 2.85 µm (2.692) on subsequent days for Groups 2, 3, and 4, respectively. For amphotericin B alone (determined analytically) 57.7%, 73.6%, and 46.2% of particulates were below 5 µm on Day 1, and 72.6%, 63.6%, and 62.8% were below 5 µm on subsequent days with MMADs and (GSDs) of 2.20 µm (2.644), 1.79 µm (2.378), and 3.32 µm (2.482) on Day 1 and 1.96 µm (2.507), 2.00 µm (2.526), and 2.48 µm (2.168) on subsequent days for Groups 2, 3, and 4, respectively.

There were no significant changes observed in body weight, hematology, clinical chemistry, food consumption, or respiratory measurement parameters.

All necropsy findings were typical of spontaneously arising background findings in dogs of this age. There were no necropsy findings that could be attributed to administration of amphotericin B.

All histopathology findings were typical of spontaneously arising background findings in dogs of this age. There were no histopathology findings that could be attributed to administration of amphotericin B.

Toxicokinetic analyses indicated quantifiable levels of amphotericin B were detected in the plasma of all treated animals (with the exception of Group 4 Animal 4M). Levels detected were comparable throughout all treated dose groups. No quantifiable levels of amphotericin B were detected in Vehicle Control samples.

In conclusion, once weekly inhalation administration of amphotericin B formulation (or amphotericin B as determined analytically) to beagle dogs at doses up to 8.2 (3.2) mg/kg was associated with salivation in all dose groups, (including the vehicle control). Incidental clinical signs including reddened gums were also observed for individual animals in Groups 2 and 4 with reddened ears also being observed in one animal in Group 2. Vomiting and regurgitating food was noted for one animal in Group 3. There were no changes observed in body weight, food consumption, hematology, clinical chemistry, or respiratory measurement profiles. There were no necropsy or histopathology findings that could be attributed to administration of amphotericin B. Particle size distribution measurements revealed that amphotericin B Lot N020227 (highly amorphous) at high dose levels had a significantly greater particle size than amphotericin B Lot N020226 (highly crystalline).

EXAMPLE 18

Fourteen-day Inhalation Toxicity Study in Rats

This Example involves a 14-day toxicology study of an amphotericin B formulation prepared using the method of Example 2. Eighty rats were dosed using a snout-only exposure technique for 60 min daily for at least 14 days at a target dose of 0 mg/kg (air control or vehicle only), 2.5 mg/kg, 10 mg/kg, or 25 mg/kg.

Recovery animals were retained for a 14-day post-dose recovery period. On study days 1 and 14, blood samples for toxicokinetic analysis were obtained from designated animals in the vehicle only and high-dose (25 mg/kg) groups at predose, 2 hr post dose, and 4 hr post dose. Toxicokinetic blood samples were also obtained during the 14-day recovery period on recovery days 7 and 14 for males, and on recovery day 14 only for females due to their lower body weight.

All study animals were subjected to a detailed necropsy on completion of the 14-day treatment period (day 15) or completion of the 14-day recovery period (day 29). During necropsy, lung tissue samples for toxicokinetic analysis were obtained from each animal. Amphotericin B concentrations in plasma were determined using a liquid chromatography-tandem mass spectrophotometer (LC-MS/MS) method (lower limit of quantitation [LLQ]=10 ng/mL), and amphotericin B concentration in lung tissue were determined using a high performance liquid chromatography (HPLC) method and visible light detection (LLQ=4 µg/g).

Amphotericin B was detectable in the plasma and lung tissue of all animals sampled that received amphotericin B powder. Concentration-time profiles in plasma or in lung were similar for both genders, independent of dose.

Amphotericin B did not accumulate appreciably in plasma after 14 days of dosing, and declined as would be predicted by published values for amphotericin B elimination half-life following intravenous (IV) administration. Plasma $C_{max}$ values were 1/1000 to 1/3000 of those found for comparable IV doses of liposomal amphotericin B.

Lung concentrations increased with increasing dose, but in a less than proportional manner. Mean lung concentrations at the end of dosing were 10- to 30-times higher than those reported for amphotericin B in lung after IV administration of a comparable dose of liposomal amphotericin B. Lung tissue exposure in this Example was notably greater than that previously reported following long-term IV administration. During the recovery period, lung concentrations declined at rates indicating elimination half-life ($t_{1/2}$) values of 22 and 34 days at the 1.1 and 12.4 mg/kg dose levels, respectively, similar to that reported for amphotericin B in lung after IV and inhalation administration of liposomal amphotericin B.

EXAMPLE 19

Fourteen-day Inhalation Toxicity Study in Dogs

This Example involves assessing the pulmonary and systemic toxicity of an amphotericin B formulation formed by using the method of Example 2, in dogs following inhalation administration for 14 consecutive days, and the reversibility of any effects at the high dose level after a 14-day recovery period, in a total of 28 dogs (14 M, 14 F).

Active drug was administered in doses of 1.4, 5.6, and 11.5 mg/kg, using a closed facemask system for 30 min daily. On study days 1 and 14, blood samples for toxicokinetic analysis were obtained from designated animals in the vehicle and high-dose groups before exposure and 2, 4, 8, 12, and 24 hr after exposure, and daily during the 14-day recovery period. Main-study animals were euthanized and necropsied on day 15, recovery animals on day 29, during which the right anterior lobe of each animal was obtained for toxicokinetic analysis. Amphotericin B concentrations in plasma were determined using a liquid chromatography-tandem mass spectrophotometer (LC-MS/MS) method (lower limit of quantitation [LLQ]=10 ng/mL), and amphotericin B concentrations in lung tissue were determined using a high performance liquid chromatography (HPLC) method and visible light detection (LLQ=4 µg/g).

Amphotericin B accumulated in plasma after 14 days of dosing, and declined as predicted by plasma elimination half-life values observed in this Example. The mean plasma Cmax value of dogs receiving 11.5 mg/kg was 1/25 of that reported for dogs receiving IV amphotericin desoxycholate and 1/1000 of that for dogs receiving IV liposomal amphotericin B administered daily for the same period.

Lung amphotericin B concentrations increased with increasing dose, but in a less than proportional manner. At the end of the exposure period, mean amphotericin B lung concentrations were 22 to 44 times higher than those reported after IV administration of amphotericin B desoxycholate or liposomal amphotericin B. Lung tissue exposure in this dog study was notably greater than that previously reported following long-term IV administration. During the recovery period, lung concentrations declined at a rate indicating an apparent elimination half-life of 18.8 days, similar to that reported after IV and inhalation administration of liposomal amphotericin B to rats.

EXAMPLE 20

Drug Product Stability Study

The stability of amphotericin B powders was evaluated, as shown in Table 16, below. In each case, the powder was contained within an HPMC capsule. The capsules were placed in a 25 cc HDPE bottle. Each bottle was double-pouched with desiccant in the outer pouch.

TABLE 16

| Lot Number | Strength (wt %) | Lot Target Fill Weight (mg powder per capsule) | Data Available for 2-8° C. (mos.) |
| --- | --- | --- | --- |
| 10017 | 5 | 9.43 | 18 |
| 10029 | 50 | 9.52 | 18 |
| 10247 | 50 | 10.62 | 9 |

A summary and conclusion of these stability observations is provided below.

Appearance

All three lots met the acceptance criteria for appearance at all test points and all conditions.

Content 5 wt % amphotericin B: For lot 10017, the initial result was 0.053 mg of amphotericin B per mg of powder. Over a period of 18 months, the results ranged from 0.049 to 0.053 mg amphotericin B per mg of powder at both storage conditions.

50 wt % amphotericin B: For lot 10029, the initial result was 0.507 mg of amphotericin B per mg of powder. Over a period of 18 months, the results ranged from 0.469 to 0.508 mg amphotericin B per mg of powder at both storage conditions.

For lot 10247, the initial result was 0.470 mg of amphotericin B per mg of powder. After 9 months of storage at 2-8° C., the results ranged from 0.448 to 0.446 mg amphotericin B per mg of powder. For storage at 25° C./60% RH, results at 1 month, 3 months, and 6 months were 0.441, 0.399, and 0.385 mg of amphotericin B per mg of powder, respectively.

Moisture

Initial results for the three lots ranged from 3-5 wt %. The water content ranged within 3-6 wt % after storage at both normal and accelerated storage conditions.

Emitted Dose

Initial mean ED for all lots ranged from 89-94% (8.9 mg/capsule to 10.0 mg/capsule). After storage at normal and accelerated conditions, results ranged from 88-96% (8.8-10.2 mg/capsule).

Residual Perflubron (PFOB)

PFOB assay is performed on the bulk powder prior to filling in capsules. The results on bulk powder from all lots tested were <0.1 wt %. PFOB was tested at the 12-month time-point for Lots 10017 and 10029. Levels were <0.05-0.1 wt %.

Aerobic Count and Specific Pathogens

Microbial limit testing was conducted at the initial test point for all lots. Testing was also performed after 12 months storage at 25° C./60% RH for Lots 10017 and 10029, and met the acceptance criterion.

Purity

The initial area normalized main peak purity for all lots ranged from 93.6-96.4%. During storage at normal and accelerated conditions, the main peak purity ranged from 94.0-96.5%.

Aerosol Particle Size

MMAD: Initial results for mass median aerodynamic diameter (MMAD) for the lots ranged from 2.7-3.0 μm. During storage at normal and accelerated conditions, the MMAD ranged from 2.6-3.1 μm.

Conclusion

The stability results presented herein demonstrate that the 5 wt % amphotericin B powder (10 mg) and 50 wt % amphotericin B powder (10 mg) are stable and exhibit acceptable product attributes, including appearance, amphotericin B content, purity, water content, microbial attributes, and aerosol performance when packaged and stored at 2-8° C.

EXAMPLE 21

Performance after Exposure to High Humidity

This Example involved defining the appropriate time period capsules can be left out of the pouch at 70% RH and still meet emitted dose acceptance criteria (% ED≧85% and ED≧8.5 mg)

Two formulations were examined: 5 wt % amphotericin B powder (Lot X1429) and 50 wt % amphotericin B powder (Lot N020242). The formulations were contained within capsules that were contained within pouches. To determine the ED, an inhaler device as shown in U.S. application Ser. No. 10/298,177, which is herein incorporated by reference in its entirety, was used. The device was equilibrated at 25° C./70% RH.

The capsules were exposed to 25° C./70% RH in specified intervals and before actuation. The ED was measured at 10 time points for a total of 10 ED actuations per formulation, as shown in Table 17, below.

TABLE 17

| Actuation # | Target Time Point (min) |
|---|---|
| 1 | 2 |
| 2 | 10 |
| 3 | 20 |
| 4 | 30 |
| 5 | 36 |
| 6 | 42 |
| 7 | 48 |
| 8 | 54 |
| 9 | 60 |
| 10 | 66 |

The results for Lot N020242 are shown in Table 18, below.

TABLE 18

ED (% RSD) = 8.66 mg (4)
ED range = 8.28-9.43 mg
% ED (% RSD) = 85% (4)
% ED range = 81-93%

| Sample # | Target time point (min) | Powder Mass Collected (mg) | ED (%) |
|---|---|---|---|
| 1 | 2 | 8.54 | 83 |
| 2 | 10 | 8.37 | 82 |
| 3 | 20 | 8.28 | 81 |
| 4 | 30 | 8.67 | 85 |
| 5 | 36 | 8.31 | 82 |
| 6 | 42 | 8.69 | 85 |
| 7 | 48 | 8.83 | 87 |
| 8 | 54 | 8.60 | 85 |
| 9 | 60 | 9.43 | 93 |
| 10 | 66 | 8.83 | 86 | results for Lot X1249 are shown in Table 19, below.

TABLE 19

ED (% RSD) = 9.16 (2)
ED range = 8.88-9.35 mg
% ED (% RSD) = 89% (2)
% ED range = 86-91%

| Sample # | Target time point (min) | Powder Mass Collected (mg) | ED (%) |
|---|---|---|---|
| 1 | 2 | 9.09 | 87 |
| 2 | 10 | 9.09 | 89 |
| 3 | 20 | 9.24 | 90 |
| 4 | 30 | 9.03 | 87 |
| 5 | 36 | 9.29 | 90 |
| 6 | 42 | 8.88 | 86 |
| 7 | 48 | 9.35 | 91 |
| 8 | 54 | 9.20 | 89 |
| 9 | 60 | 9.31 | 91 |
| 10 | 66 | 9.11 | 89 |

The above data shows no correlation in ED performance with increased exposure to high humidity. The average ED performance decreases under a high humidity environment, but still meets acceptance criteria. Average ED performance of Lot N020042 (50 wt % formulation) met acceptance criteria, but not all individual EDs were ≧85% and ≧8.5 mg.

Summary of Selected Examples

A summary of selected Examples is shown in Table 20, below.

TABLE 20

Average Inhaled Dose Levels of Formulation
Dose of Powder Formulation
(Dose of Active Drug)

| Example | Species (No./group) | Day 1 Dose Levels | Days 8, 15, 22, and 29 | Significant Findings |
|---------|---------------------|-------------------|------------------------|----------------------|
| 14 | Rat 10M/10F (main) 5M/5F (recover) 18M/18F (TK) | 0 (air control) | 0 (air control) | None |
|  |  | 73.6 (0; Vehicle) mg/kg | 73.6 (0; Vehicle) mg/kg | None [Recovery: None] |
|  |  | 1.9 (0.9) mg/kg [low dose] | 0.5 (0.26) mg/kg | ~35% Morbidity or Mortality by Day 28. Clinical signs: of respiratory effects (wheezing, gasping). Gross necropsy observations: Lung: adhesions, foci (dark), discolored or spongy lungs. Histopathology: trachea; minimal-to-moderate mucosal hypertrophy, inflammatory cell infiltration. Lung; inflammatory cell infiltration, congestion/hemorrhage. [Recovery: Minimal tracheal mucosal hypertrophy] |
|  |  | 12.3 (4.8) mg/kg [mid-1 dose] | 1.7 (0.65) mg/kg | ~26% Morbidity or Mortality by Day 28. Clinical signs: of respiratory effects (wheezing, gasping). Gross necropsy observations: Lung; foci (dark), consolidation, discolored or spongy lungs. Histopathology: trachea; minimal-to-moderate mucosal hypertrophy, inflammatory cell infiltration, and luminal exudates. Lung; moderate bronchial mucosal hypertrophy, luminal exudates, congestion/hemorrhage, pleuritis and pneumonia. [Recovery: Histopathology: Minimal tracheal mucosal hypertrophy] |
|  |  | 28.5 (12.4) mg/kg [mid-2 dose] | 4.9 (1.6) mg/kg | 100% Morbidity or Mortality by Day 19. Clinical signs: of respiratory effects (wheezing, gasping). Gross necropsy observations: Lungs: abnormal contents, foci (pale or dark), discolored and spongy lungs. Mucosa in trachea. Histopathology: trachea; minimal-to-moderate mucosal hypertrophy. Lung; minimal-to-moderate bronchial mucosal hypertrophy, luminal exudates, inflammatory cell infiltration, congestion/hemorrhage, pleuritis and pneumonia. [Recovery: No surviving animals] |
|  |  | 68.2 (21.6) mg/kg [high dose] | 68.2 (21.6) mg/kg | 100% Morbidity or Mortality by Day 20. Clinical signs: of respiratory effects (wheezing, gasping). Gross necropsy observations: Lungs: abnormal contents, foci (pale or dark), discolored and spongy lungs. Histopathology: trachea; minimal-to-moderate mucosal hypertrophy, inflammatory cell infiltration, and luminal exudates. Lung; minimal-to-moderate bronchial mucosal hypertrophy, luminal exudates, inflammatory cell infiltration, congestion/hemorrhage, pleuritis or pneumonia. [Recovery: No surviving animals] |

TABLE 20-continued

Average Inhaled Dose Levels of
Formulation
Dose of ABIP Formulation
(Dose of Active Drug)

| Example | Species (No./group) | Day 1 Dose Levels | Days 2 and 3 (Daily), or Days 8 and 15 (Weekly) | Significant Findings |
|---|---|---|---|---|
| 15 | Rat 10M (main) | 72.8 (0; vehicle) Lot 4001T; 33.4 (11.7) mg/kg | 72.8 (0; vehicle) Lot 4001T; 5.6 (2.1) mg/kg | None 1 animal in Daily X3 dose group became moribund (Day 2). Clinical signs of respiratory effects (mild-to severe wheezing or lung sounds). Distended stomach and intestines in moribund animal. Abnormal contents in trachea. Lungs with dark foci, reddened lungs. Histopathology: Trachea; minimal-to-mild mucosal hypertrophy with submucosal inflammatory cell infiltration and luminal exudates. Lung; peribronchial/peribronchiolar inflammation, alveolar macrophage accumulation and congestion/hemorrhage. |
| | | Lot 4001T: 73.4 (27.2) mg/kg | Lot 4001T: 73.4 (27.2) mg/kg | 1 animal in Daily X3 group became moribund (Day 2), 1 animal in Weekly X3 was found dead (Day 8). Clinical signs of respiratory effects (mild-to severe wheezing or lung sounds). Distended stomach and intestines in moribund animal. Lungs with dark foci. Histopathology: Trachea, minimal-to-moderate diffuse mucosal hypertrophy with submucosal inflammatory cell infiltration and luminal exudates. Lung; bronchial exudate, peribronchial/peribronchiolar inflammation, alveolar macrophage accumulation, congestion/hemorrhage and bronchopneumonia. |
| | | Lot 4019T; 29.1 (10.9) mg/kg | Lot 4019T; 5.6 (2.2) mg/kg | Clinical signs of respiratory effects (mild-to severe wheezing or lung sounds). Abnormal contents in trachea. Lungs with dark foci. Histopathology: Trachea; minimal-to-mild mucosal hypertrophy with submucosal inflammatory cell infiltration and luminal exudates. Lung; peribronchial/peribronchiolar inflammation, alveolar macrophage accumulation and congestion/hemorrhage. |
| | | Lot 4019T; 76.2 (30.3) mg/kg | Lot 4019T; 76.2 (30.3) mg/kg | Clinical signs of respiratory effects (mild-to severe wheezing or lung sounds). Abnormal contents in trachea. Lungs with dark foci, reddened or spongy lungs. Histopathology: Trachea; minimal-to-mild mucosal hypertrophy with submucosal inflammatory cell infiltration and luminal exudates. Lung; peribronchial/peribronchiolar inflammation, alveolar |

TABLE 20-continued

| Example | Species (No./group) | Day 1 Dose Levels | Days 8 and 15 | Significant Findings |
|---|---|---|---|---|
| 16 | Rat 6 M (main) 6M (TK) | Vehicle; 29.4 (0) mg/kg | Vehicle; 29.4 (0) mg/kg | macrophage accumulation and congestion/hemorrhage and bronchopnemonia. None |
| | | Lot N020226; 10.0 (4.0) mg/kg | Lot N020226; 2 (0.7) mg/kg | None (Weekly Regimen) |
| | | Lot N020226; 33.7 (14.8) mg/kg | Lot N020226; 5.7 (2.2) mg/kg | Trachea, Minimal diffuse mucosal hypertrophy and minimal inflammation (Daily and Weekly Regimens) |
| | | Lot N020227; 11.7(4.0) mg/kg | Lot N020227; 2.6 (0.8) mg/kg | Tracheobronchial, Minimal-to-Mild diffuse mucosal hypertrophy, minimal-to-mild inflammation and exudate. (Daily and Weekly Regimens) |
| | | Lot N020227; 30.6 (10.7) mg/kg | Lot N020227; 6.3 (2.2) mg/k | Tracheobronchial, Minimal-to-Mild diffuse mucosal hypertrophy, minimal-to-mild inflammation, and exudate (Daily and Weekly Regimens) NOEL for lot N020226 = A regimen of a single dose of 10 mg/kg on Day 1 and 2 mg/kg on Days 8 and 15. |

| | | Average Inhaled Dose Levels of Formulation Dose of Powder Formulation (Dose of Active Drug) | | |
|---|---|---|---|---|
| Example | Species (No./group) | Day 1 Dose Levels | Days 8 and 15 | Significant Findings |
| 17 | Beagle 4F | Vehicle 29.3 (0) mg/kg | Vehicle 6.9 (0) mg/kg | None |
| | | Lot N020226; 16.3 (5.3) mg/kg | Lot N020226; 2.9 (1.0) mg/kg | None |
| | | Lot N020226; 45.1 (13.0) mg/kg | Lot N020226; 8.1 (3.0) mg/kg | None |
| | | Lot N020227; 33.0 (16.0) mg/kg | Lot N020227; 6.7 (3.2) mg/kg | None |
| | | | | NOEL; Lot N020226; = A regimen of a single dose of 45.1(13.0) mg/kg on Day 1 and 8.1 (3.0) mg/kg on Days 8 and 15. NOEL; Lot N020227; = A regimen of a single dose of 33.0 (16.0) mg/kg on Day 1 and 6.7 (3.2) mg/kg on Days 8 and 15. |

Although several embodiments of the present invention has been described in considerable detail with regard to certain preferred versions thereof, other versions are possible, and alterations, permutations and equivalents of the version shown will become apparent to those skilled in the art upon a reading of the specification and study of the drawings. For example, the relative positions of the elements in the aerosolization device may be changed, and flexible parts may be replaced by more rigid parts that are hinged, or otherwise movable, to mimic the action of the flexible part. In addition, the passageways need not necessarily be substantially linear, as shown in the drawings, but may be curved or angled, for example. Also, the various features of the versions herein can be combined in various ways to provide additional embodiments of the present invention. Furthermore, certain terminology has been used for the purposes of descriptive clarity, and not to limit the present invention. Therefore, any appended claims submitted in relation to this disclosure should not be limited to the description of the preferred versions contained herein and should include all such alterations, permutations, and equivalents as fall within the true spirit and scope of the present invention.

What is claimed is:

1. A composition, for localized delivery to the lungs as a powder, the composition consisting essentially of:

particles comprising at least about 95 wt % of amphotericin B, wherein the particles comprise a crystallinity level of at least about 20%, a mass median diameter from 1.1 μm to 1.9 μm, and wherein at least about 80 wt % of the particles have a geometric diameter from 1.1 μm to 1.9 μm.

2. The composition of claim 1, wherein the amphotericin B has a crystallinity level of at least about 70%.

3. The composition of claim 1, wherein the amphotericin B has a crystallinity level of at least about 90%.

4. The composition of claim 1, wherein the amphotericin B has a crystallinity level ranging from about 50% to about 99%.

5. A composition, for localized delivery to the lungs as a powder, the composition consisting essentially of:
 particles comprising at least about 95 wt % of amphotericin B, the amphotercin B comprising a crystallinity level of at least about 70%, and wherein at least 80 wt % of the particles have a geometric diameter from 1.1 μm to 1.9 μm.

6. The composition of claim 5, wherein the amphotericin B has a crystallinity level of at least about 90%.

* * * * *